(12) United States Patent
Ashmore

(10) Patent No.: US 10,267,670 B2
(45) Date of Patent: Apr. 23, 2019

(54) MEAL LIFECYCLE MANAGEMENT SYSTEM

(71) Applicant: Bradley Charles Ashmore, Mountain View, CA (US)

(72) Inventor: Bradley Charles Ashmore, Mountain View, CA (US)

( * ) Notice: Subject to any disclaimer, the term of this patent is extended or adjusted under 35 U.S.C. 154(b) by 59 days.

(21) Appl. No.: 15/782,788

(22) Filed: Oct. 12, 2017

(65) Prior Publication Data

US 2018/0106662 A1   Apr. 19, 2018

Related U.S. Application Data

(60) Provisional application No. 62/416,062, filed on Nov. 1, 2016, provisional application No. 62/409,362, filed on Oct. 17, 2016.

(51) Int. Cl.
| | | |
|---|---|---|
| *G01G 19/414* | (2006.01) | |
| *G06F 19/00* | (2018.01) | |
| *G01G 19/415* | (2006.01) | |
| *G01G 21/22* | (2006.01) | |
| *G09B 19/00* | (2006.01) | |
| *G01G 19/42* | (2006.01) | |

(Continued)

(52) U.S. Cl.
CPC ....... *G01G 19/4146* (2013.01); *G01G 19/415* (2013.01); *G01G 19/42* (2013.01); *G01G 21/22* (2013.01); *G06F 19/3475* (2013.01); *G09B 19/0092* (2013.01); *G16H 20/60* (2018.01); *G16H 50/20* (2018.01); *G06F 16/00* (2019.01)

(58) Field of Classification Search
CPC .................................................. G01G 19/4146
See application file for complete search history.

(56) References Cited

U.S. PATENT DOCUMENTS

| | | | |
|---|---|---|---|
| 6,069,696 A | 5/2000 | McQueen et al. | |
| 6,850,861 B1 | 2/2005 | Faiola et al. | |

(Continued)

FOREIGN PATENT DOCUMENTS

| | | |
|---|---|---|
| CN | 203168679 U | 9/2013 |
| CN | 203168686 U | 9/2013 |

(Continued)

OTHER PUBLICATIONS

SITU—The Smart Food Nutrition Scale for iPhone & iPad, Situscale. com, webpage viewed Jul. 10, 2017, 6 pages.

(Continued)

*Primary Examiner* — John E Breene
*Assistant Examiner* — Jeffrey C Morgan
(74) *Attorney, Agent, or Firm* — Ascenda Law Group, PC

(57) ABSTRACT

A pressure-sensitive device and a computing device are configured to register various steps of a meal lifecycle, including one or more of food purchasing, meal preparation, the serving and consumption of a meal, use of leftovers, management of food inventory, the transferring of a food item from one container to another, the transferring of a food item into a container, the transferring of a portion of a food item into a container. A food item may be automatically identified based on a weight and footprint of the food item. In some instances, a database associates a food item with multiple footprints such that a food item may be identified regardless of its orientation on the pressure-sensitive device.

20 Claims, 39 Drawing Sheets

(51) Int. Cl.
  *G16H 50/20* (2018.01)
  *G16H 20/60* (2018.01)
  *G06F 16/00* (2019.01)

(56) References Cited

U.S. PATENT DOCUMENTS

| | | |
|---|---|---|
| 8,330,057 B2 | 12/2012 | Sharawi et al. |
| 8,770,983 B2 | 7/2014 | Batsikouras |
| 9,109,943 B2 | 8/2015 | Mager et al. |
| 9,198,605 B2 | 12/2015 | Contant |
| 2008/0052200 A1* | 2/2008 | Bodin .................. G06Q 10/087 705/28 |
| 2011/0167100 A1 | 7/2011 | Brodowski |
| 2014/0315162 A1 | 10/2014 | Ehrenkranz |
| 2014/0367466 A1* | 12/2014 | Pai ..................... G06Q 30/0641 235/383 |
| 2015/0041616 A1* | 2/2015 | Gentile ............... G06Q 10/087 248/550 |
| 2015/0059290 A1 | 3/2015 | Ewert et al. |

FOREIGN PATENT DOCUMENTS

| | | |
|---|---|---|
| CN | 104636856 A | 5/2015 |
| CN | 105091499 A | 11/2015 |
| CN | 105547915 A | 5/2016 |
| GB | 2269021 A | 1/1994 |
| KR | 20080106992 A | 12/2008 |

OTHER PUBLICATIONS

Benjamin, "Using the iPhone 6s 3D Touch display to weigh items [Video]", iDownloadBlog.com, Oct. 24, 2015, 8 pages.
Non-Final Office Action dated Sep. 21, 2018, for U.S. Appl. No. 15/783,189, filed Oct. 13, 2017, 12 pages.
Amendment filed Oct. 3, 2018, for U.S. Appl. No. 15/783,189, filed Oct. 13, 2017, 12 pages.

* cited by examiner

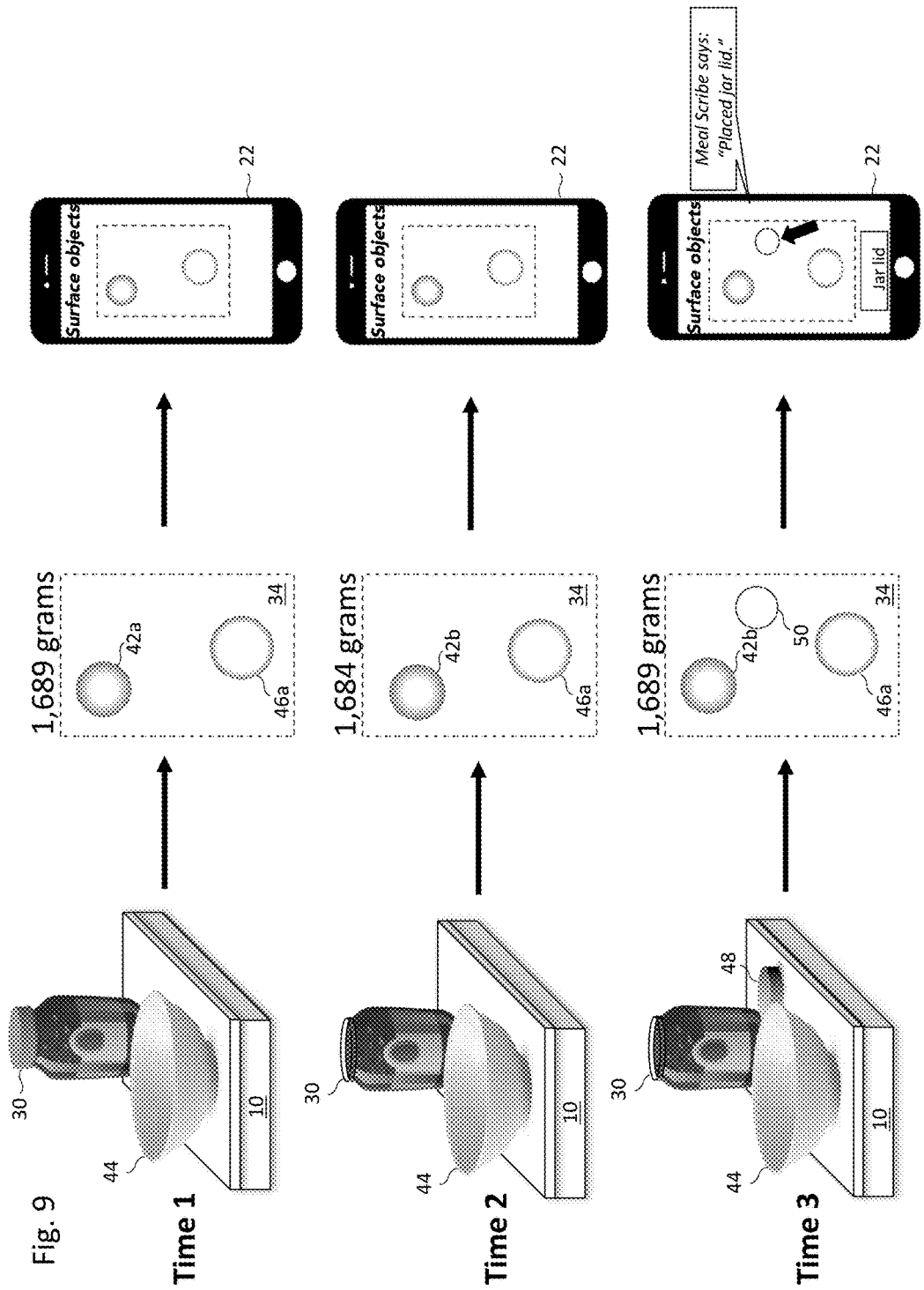

MEAL LIFECYCLE MANAGEMENT SYSTEM

RELATED APPLICATIONS

This application is a non-provisional patent application of and claims priority to U.S. Provisional Application No. 62/409,362, filed 17 Oct. 2016, and U.S. Provisional Application No. 62/416,062, filed 1 Nov. 2016, both of which are incorporated by reference herein.

FIELD OF THE INVENTION

The present invention relates to methods and systems for tracking various stages of a meal lifecycle, including one or more of meal preparation, the serving and consumption of a meal, point tracking for diet plans, use of leftovers, integration with fitness measures, management of food inventory, and food purchasing.

BACKGROUND

Individuals who are conscious about their diet often wish to measure the attributes of the foods they eat. When preparing a meal, which may be a combination of many ingredients, a process of accounting for the amount and nutritional composition of each of the ingredients can easily become complex and interfere with the joy of meal preparation. For instance, while one could in theory weigh each ingredient of a recipe, determine the nutritional composition of each ingredient (e.g., grams of carbohydrates, grams of protein, etc.), and then calculate the nutritional composition of the entire recipe, most if not all individuals would find such a process to be too cumbersome to be repeated on a daily basis.

Described hereinbelow is a meal lifecycle management system which provides techniques to track various stages of a meal lifecycle, and at the same time, minimizes the amount of overhead imposed on an individual's normal routine for preparing and consuming a meal.

SUMMARY OF THE INVENTION

In accordance with one embodiment of the invention, a pressure-sensitive device is used to measure the weight and/or footprint of a food item. A food item may generally refer to a packaged food item (e.g., a carton of milk, a jar of peanut butter, a bottle of water, a can of tomatoes, a bag of protein powder, a bottle of wine), an unpackaged food item (e.g., eggs, meat, carrots, cucumbers, melons, fruits, vegetables), and the contents within a packaged food item (e.g., milk, peanut butter, water, tomatoes, protein powder, wine). A pressure-sensitive device may be constructed from a pressure-sensitive pad (for measuring a footprint of a food item) layered over a food scale (for measuring the weight of the food item). A pressure-sensitive pad may more specifically measure the footprint shape (i.e., an outline of the footprint), a footprint pressure distribution (i.e., a two-dimensional array of pressure measurements within the footprint) and/or a footprint location (i.e., a location of the footprint on the pressure-sensitive device). Alternatively, a pressure-sensitive device may be constructed from a pressure-sensitive pad with weight sensitivity. In such a pressure-sensitive pad, weight may be determined by the pressure-sensitive device by integrating a footprint pressure distribution of the food item over the footprint of the food item. Alternatively, a pressure-sensitive device may be constructed from a pressure-sensitive pad without weight sensitivity. In such a pressure-sensitive pad, the pressure-sensitive pad may only measure a footprint pressure distribution of the food item, and the weight of the food item may be determined by a computing device external to the pressure-sensitive pad by integrating the footprint pressure distribution.

Based on the weight and footprint of a food item, a computing device may be able to lookup the identity of the food item from a food library. A local food library including a registry of food items known to be present in an individual's refrigerator or pantry may be searched first, followed by a global food library including a registry of food items in a grocery store. Each food item may be stored with a plurality of footprints (e.g., corresponding to the food item in a right-side-up, up-side-down, and/or side orientation), such that a food item may be identified regardless of its orientation on the pressure-sensitive device. Containers (e.g., plates, cups, bowls, pots, pans) may similarly be identified by their respective weight and footprint.

Techniques are provided to register each elemental step of a meal preparation process. Such elemental steps include moving a food item from one location to another, orienting a food item on a surface (e.g., right-side-up, upside down, side orientations), opening a container, transferring a food item from one container to another, transferring a food item into a container, transferring a portion of a food item into a container, transferring a portion of a food item from a container to a food item resting on the pressure-sensitive device, transferring a portion of a food item resting on the pressure-sensitive device to another food item resting on the pressure-sensitive device, transferring a food item from a cutting board into a bowl, cutting a food item on a cutting board, transferring a food item from a bowl into a pot, transferring a food item from the pot into a serving bowl, portioning a food item from a serving bowl into plates/bowls, etc. Such techniques may be combined with one another to track an entire meal preparation process. Techniques to register how much is consumed, what is consumed and by which individual are also described.

Importantly, the techniques described hereinbelow incur a minimum of user overhead (i.e., minimizes the number of steps an individual needs to perform in addition to his/her typical routine for preparing and/or consuming a meal). Indeed, some aspects may actually make the meal preparation process more efficient than a conventional process by removing the need for measuring spoons, measuring cups, etc., since the weight of an ingredient can be automatically measured and automatically converted into a quantity of an ingredient (e.g., cup of water, teaspoon of sugar, etc.).

These and other embodiments of the invention are more fully described in association with the drawings below.

BRIEF DESCRIPTION OF THE DRAWINGS

FIG. 9 depicts a cover (e.g., a lid) being removed from a container, and the computing device recognizing that the cover has been removed from the container, in accordance with one embodiment of the invention.

DETAILED DESCRIPTION OF THE INVENTION

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. Descriptions associated with any one of the figures may be applied to different figures containing like or similar components/steps. While the sequence diagrams each present a series of steps in a certain order, the order of some of the steps may be changed.

Figure 1A:
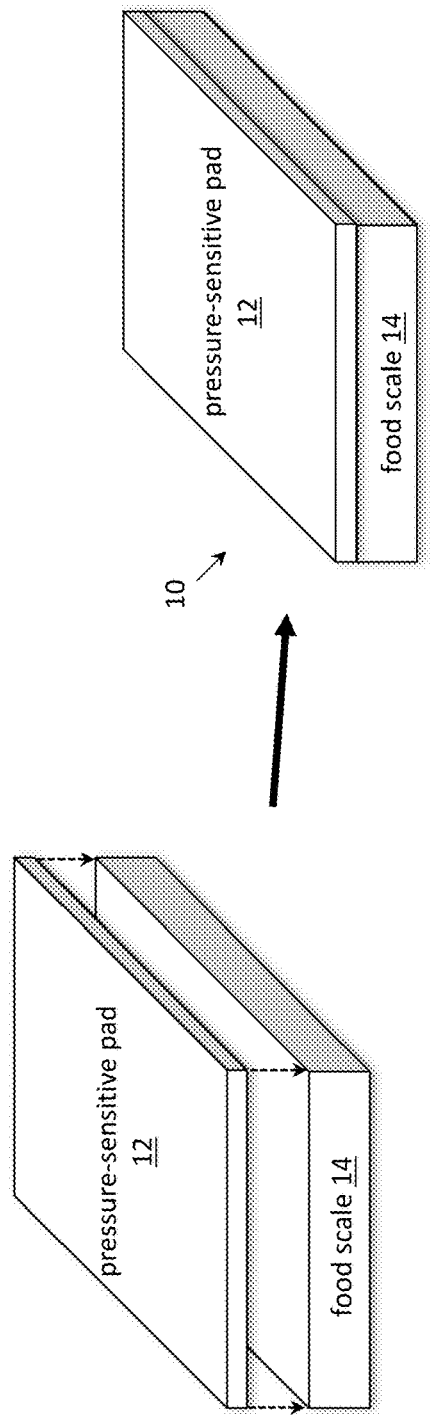
FIG. 1A depicts a pressure-sensitive device comprising a pressure-sensitive pad and a food scale.

FIG. 1A depicts pressure-sensitive device 10 which may include pressure-sensitive pad 12 attached to a top surface of food scale 14. Pressure-sensitive pad 12 may measure a "footprint" of an object (not depicted) resting on a top surface of pressure-sensitive pad 12 (i.e., the "footprint" referring to a region on pressure-sensitive pad 12 which contacts the object). More specifically, pressure-sensitive pad 12 may include an array of pressure sensors (e.g., an array of sensels) arranged over the surface of the pressure-sensitive pad, and such array of pressure sensors may measure a footprint shape (i.e., an outline of the footprint), a footprint pressure distribution (i.e., a two-dimensional array of pressure measurements within the footprint) and/or a footprint location (i.e., a location of the footprint on the pressure-sensitive device 10). An example pressure-sensitive pad may be a Sensel Morph™ manufactured by Sensel Inc.™ of Mountain View, Calif.

Food scale 14 may measure the weight of the object resting on pressure-sensitive pad 12. An example food scale may be a ReFleX Wireless Bluetooth Smart Food Scale™ manufactured by ReFleX Wireless Inc.™ of Vancouver, BC, Canada. Pressure-sensitive pad 12 may be communicatively coupled to food scale 14, such that an object's footprint may be transmitted from pressure-sensitive pad 12 to food scale 14, and/or the weight of the object resting on pressure-sensitive pad 12 may be transmitted from food scale 14 to pressure-sensitive pad 12.

Figure 1C:
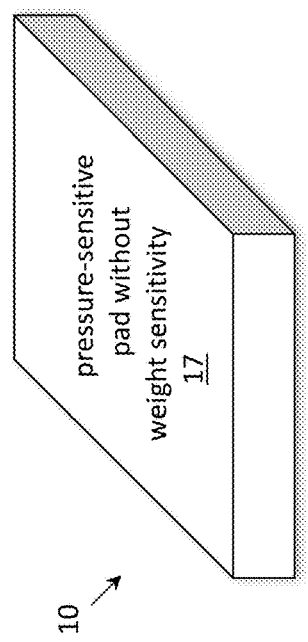
FIG. 1C depicts a pressure-sensitive device comprising a pressure-sensitive pad without weight sensitivity.
Figure 1B:
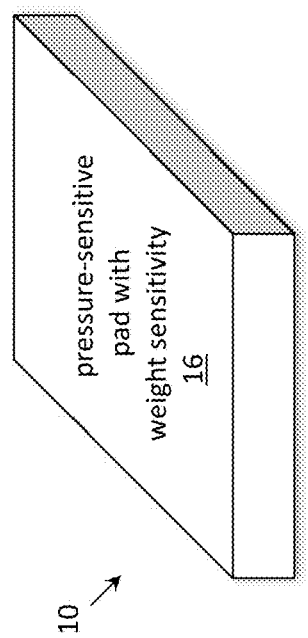
FIG. 1B depicts a pressure-sensitive device comprising a pressure-sensitive pad with weight sensitivity.

FIG. 1B depicts pressure-sensitive device 10 which may include a pressure-sensitive pad 16 with weight sensitivity. Similar to pressure-sensitive pad 12, pressure-sensitive pad 16 may include an array of pressure sensors arranged over the surface of the pressure-sensitive pad, and such array of pressure sensors may measure a footprint shape, a footprint pressure distribution and/or a footprint location. Pressure-sensitive pad 16 may be similar in construction to pressure-sensitive pad 12, except that pressure-sensitive pad 16 may be more sensitive to pressure than pressure-sensitive pad 12. To obtain a weight of an object, pressure-sensitive pad 16 may integrate the footprint pressure distribution over the footprint (i.e., weight=∬pressuredistribution(x,y)dxdy). Because the indicated integration causes any pressure sensor noise to compound, the use of pressure to derive weight may require pressure-sensitive pad 16 to be more sensitive than pressure-sensitive pad 12 (e.g., measure pressure with more accuracy).

FIG. 1C depicts pressure-sensitive device 10 which may include a pressure-sensitive pad 16 without weight sensitivity. Pressure-sensitive pad 17 may be similar in construction to pressure-sensitive pad 12. Similar to pressure-sensitive pad 12, pressure-sensitive pad 17 may include an array of pressure sensors arranged over the surface of the pressure-sensitive pad, and such array of pressure sensors may measure a footprint shape, a footprint pressure distribution and/or a footprint location. Pressure-sensitive pad 17 may be similar in construction to pressure-sensitive pad 12. Even if pressure-sensitive pad 17 does not generate a weight measurement, a computing device external from pressure-sensitive pad 17 (such as computing device 22 described below) may receive a footprint pressure distribution from pressure-sensitive pad 17 and such computing device could compute the weight of an object from the footprint pressure distribution based on the relationship weight=∬pressuredistribution(x,y)dxdy.

Figure 2:
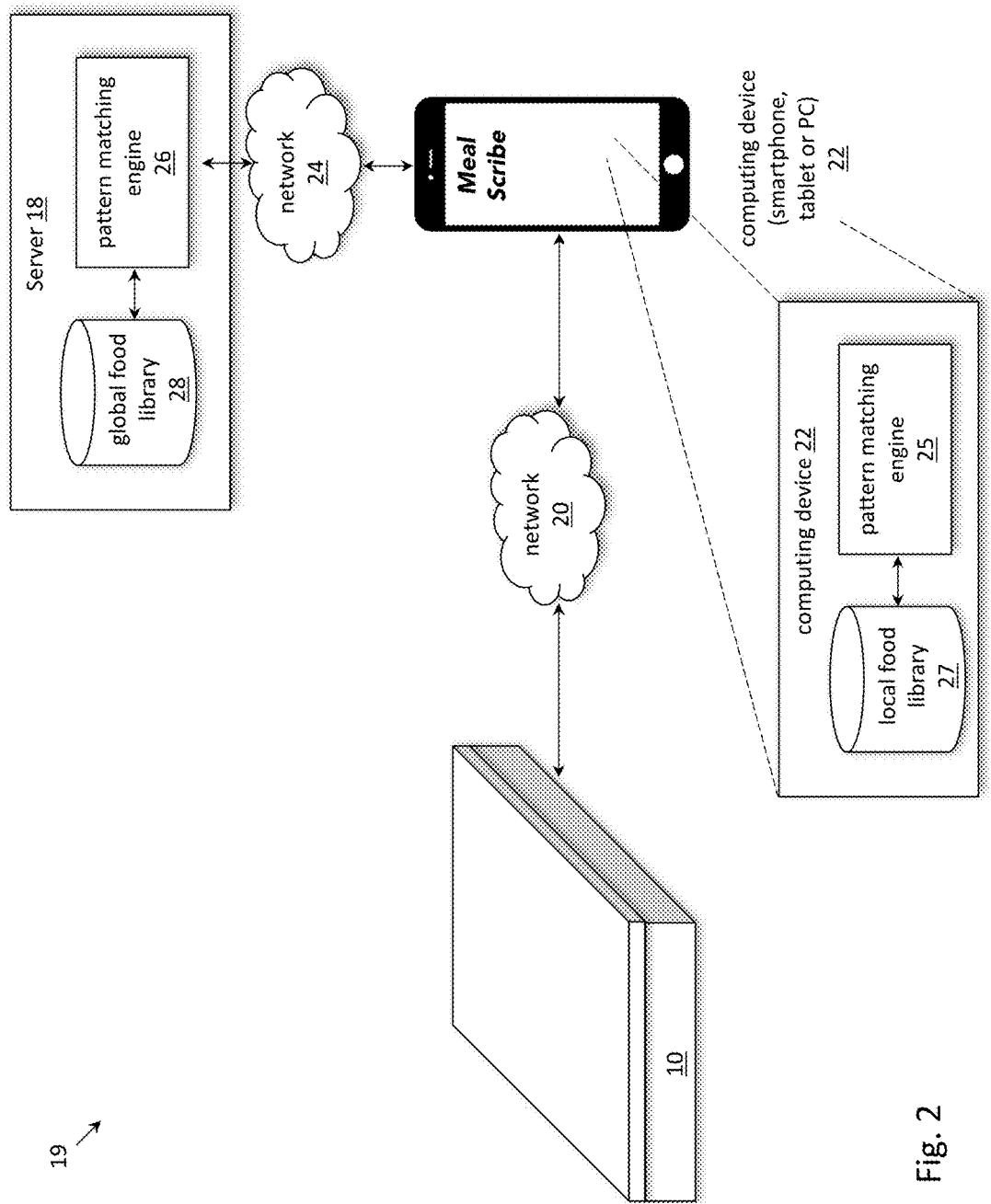
FIG. 2 depicts a meal accounting system, in accordance with one embodiment of the invention.

FIG. 2 depicts meal accounting system 19, in accordance with one embodiment of the invention. Meal accounting system 19 may include computing device 22 communicatively coupled to pressure-sensitive device 10 via network 20. Computing device 22 may be a smartphone, tablet, laptop, personal computer, or any other computing device that the user interacts with during a meal preparation process. Network 20 may comprise any form of electronic communications link(s) and, in some cases, may be individual communications links, or one or more communications networks (e.g., computer networks), including private networks, public networks and/or virtual private networks over public networks. Data may be transmitted wirelessly or via wired means over network 20. While FIG. 2 depicts the pressure-sensitive device of FIG. 1A, it is understood that the pressure-sensitive device of FIG. 1B, FIG. 1C or another pressure-sensitive device may be employed instead of the pressure-sensitive device of FIG. 1A.

Computing device 22 may also be communicatively coupled to pattern matching engine 26 via network 24. Network 24 may similarly comprise any form of electronic communications link(s) and, in some cases, may be individual communications links, or one or more communications networks (e.g., computer networks), including private networks, public networks and/or virtual private networks over public networks. Pattern matching engine 26 may receive identifying characteristics of a food item (e.g., weight and footprint), and in response identify a food item in global food library 28 which matches the received identifying characteristics. An example of global food library 28 is the Gladson Space Management Database and Nutrition Database™. Global food library 28 could also be crowd-sourced. As more people use the meal accounting system and more food items are registered, the food items could be added to a common global food library for everyone to use.

Pattern matching engine 26 and global food library 28 may be instantiated within server 18. In addition or in the alternative, pattern matching engine 25 and local food library 27 may be instantiated locally within computing device 22. Local food library 27 may store food identifiers and characteristics corresponding to food registered by the user (e.g., user purchases food items from grocery store and registers the food items with computing device 22 before placing the food into the refrigerator or pantry), whereas global food library 28 may store food identifiers and characteristics corresponding to general food items (e.g., any food item present in a grocery store). The pattern matching engines and food libraries are described in greater detail below in FIGS. 3 and 4.

In another embodiment of the invention (not depicted), the functionality and/or components of computing device 22 may be integrated into pressure-sensitive device 10 (e.g., computing device 22 may be part of pressure-sensitive device 10). In such an embodiment, pressure-sensitive device 10 may include a touch screen, speaker, microphone, keypad, and/or other user interface which allow a user to interact with pressure-sensitive device 10 in a manner similar to how a user would interact with computing device 10.

Figure 3:
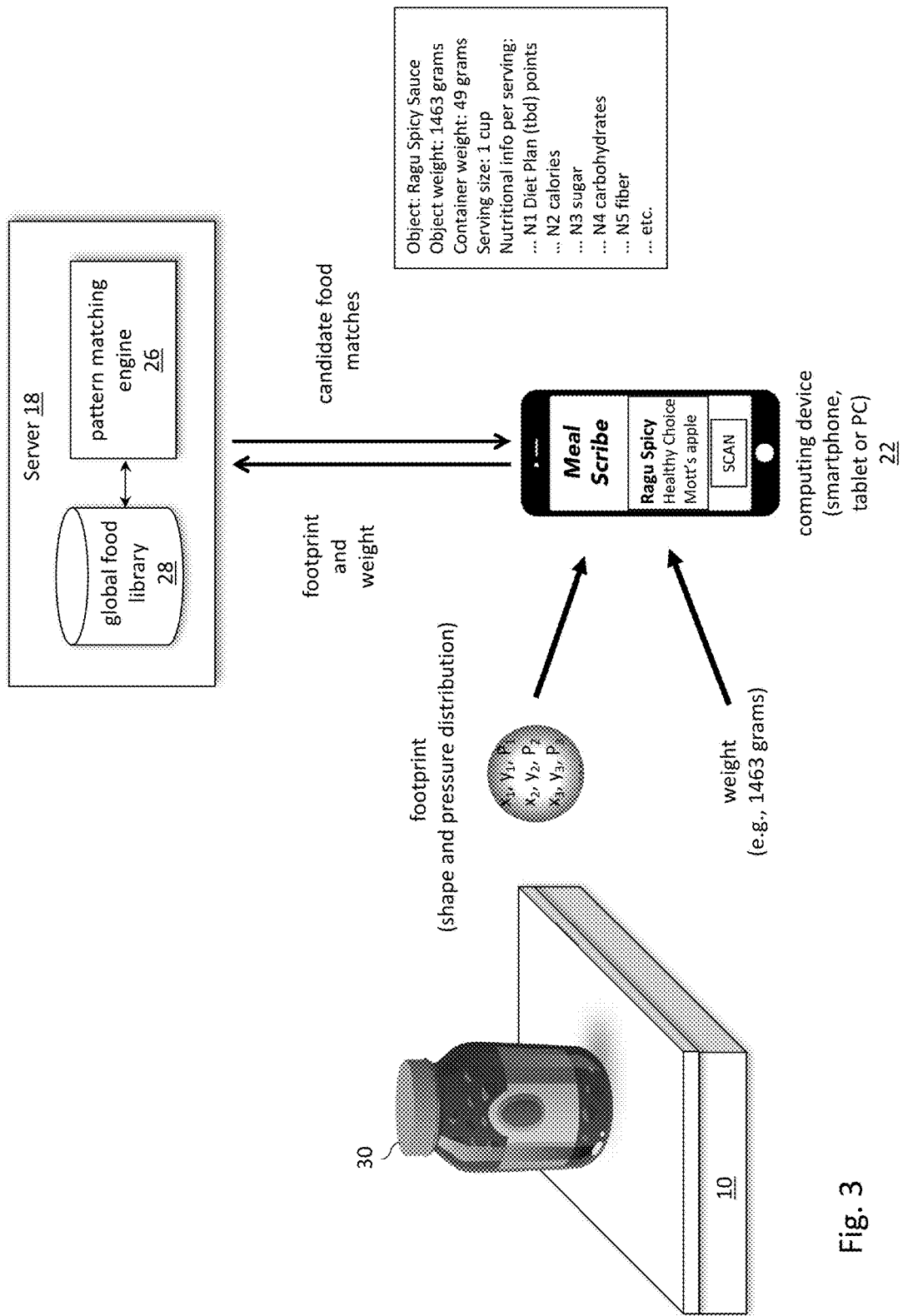
FIG. 3 provides an example of a process for determining an identity of a food item resting on the pressure-sensitive device, in accordance with one embodiment of the invention.

FIG. 3 provides an example of a process for determining an identity of food item 30 resting on pressure-sensitive device 10 (or more precisely, determining an identity of the food item contained within container 30). Pressure-sensitive device 10 may transmit a footprint (e.g., including the footprint shape and footprint pressure distribution) and a weight of an unidentified food item 30 to computing device 22. If not already apparent, $P_1$ represents the pressure measurement at location $(x_1, y_1)$; $P_2$ represents the pressure measurement at location $(x_2, y_2)$; and so on. Locations $(x_1, y_1)$, $(x_2, y_2)$, . . . are locations within the footprint of the object. In the instant example, unidentified food item 30 weighs 1463 grams. In another embodiment using the pressure-sensitive device of FIG. 1C, pressure-sensitive device 10 may transmit only the footprint of food item 30 to computing device 22, and computing device 22 may compute the weight of the food item based on the footprint (e.g., by integrating the footprint pressure distribution over the footprint).

Pattern matching engine 25 may first check local food library 27 for a food item that matches the received footprint and weight. In many instances, local food library 27 of registered items will contain a match for the received footprint and weight, but if not, computing device 22 may consult global food library 28. If a definitive "best" match is identified from either global food library 28 or local food library 27, computing device 22 may notify the user of the identified best match (e.g., displaying the matching food item on a display of the computing device, speaking the matching food item using a microphone of the computing device). If a definitive "best" match is identified by computing device 22, no user action is needed to identify the food item other than placing the food item on pressure-sensitive device 10.

If more than one close match is identified, the user may perform one or more simple steps to provide the identity of food item 30 to computing device 22. For example, the user can select the food item from a list of candidate food matches displayed on computing device 22 (e.g., select Ragu Spicy . . . from a list containing Ragu Spicy . . . , Healthy Choice . . . , Mott's apple . . . ), speak the food name to computing device 22, or as a fallback option and if the food item contains packaging, scan a universal product code (UPC) on the packaging. In response to being provided the identity of food item 30, computing device 22 may store an association between the identity, weight and footprint of food item 30 so that food item 30 may be promptly recognized without user interaction when placed on a surface of pressure-sensitive device 10 at a later point in time. In another embodiment (not depicted in the instant figure), if more than one close match is identified, the user may also reorient food item 30 on pressure-sensitive device 10 (e.g., flipping the food item), in order to provide an additional footprint of food item 30 to computing device 22. The additional footprint may be used to narrow down the multiple close matches to the best match.

If there are no matches, the user may manually input the identity of the food item (e.g., using a touchscreen of computing device, speaking the name of the food item to computing device, etc.). Once again, in response to being provided the identity of food item 30, computing device 22 may store an association between the identity, weight and footprint of food item 30 so that food item 30 may be promptly recognized when placed on a surface of pressure-sensitive device 10 at a later point in time without user interaction.

The now identified food item may be associated with a weight of a container which contains the food item (i.e., allowing future determination of the depletion of the food item), and/or may be associated with nutrition data of the food item (e.g., N2 calories, N3 sugar, . . . , in which N2, N3 are placeholder for numbers). Such data may be maintained with a meal record that records the ingredients that are present in a meal.

Figure 4:
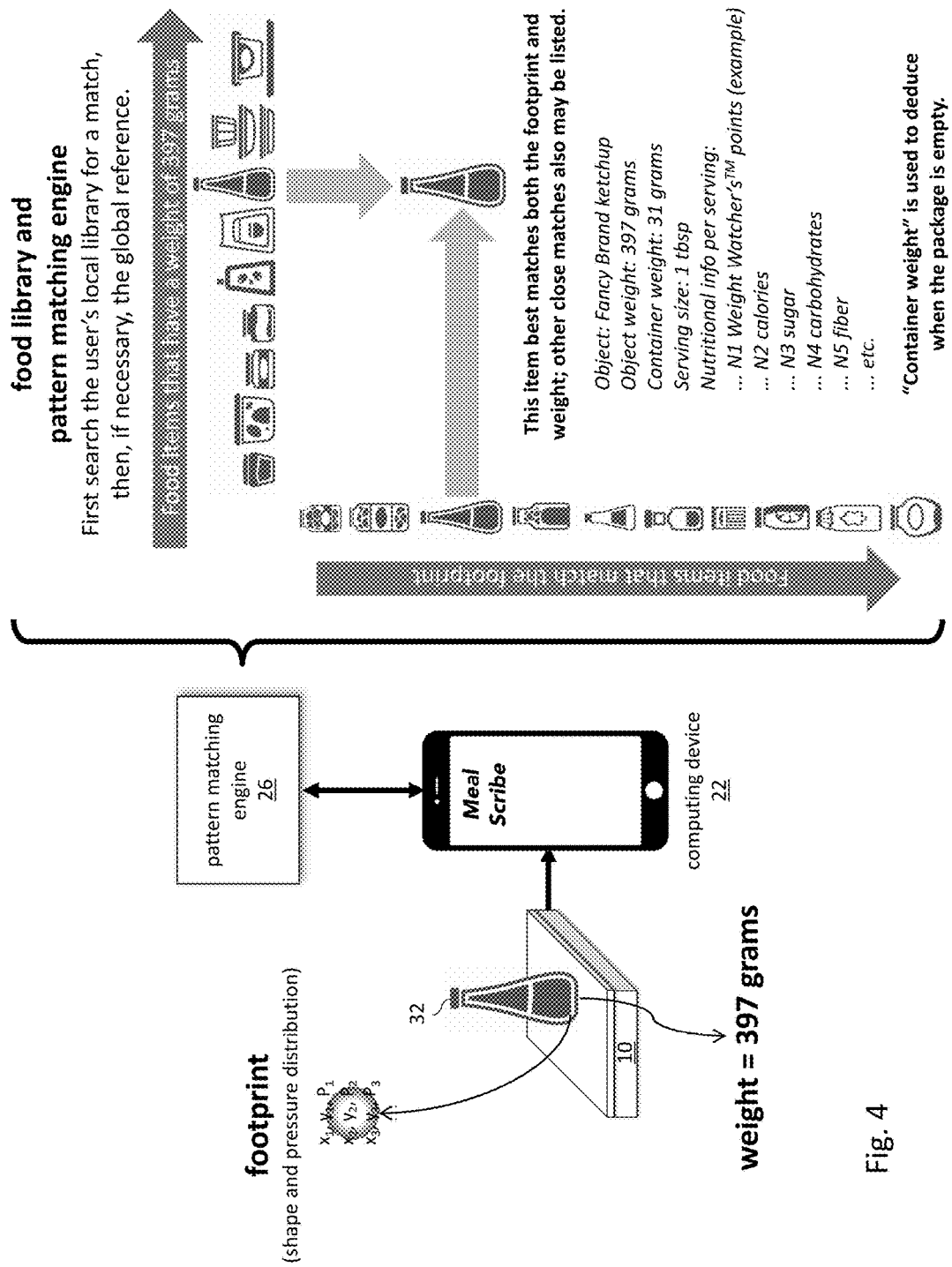
FIG. 4 provides an example of a table-lookup process for determining an identity of a food item resting on the pressure-sensitive device, in accordance with one embodiment of the invention.

FIG. 4 provides an example of a table-lookup process for determining an identity of food item 32 resting on pressure-sensitive device 10. In the example of FIG. 4, pressure-sensitive device 10 determines the weight of food item 32 to be 397 grams. Such weight and a footprint (e.g., including footprint shape and footprint pressure distribution) of food item 32 may be transmitted to computing device 22. A food item which matches the weight and footprint may first be searched in local food library 27, and if necessary further searching global food library 28. As depicted in FIG. 4, food items with a footprint which substantially matches the footprint of the food item 32 may be identified. More specifically, two footprints may be considered to substantially match based on pattern recognition techniques. Such pattern recognition techniques are known in the art, and will not be described in further detail for conciseness.

Additionally, food items having a weight that substantially matches the weight of the food item 32 may be identified. In one embodiment, two weights may be considered to substantially match if the difference between the two weights is less than 5% (or other percentage) of either of the weights. If a food item from the (local or global) food library substantially matches both the weight and footprint of the food item 32, food item 32 may be identified as the food item from the food library.

Figure 5:
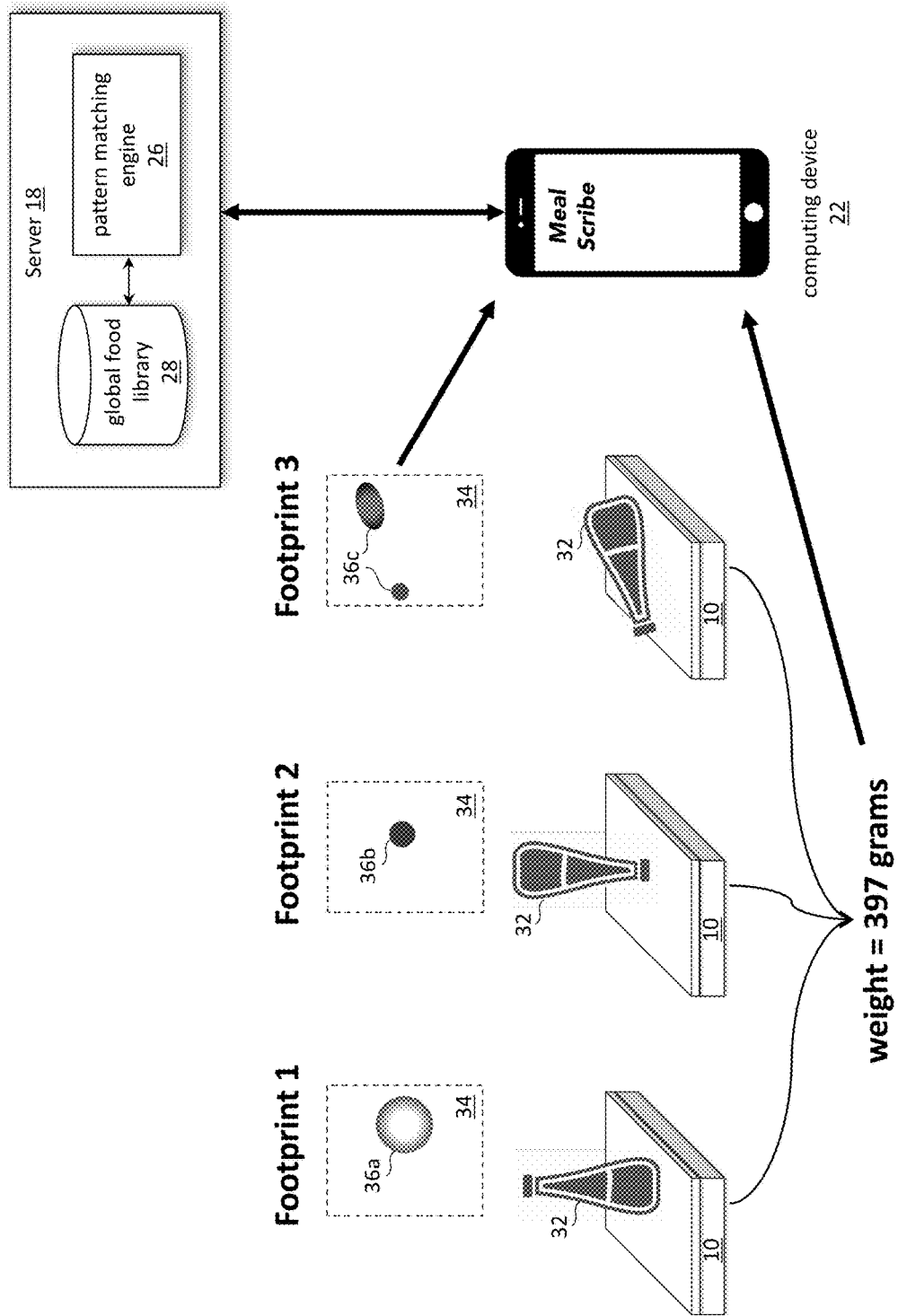
FIG. 5 depicts various orientations of a container resting on the pressure-sensitive device, and a process for associating a plurality of footprints (each footprint corresponding to a different orientation of the container on the pressure-sensitive device) with an identity of the food item contained within the container, in accordance with one embodiment of the invention.

FIG. 5 depicts various orientations of food item 32 resting on pressure-sensitive device 10 (or more precisely, various orientations of container 32 resting on pressure-sensitive device 10, the container containing a food item). As shown, each orientation of food item 32 may result in a different footprint of the food item. The food item 32, when oriented on its base, may generate footprint 36a; the food item 32, when oriented on it top, may generate footprint 36b; and the food item 32, when oriented on its side, may generate footprint 36c. It is noted that a footprint, such as footprint 36c, may comprise non-contiguous contact areas between food item 32 and pressure-sensitive device 10. Further details regarding how computing system 22 may determine whether two or more footprints belong to a single food item (i.e., is a footprint that comprises non-contiguous contact areas) or belong to two or more distinct food items is described below in FIG. 32. When an object is associated with a plurality of footprints, one of the footprints (e.g., footprint 36a corresponding the "right side up" orientation) may be designated as the "default" or "nominal" footprint. As depicted in the registration process of FIG. 5, a plurality of footprints (e.g., 36a, 36b and 36c) may be transmitted to computing device 22 (and optionally the weight of the food item), and the computing device may associate the plurality of footprints (and optionally the weight) with an identifier of the food item (e.g., ketchup) in the global or local food library. As such, subsequent to the registration process depicted in FIG. 5, one or more of the plurality of footprints and/or the weight may be used to identify the food item.

In FIG. 5, each of the footprints (36a, 36b, 36c) are depicted within a rectangular box 34 representing an outline of the surface of pressure-sensitive device 10. As such, the footprint in association with rectangular box 34 may convey the location of the food item on the surface of pressure-sensitive device 10. If not already apparent, a darker color is used to represent a higher pressure, whereas a lighter color is used to represent a lower pressure.

Figure 6:
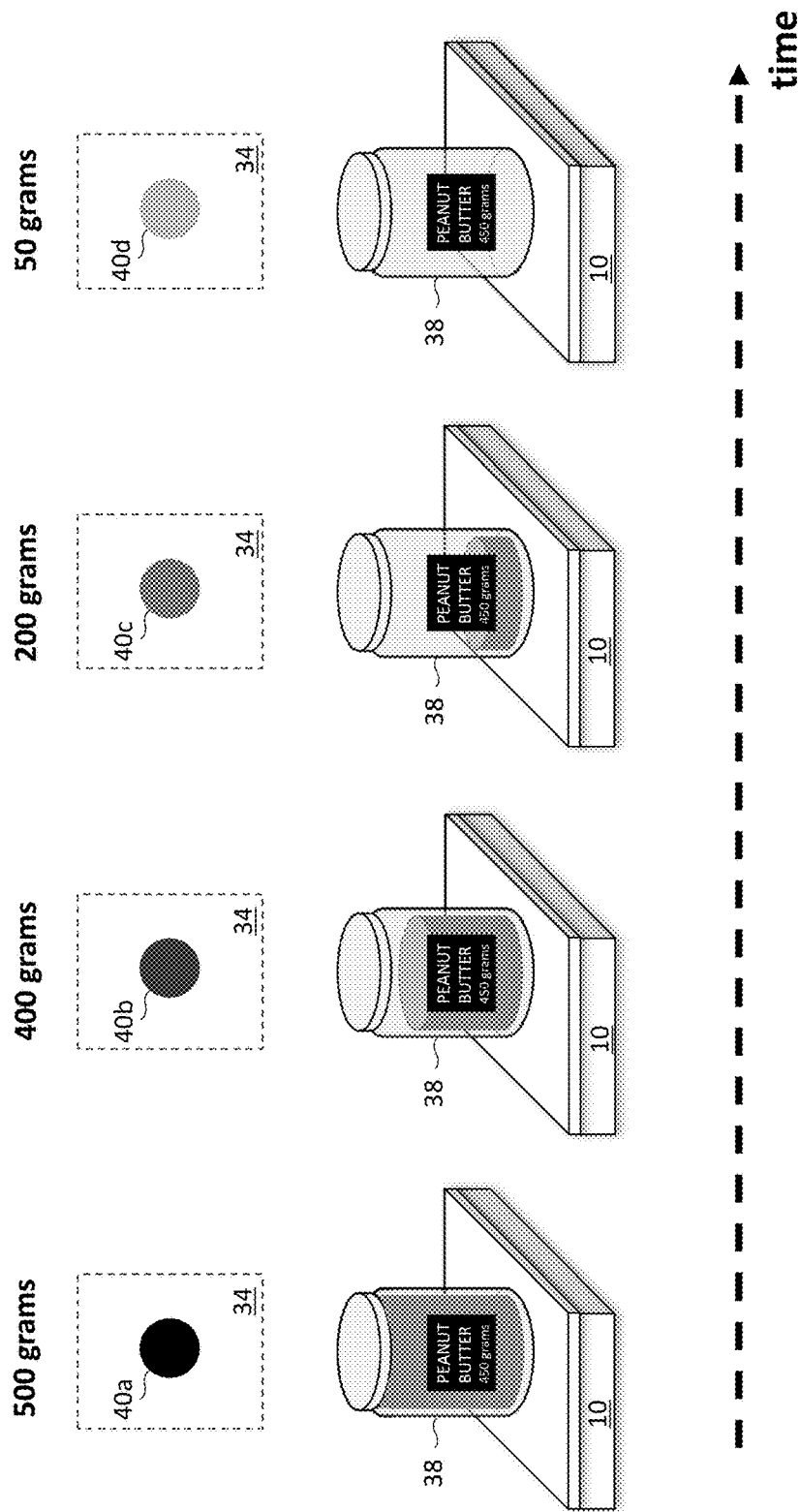
FIG. 6 depicts a container resting on the pressure-sensitive device and measurements generated by the pressure-sensitive device as a food item is depleted within the container, in accordance with one embodiment of the invention.

FIG. 6 depicts container 38 resting on pressure-sensitive device 10 and measurements generated by pressure-sensitive device 10 as a food item is depleted within container 38. Upon determining the footprint shape (i.e., outline of 40a, 40b, 40c and 40d) to be constant throughout the measurements, computing device 22 (not depicted) may determine the measurements to all correspond to the same container, rather than four distinct containers. Based on the decreasing weight (e.g., 500 grams, 400 grams, 200 grams, 50 grams), computing device 22 may further determine the decreasing weight to be caused by the contents of the container being depleted over time. In the present example, 500 grams corresponds to the weight of container 38 when it is full (e.g., with peanut butter) and 50 grams correspond to the weight of container 38 when its contents have been completely depleted.

FIG. 7 through FIG. 15B describe elemental steps of a meal preparation process (i.e., the building blocks of a meal preparation process), and techniques for automatically registering each of these elemental steps. It is understood that the preparation of an entire meal may involve a combination of these elemental steps, and as such the techniques for automatically registering each of the elemental steps may be used in combination to track (i.e., account for amount and type of ingredients) the entire meal preparation process.

Figure 7:
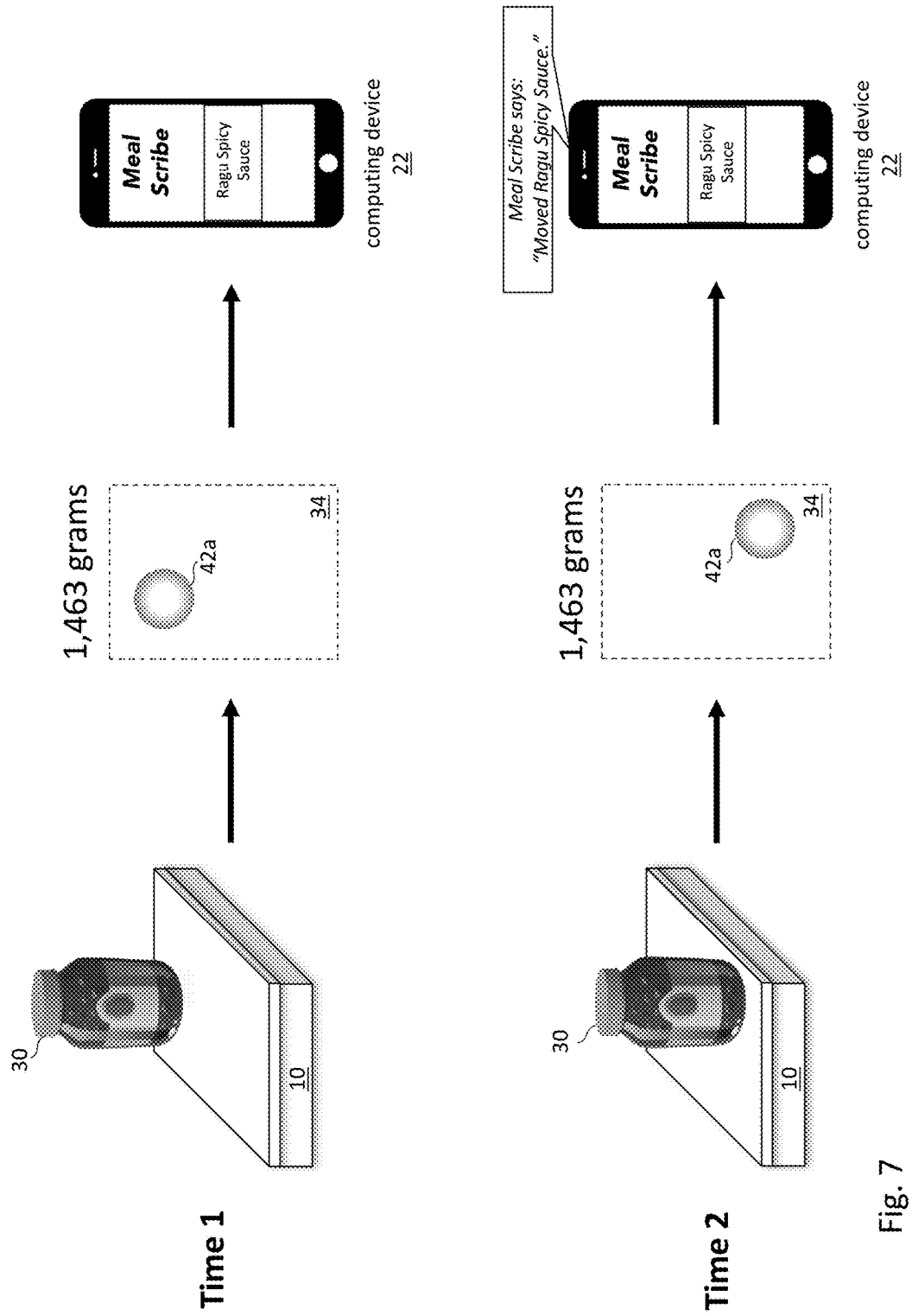
FIG. 7 depicts a container being repositioned (e.g., picked up and moved) over the surface of the pressure-sensitive device and the computing device detecting the movement of the container, in accordance with one embodiment of the invention.

FIG. 7 depicts container 30 being repositioned (e.g., picked up and moved) over the surface of pressure-sensitive device 10 and computing device 22 detecting the movement of container 30. More specifically, at a first time instance, computing device 22 may receive footprint 42a (e.g., including footprint shape, footprint pressure distribution and footprint location) and the weight of container 30 from pressure-sensitive device 10. Based on the footprint and weight, computing device 22 may identify the identity of container 30 to be a jar of Ragu spicy sauce (following a procedure similar to FIGS. 3 and 4). After the first time instance and before a second time instance, computing device 22 may detect the disappearance of footprint 42a (not depicted).

At the second time instance, computing device 22 may again receive the footprint (e.g., including footprint shape, footprint pressure distribution and footprint location) and weight of container 30 from pressure-sensitive device 10. Upon determining the weight of container 30 to be constant (e.g., both time instances measuring 1,463 grams), the footprint outline and pressure distribution to be constant, but the footprint locations to be different, computing device 22 may determine (i.e., infer) that container 30 was moved over the surface of pressure-sensitive device 10. The user may be informed of computing device 22 recognizing the movement of container 30 (e.g., computing device 22 speaking "Moved Ragu Spicy Sauce", displaying "Moved Ragu Spicy Sauce" on display, etc.). No user interaction with computing device 22 is needed unless the inference of computing device 22 is incorrect.

Figure 8:
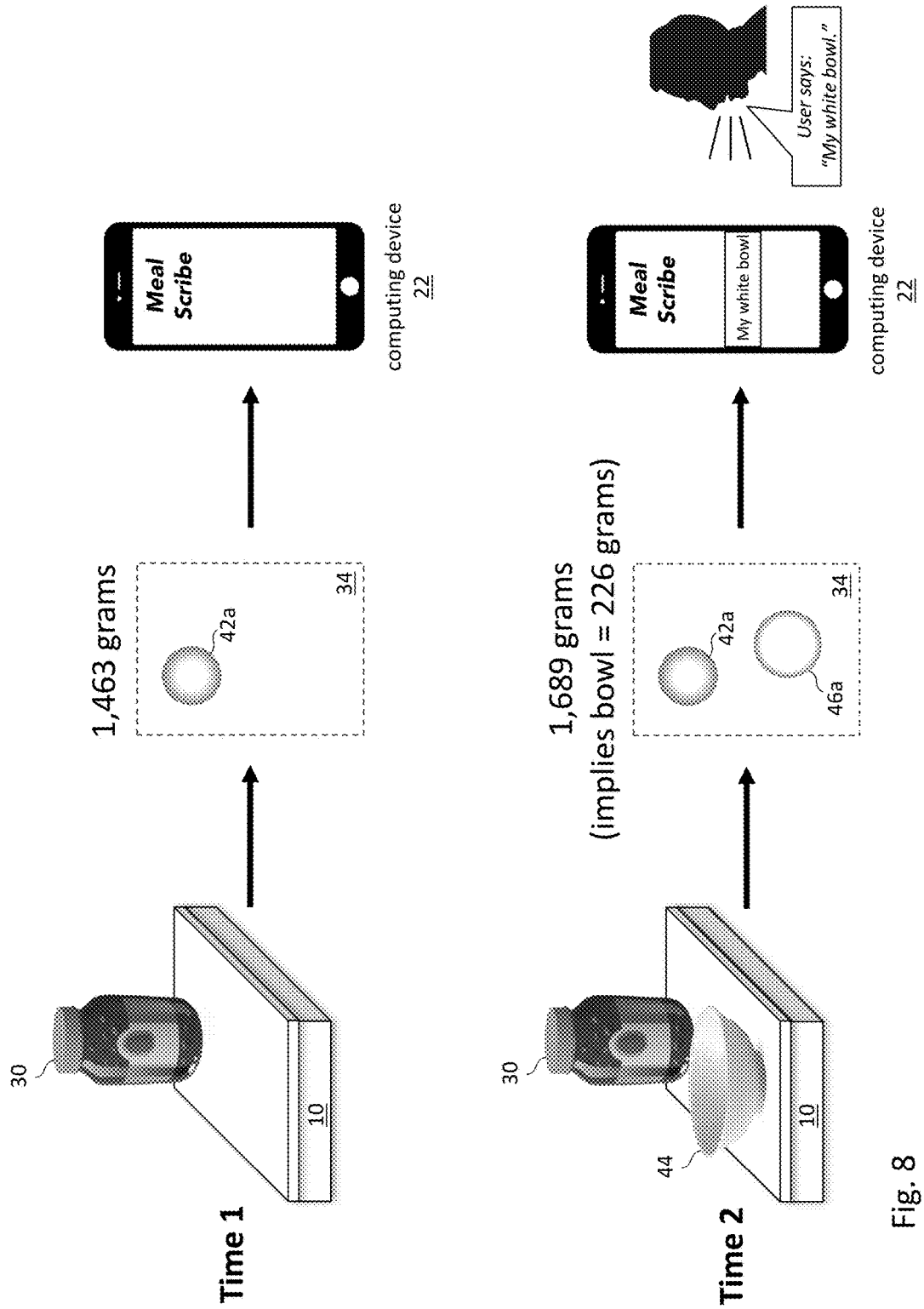
FIG. 8 depicts a container (e.g., a white bowl) being placed onto the pressure-sensitive device, and the computing device associating an identity with the container, in accordance with one embodiment of the invention.

FIG. 8 depicts container 44 (e.g., a white bowl) being placed onto pressure-sensitive device 10, and computing device 22 associating an identity of container with the container 44 if the container had not previously been registered. More specifically, at a first time instance, computing device 22 may receive footprint 42a (e.g., including footprint shape, footprint pressure distribution and footprint location) and weight of container 30 (i.e., 1,463 grams) from pressure-sensitive device 10. Based on footprint 42a and the weight, computing device 22 may identify the identity of container 30 to be a jar of Ragu spicy sauce (following a procedure similar to FIGS. 3 and 4).

At a second time instance, computing device 22 may receive two footprints (42a, 46a) and the total weight of the two objects (i.e., 1,689 grams). Based on footprint 42a being unchanged, computing device 22 can determine food item 30 to be present at both time instances. Based on the new footprint 46a, and the increase of weight (i.e., 1,689 grams− 1,463 grams=226 grams), computing device 22 may determine the weight and footprint of container 44. If container 44 had not previously been registered at computing device 22, the user may provide a custom label (e.g., "My white bowl") by, for example, typing the custom label on a touch screen of computing device 22 or speaking the custom label to a microphone of computing device 22. An association between the footprint, weight and custom label of container 44 may be stored at computing device 22 so that container 44 may be recognized when placed on a surface of pressure-sensitive device 10 at a later point in time. If not already apparent, pressure-sensitive device 10 may register any object in general (e.g., container 44, fork, knife, etc.), and not just food items.

FIG. 9 depicts cover 50 (e.g., a lid) being removed from container 30, and computing device 22 determining that cover 48 has been removed from the container 30. More specifically, at a first time instance, container 44 is positioned on pressure-sensitive device 10 along with container 30. Assume that Time 1 of FIG. 9 is equivalent to Time 2 of FIG. 8, such that computing device 22 has already registered containers 30 and 44 (e.g., knows weight of container 30 to be 1,463 grams, weight of container 44 to be 226 grams). In the embodiment depicted in FIG. 9, the footprints 42a, 46a may be depicted on a display of computing device, and the relative placement of the footprints 42a, 46a on the display may reveal the relative location of the footprints on pressure-sensitive device 10.

At a second time instance, cover 50 of container 30 having a weight of 5 g is removed from the container 30, causing the total weight of the objects to decrease from 1689 grams to 1684 grams. In order to determine whether the weight of container 30 has decreased by 5 grams or whether the weight of container 44 has decreased by 5 grams, computing device 22 may integrate the pressure distribution of footprints 42b and 46a. Upon such integration, computing device 22 may determine the weight of container 30 to be 1458 grams and the weight of container 44 to be 226 grams, concluding that the weight of container 30 has decreased by 5 grams.

At a third time instance, cover 48 is placed on the pressure-sensitive device 10, and a new object (i.e., cover 48) with footprint 50 and a weight of 5 g is registered by pressure-sensitive device 10 and, in some instances, may be shown on a display of computing device 22 (see arrow pointing out the presence of a new object). Upon determining the total weight of the container 30 and cover 48 combination (in the third time instance) equals the weight of the container 30 (in the first time instance), computing device 22 may determine that cover 48 has been removed from container 30.

Such determination may be provided to the user via, for example, an audio message or a visual representation (e.g., a textual message appearing on a display of computing device 22) in which the determination may be verified and/or corrected by the user as needed. In instances where the user does not confirm that the determination is correct, computing device 22 may prompt the user to provide further information regarding, for example, the identity of the objects on pressure-sensitive device 10 so as to, for example, account for the missing container weight and/or the appearance of the new object (e.g., cover 48) on pressure-sensitive device 10. The user may provide this information to the system via, for example, typing, speaking, scanning a UPC code, and/or taking a picture of the objects on pressure-sensitive device 10.

In some embodiments, computing device 22 may recognize and/or filter out a transient footprint and/or weight changes associated with, for example, a brief downward force applied to container 30 while cover 48 is being removed from container 30.

Figure 10A:
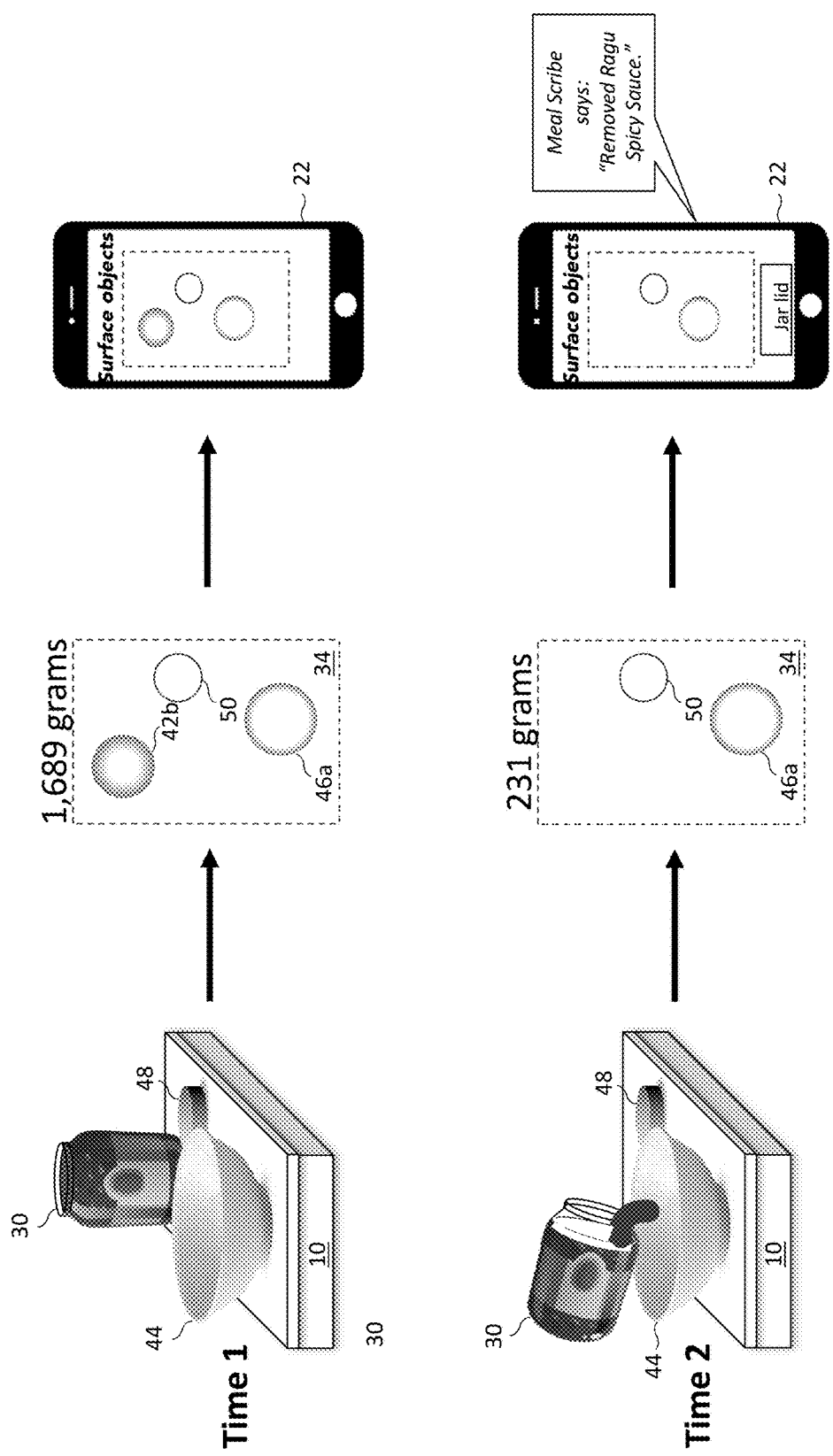
FIGS. 10A-10B depict a portion of a food item contained in a first container (e.g., a jar) being transferred into a second container (e.g., a bowl), and the computing device recognizing an amount and type of food that has been transferred into the second container, in accordance with one embodiment of the invention.
Figure 10B:
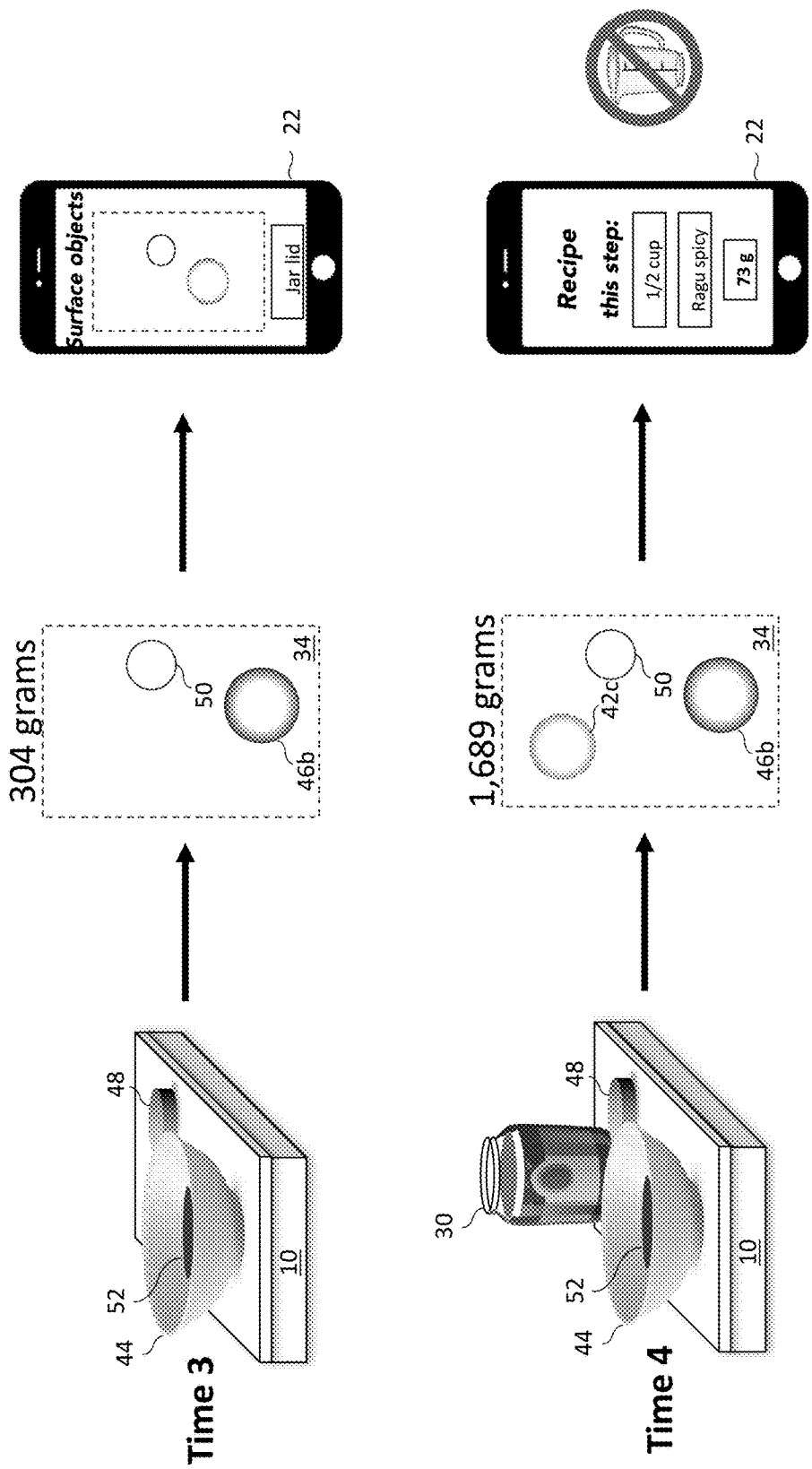

FIGS. 10A-10B depict a portion of a food item contained in container 30 (e.g., a jar) being transferred into container 44 (e.g., a bowl), and computing device 22 recognizing an amount and type of food that has been transferred into container 44. More specifically, at a first time instance, container 44 is positioned on pressure-sensitive device 10 along with container 30 and cover 48. Assume that Time 1 of FIG. 10A is equivalent to Time 3 of FIG. 9, such that computing device 22 has already registered container 30, container 44 and cover 48 (e.g., knows the weight of container 30 to be 1,458 grams, the weight of container 44 to be 226 grams and the weight of cover 48 to be 5 grams).

At a second time instance, container 30 is picked up, resulting in pressure-sensitive device providing measurements indicating the simultaneous disappearance of footprint 42b and a weight decrease (i.e., 1,689 grams–231 grams=1,458 gram) equal to the container's weight (minus the cover). In response to such measurements, computing device 22 may determine that container 30 has been removed from pressure-sensitive device 10, and may inform the user of such determination (e.g., "Removed Ragu Spicy Sauce").

At a third time instance, food 52 has been poured into container 44, causing the weight of container 44 to increase and its footprint 46b to change. Pressure-sensitive device 10 may measure the weight of the objects to be 304 grams and the footprints of the objects (46b, 50). By integrating the pressure distributions of footprints 46a and 46b, computing device 22 may determine the weight of container 44 increased by 73 grams.

At a fourth time instance, container 30 is returned to pressure-sensitive device 10. Pressure-sensitive device 10 may measure the weight of the objects to be 1,689 grams and the footprints of the objects (42c, 46b, 50). By integrating the pressure distributions of footprints 42c and 46b, computing device 22 may determine the weight of container 30 decreased by 73 grams. Based on the determinations that the weight of container 30 decreased by 73 grams and the weight of container 44 increased by 73 grams, computing device 22 may determine that 73 grams of the food item from container 30 has been transferred from container 30 to container 44.

In the current example, a decrease in the weight of container 30 was precisely equal to the increase in the weight of container 44, but the changes in weights being substantially equal to one another (e.g., substantially equal being one weight difference being within 5% or other percentage of the other weight difference) could indicate a food item being transferred from one container to another container. For example, there could be some spilling during the transferring from one container to another container, causing the weight differences to not be precisely equal to one another.

Global or local food library may further contain a conversion from weight to volume of the food item (e.g., 73 grams of Ragu spicy sauce=0.5 cup), such conversion taking into account the density of a food item. The automatic detection of the weight in conjunction of a conversion from weigh to volume may obviate the need for measuring cups or spoons.

The meal accounting system may leverage existing recipe databases. The system could guide the user through the recipe and update the progress of the meal preparation as it detects each completed recipe step. It can further notify the user if a mistake is detected, and step(s) to correct to the mistake.

Figure 11:
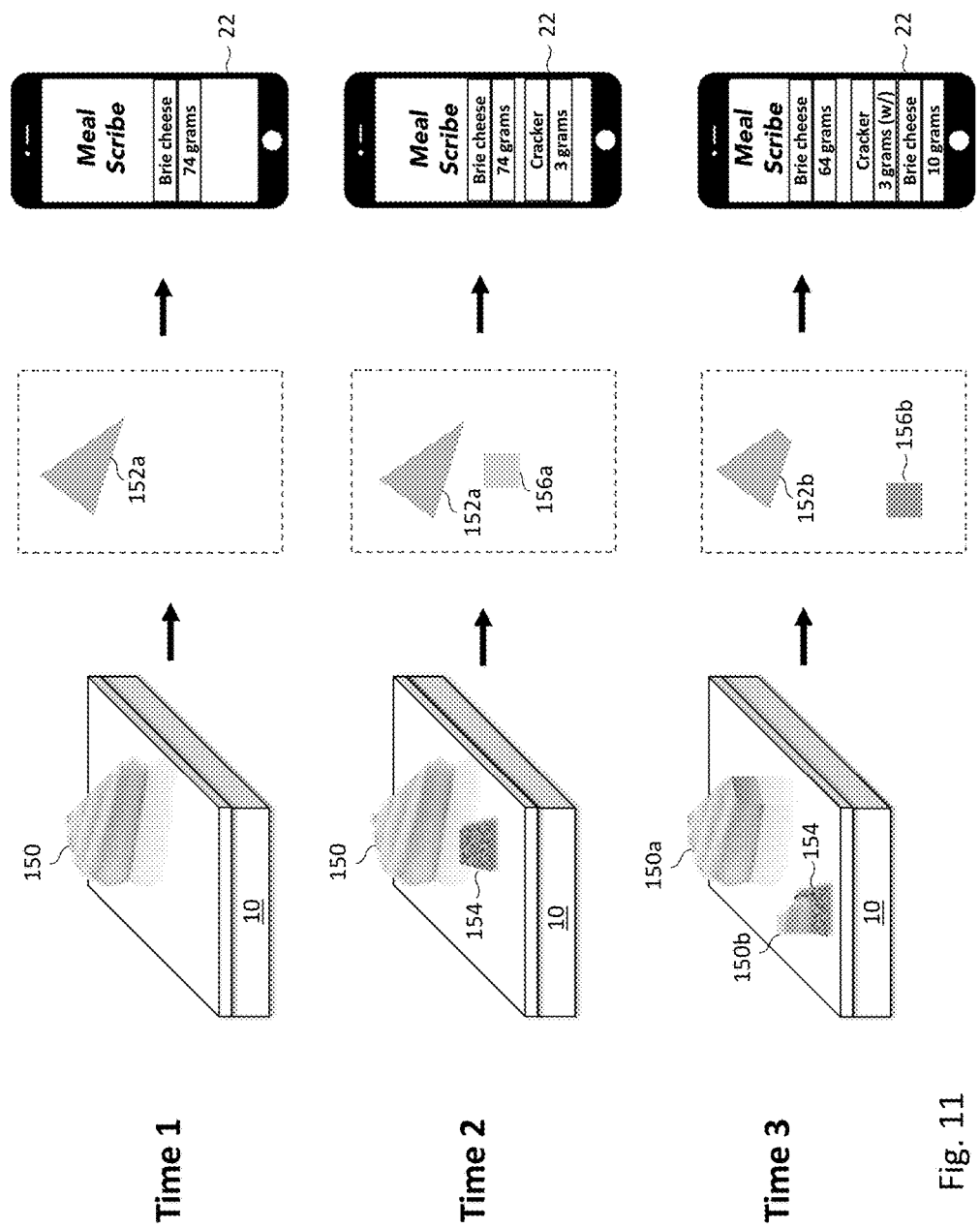
FIG. 11 depicts a portion of a food item (e.g., Brie cheese) being transferred from a first food item (e.g., block of Brie cheese) to a second food item (e.g., cracker), and the computing device recognizing an amount and type of food that has been transferred to the second food item, in accordance with one embodiment of the invention.

FIG. 11 depicts a portion of a food item (e.g., Brie cheese) being transferred from a first food item (e.g., block of Brie cheese) to a second food item (e.g., cracker), and the computing device recognizing an amount and type of food that has been transferred to the second food item, in accordance with one embodiment of the invention. More specifically, at a first time instance, first food item 150 (e.g., Brie cheese) is positioned on pressure-sensitive device 10. Pressure-sensitive device 10 may measure the weight (=74 grams) and footprint 152a of food item 150. Based on the determination of the weight and the footprint of food item 150, computing device 22 may determine that the food item is Brie cheese. The weight and the identity of food item 150 may be displayed on a display of computing device 22 (e.g., "Brie cheese weighing 74 grams").

At a second time instance, food item 154 (e.g., cracker) is additionally positioned on pressure-sensitive device 10. Pressure-sensitive device 10 may measure the weight (=3 grams) and footprint 156a of food item 154. Based on the determination of the weight and the footprint of food item 154, computing device 22 may determine that the food item is a cracker. The weight and identity of food item 154 may be displayed on a display of computing device 22 (e.g., "Cracker weighing 3 grams"), along with the weight and identity of food item 150 (e.g., "Brie cheese weighing 74 grams").

After the second time instance and before a third time instance, a portion of food item 150 may be transferred to food item 154. For example, the user may cut off a piece of the Brie using a knife and place the severed portion onto a top surface of cracker 154.

At a third time instance, portion 150b of food item 150 is located on a top surface of food item 154 (and the remaining portion of food item 150 is labeled as 150a). Pressure-sensitive device 10 may measure the weight (=64 grams) and footprint 152b of the remaining portion 150a of food item 150. Pressure-sensitive device 10 may also measure the weight (=13 grams) and footprint 156b of food item 154 in combination with portion 150b of food item. Based on the determination that the weight associated with footprint 152a decreased by 10 grams and the determination that the weight associated with footprint 156a increased by 10 grams between the second and third time instances three, computing device 22 may infer that 10 grams of food item 150 was transferred to food item 154. In other words, computing device 22 may be able to infer that footprint 156b is now associated with 10 grams of food item 150 and 3 grams of food item 154. Such determination, along with the remaining weight of food item 150, may be displayed on a display of computing device 22 (e.g., "Brie cheese weighing 64 grams", "Cracker weighing 3 grams with Brie cheese weighing 10 grams").

Figure 12:
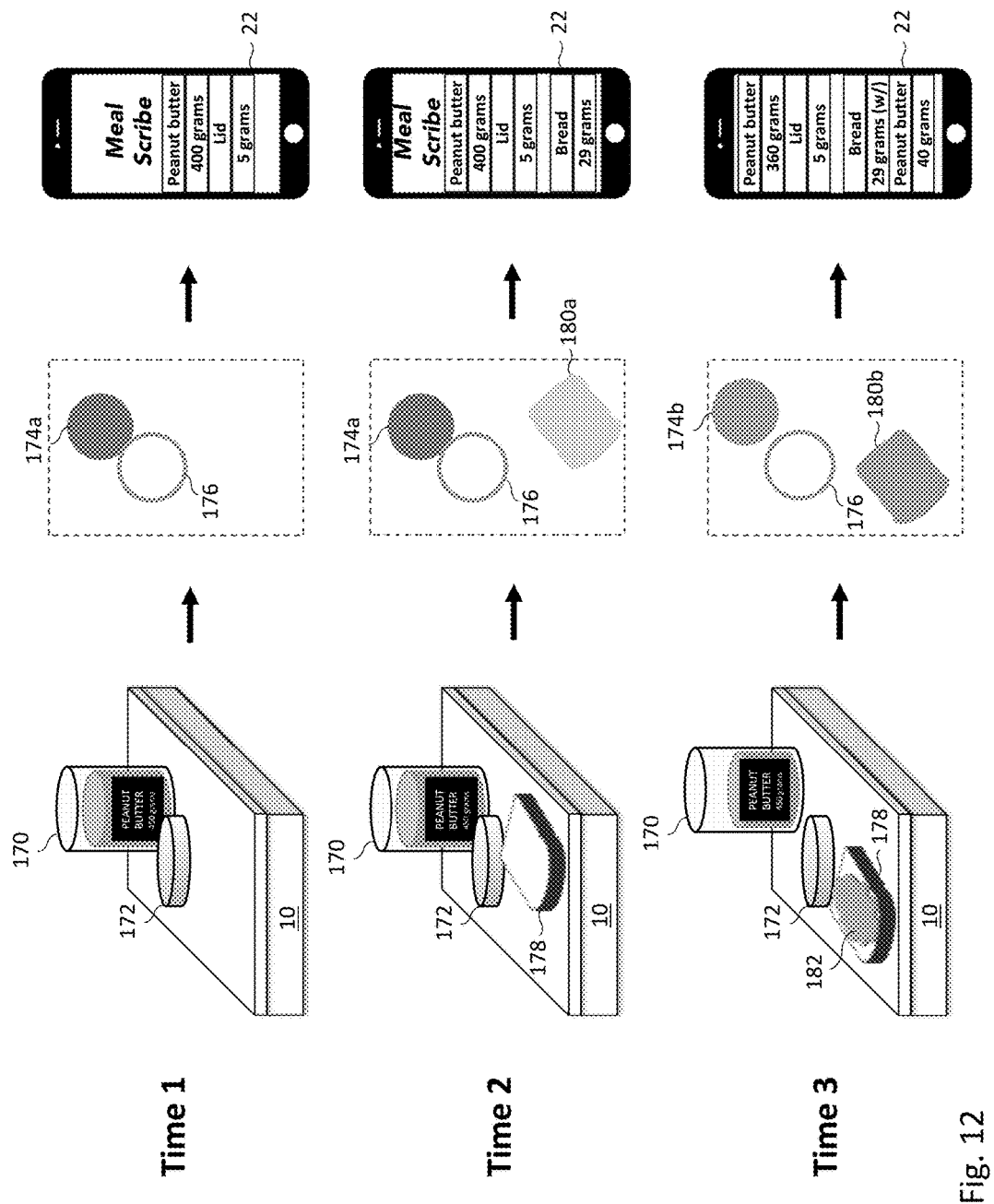
FIG. 12 depicts a portion of a food item (e.g., peanut butter) contained in a first container being transferred to a food item (e.g., piece of bread), and the computing device recognizing an amount and type of food that has been transferred to the food item, in accordance with one embodiment of the invention.

FIG. 12 depicts a portion of a food item (e.g., peanut butter) contained in a first container being transferred to a food item (e.g., piece of bread), and the computing device recognizing an amount and type of food that has been transferred to the food item, in accordance with one embodiment of the invention. More specifically, at a first time instance, container 170 (e.g., an uncovered jar of peanut butter) and cover 172 (e.g., lid of peanut butter jar) may be disposed on pressure-sensitive device 10. Pressure-sensitive device 10 may measure the weight (=400 grams) and footprint 174a of container 170. Pressure-sensitive device 10 may also measure the weight (=5 grams) and footprint 176 of cover 172. Assume that during prior steps (not depicted), computing device 22 was able to determine that container 170 is a jar of peanut butter and cover 172 is a lid of the peanut butter jar (similar to the steps of FIG. 9). The information of the registered objects may be displayed on a display of computing device 22 (e.g., "Peanut butter weighing 400 grams", "Lid weighing 5 grams").

At a second time instance, food item 178 is additionally positioned on pressure-sensitive device 10. Pressure-sensitive device 10 may measure the weight (=29 grams) and footprint 180a of food item 178. Based on the determination of the weight and the footprint of food item 178, computing device 22 may determine that food item 178 is a piece of bread. The information of the registered objects may be displayed on a display of computing device 22 (e.g., "Peanut butter weighing 400 grams", "Lid weighing 5 grams", and "Bread weighing 29 grams").

After the second time instance and before a third time instance, a portion of the food item from container 170 may be transferred to food item 178. For example, the user may transfer some peanut butter from container 170 using a knife and spread the peanut butter onto a top surface of food item 178.

At a third time instance, a portion 182 of the food item in container 170 is located on a top surface of food item 178, and the food item within container 170 is incrementally depleted. Pressure-sensitive device 10 may measure the weight (=360 grams) and footprint 174b of incrementally depleted container 170. Pressure-sensitive device 10 may also measure the weight (=5 grams) and footprint 176 of cover 172. Pressure-sensitive device 10 may also measure the weight (=69 grams) and footprint 180b of food item 178 in combination with portion 182 of the food item from container 170. Based on the determination that the weight associated with footprint 174b decreased by 40 grams and the determination that the weight associated with footprint 180b increased by 40 grams between the second and third time instances, computing device 22 may infer that 40 grams of the food item from container 170 was transferred to food item 178. In other words, computing device 22 may be able to infer that footprint 180b is now associated with 29 grams of food item 178 and 40 grams of the food item from container 170. The information of the registered objects may be displayed on a display of computing device 22 (e.g., "Peanut butter weighing 360 grams", "Lid weighing 5 grams", and "Bread weighing 29 grams with Peanut butter weighing 40 grams").

Figure 13A:
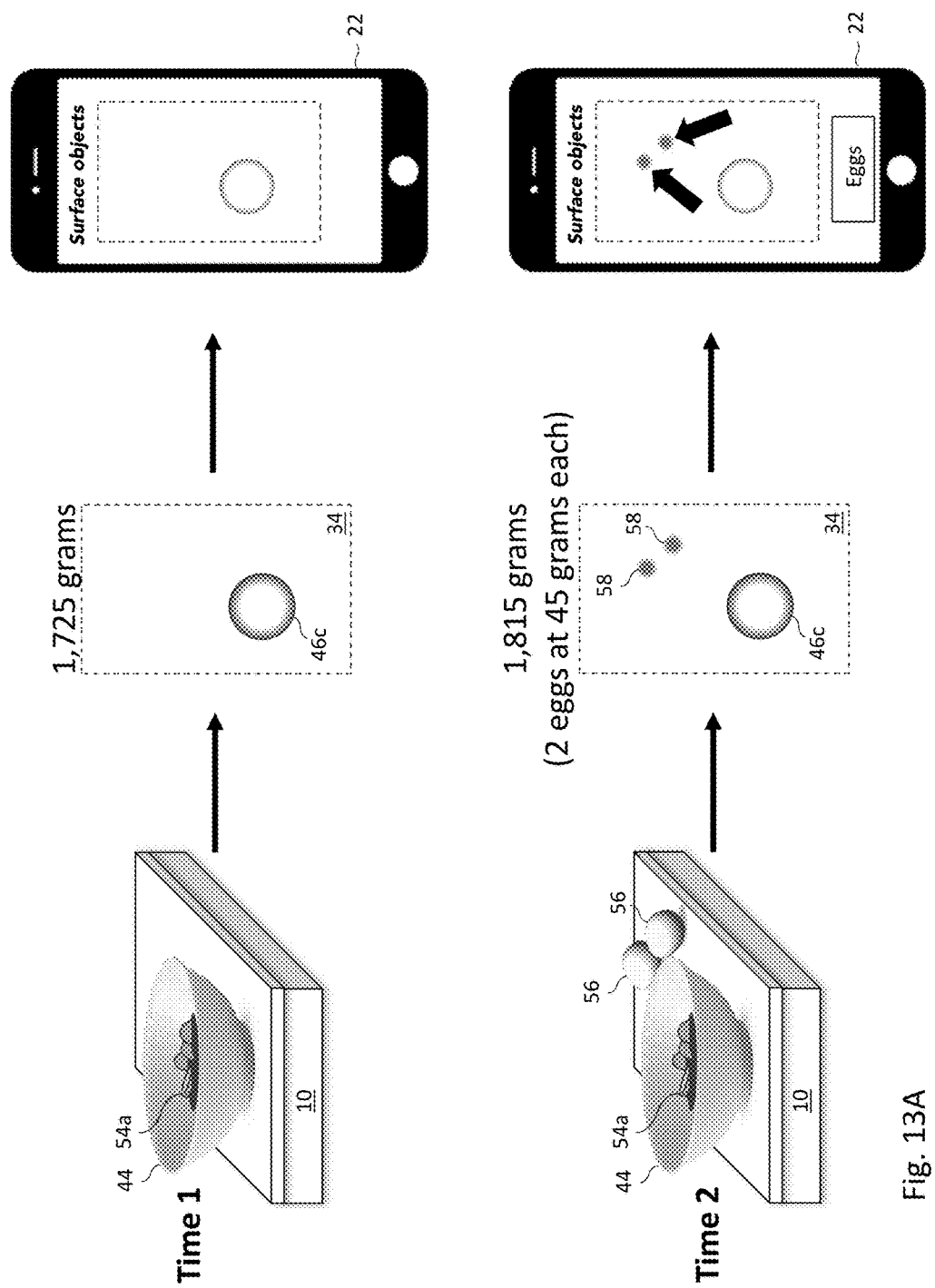
FIGS. 13A-13B depict a process for automatically registering an unpackaged food item and registering the unpackaged food item being transferred into a container, in accordance with one embodiment of the invention.
Figure 13B:
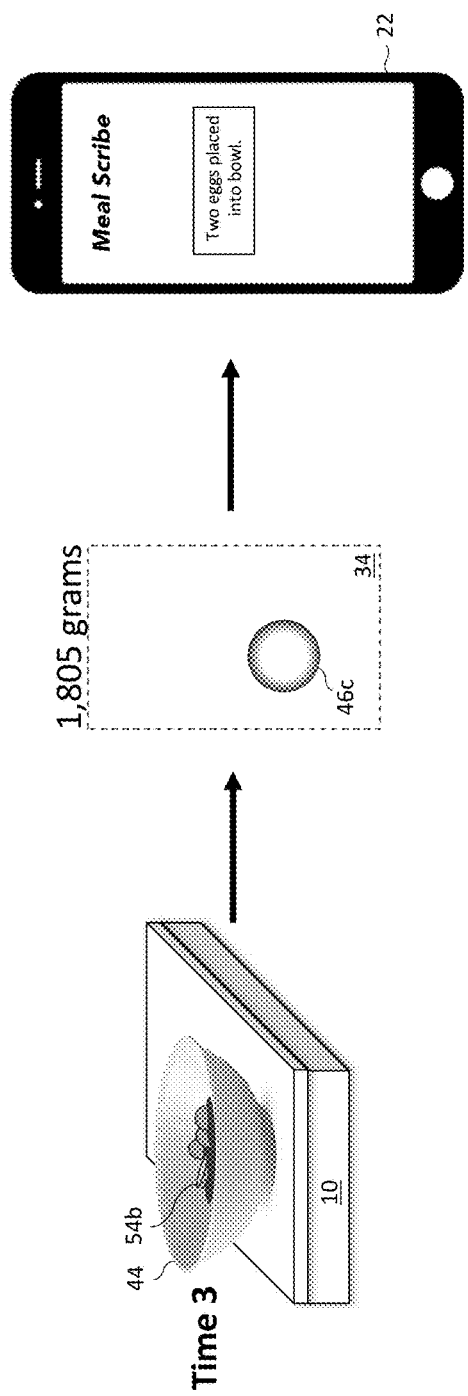

FIGS. 13A-13B depict a process for automatically registering an unpackaged food item 56 and registering the unpackaged food item being transferred into container 44. More specifically, at a first time instance, container 44 is positioned on pressure-sensitive device 10, and container 44 contains food item 54a. Pressure-sensitive device 10 may measure the footprint 46c and weight of container 44 (i.e., 1,725 grams).

At a second time instance, unpackaged food item(s) 56 are placed on pressure-sensitive device 10. Pressure-sensitive device 10 may measure the footprint 58 and weight of unpackaged food item(s) 56. In the present example, computing device 22 may determine the weight of the unpackaged food item(s) 56 to be 90 grams (i.e., equal to the increase in weight after the unpackaged food item(s) 56 are placed on pressure-sensitive device 10). Unpackaged or loose food items may be identifiable when, for example, their shape and/or weight are consistent (e.g., eggs). Also, many kinds of produce may be identifiable due (mainly) to general attributes of their pressure footprints. In the instant example, based on measured footprint 58 and the weight of unpackaged food item 56, computing device 22 may determine that the unpackaged food item(s) comprise two eggs. While the weight of eggs in general may vary (e.g., there may be small eggs, extra jumbo eggs), the deduction performed by computing device 22 may be feasible if unpackaged food items present in the user's refrigerator are registered in local food library 27, thereby limiting the possibilities of unpackaged food items from the universe of unpackaged food items to a smaller subset. For example, based on the information that the refrigerator has extra-jumbo eggs that each weight 45 grams, computing device 22 may determine with high confidence that two food items with small circular footprints that each weigh 45 grams are extra-jumbo eggs.

If, however, computing device 22 is not able to identify unpackaged food item 56, a user may manually provide computing device 22 with the identification of unpackaged food item 56. Such identification may be stored with the weight and footprint of unpackaged food item 56 (e.g., in local food library), such that subsequent placement of unpackaged food item 56 on pressure-sensitive device 10 would promptly result in the identification of unpackaged food item 56 without user interaction.

At the third time instance, pressure-sensitive device 10 may no longer measure the footprints of unpackaged food items 56, and may measure the footprint 46c and weight (=1,805 grams) of container 44. Based on the increase in weight of container 44 (1,805 grams–1,725 grams=80 grams) being substantially equal to the weight of the unpackaged food item(s) (=90 grams), computing device 22 may determine that unpackaged food item(s) 56 was transferred into container 44. The registration of such step may be presented to the user (e.g., "Two eggs placed into bowl") and/or stored in local food library 27. In the present example, computing device 22 may have prior knowledge, e.g., through the food libraries, that whenever eggs are placed into container 44 only the egg white and yolk of the eggs (and not the shells) are placed into container 44.

Figure 14A:
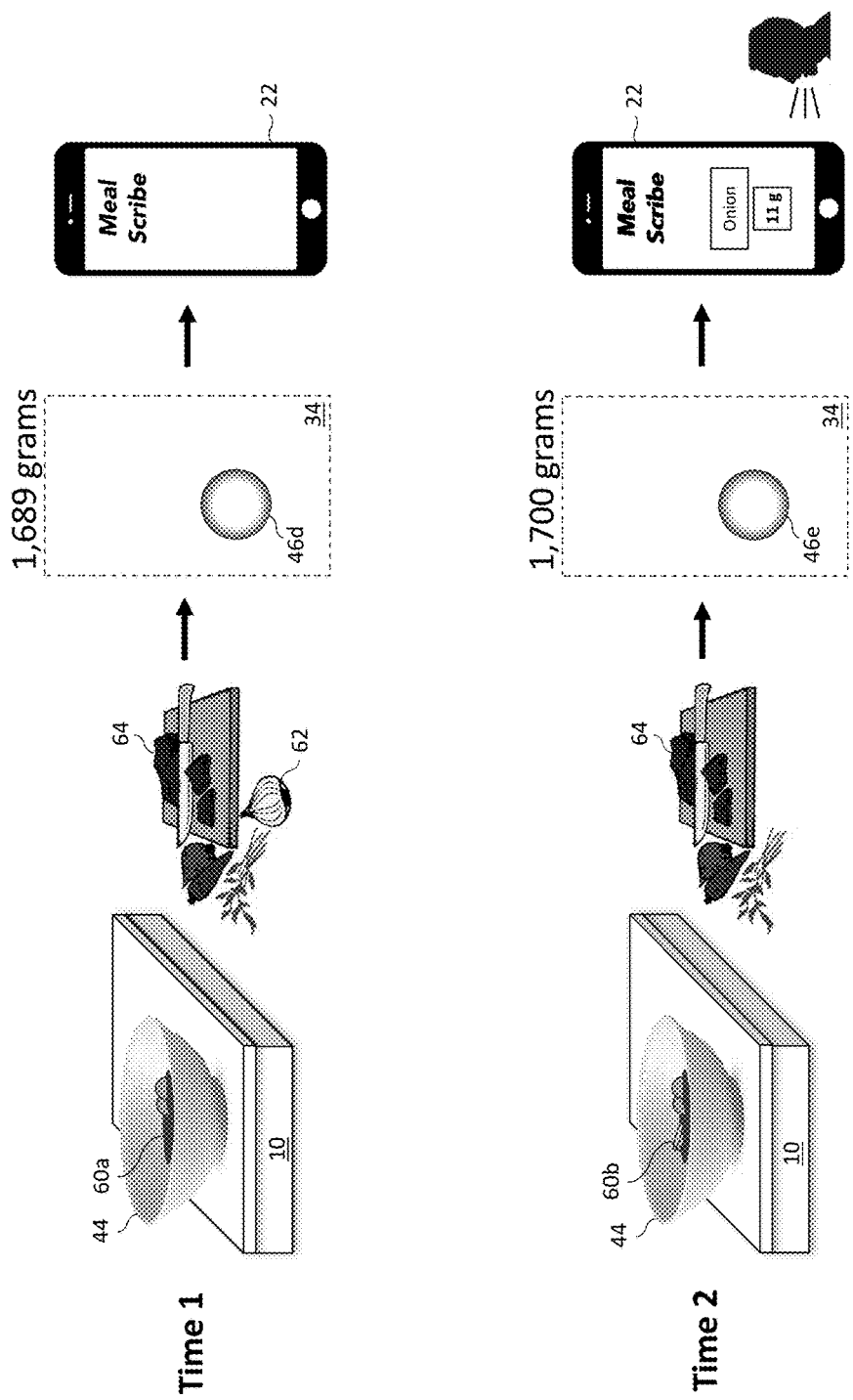
FIGS. 14A-14B depict ingredients being placed into a container one ingredient at a time, and the computing device determining an identity and amount of each of the ingredients that are placed into the container, in accordance with one embodiment of the invention.
Figure 14B:
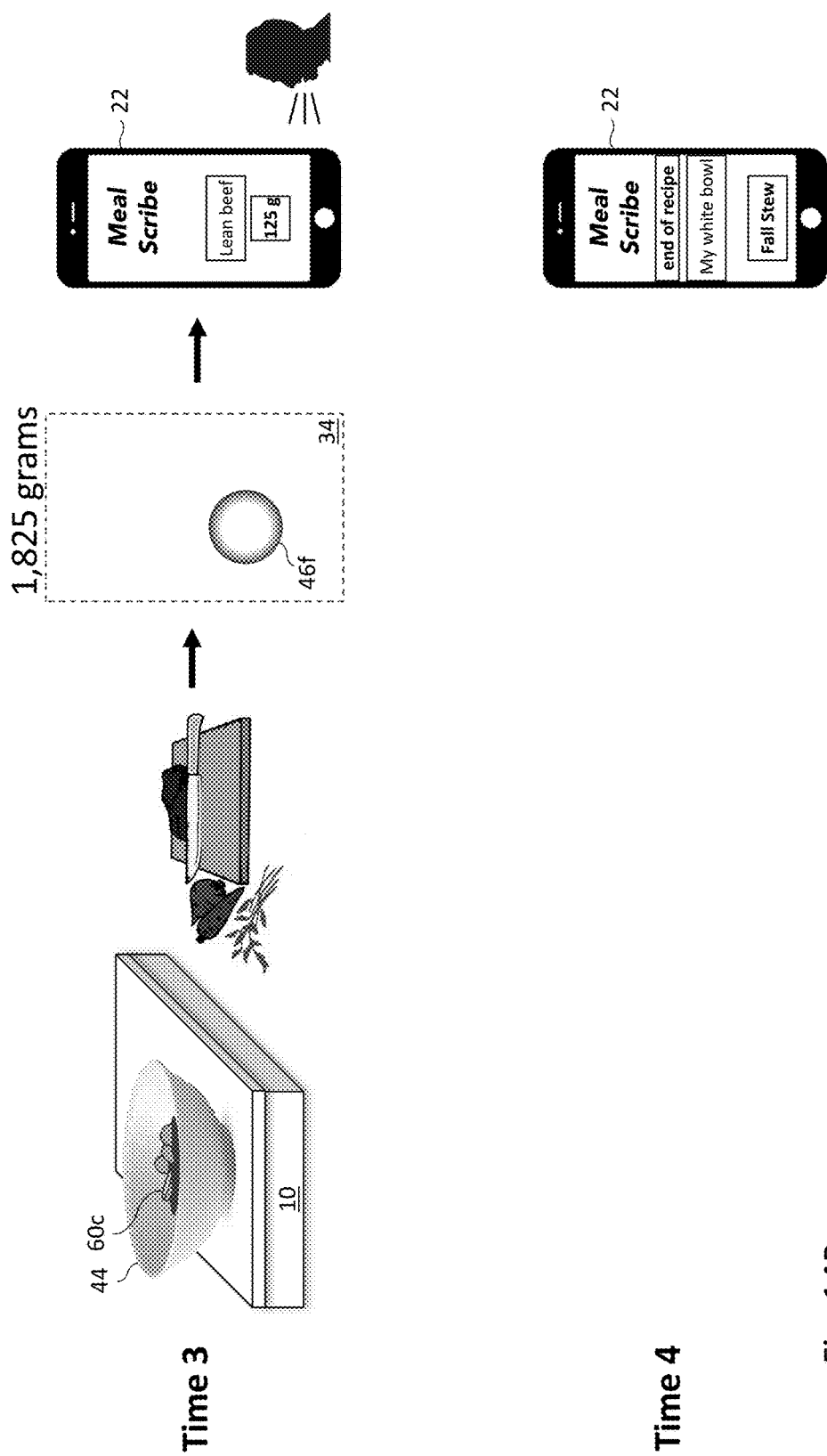

FIGS. 14A-14B depict ingredients being placed into a container one ingredient at a time, and the computing device determining an identity and amount of each of the ingredients that are placed into the container. More specifically, FIGS. 14A-14B illustrate the scenario in which pressure-sensitive device 10 does not have the opportunity to measure a footprint of a food item before the food item is placed into container 44 (e.g., food item is directly transferred from a cutting board into container 44). While computing device 22 may be able to infer a weight of each of the ingredients, computing device 22 may not be able to determine an identity of the food item. Accordingly, the identity of each of the ingredients may instead be queried from a user following the placement of each food item in container 44.

FIGS. 14A-14B illustrate the steps for preparing a "fall stew". At a first time instance, container 44 contains ingredients 60a and pressure-sensitive device 10 determines the weight (=1,689 grams) and footprint 46d of container 44. At a second time instance, food item 62 is placed into container 44 (container 44 now containing ingredients 60b). Upon pressure-sensitive device 10 measuring the weight (=1,700 grams) and footprint 46e of container 44, computing device 22 may infer that a food item of 11 grams has been placed into container 44. A user may manually provide the identity of food item 62 to computing device 22 (in this example "onion"). At a third time instance, food item 64 is placed into container 44 (container 44 now containing ingredients 60c). Upon pressure-sensitive device 10 measuring the weight (=1,825 grams) and footprint 46f of container 44, computing device 22 may infer that a food item of 125 grams has been placed into container 44. A user may manually provide the identity of food item 64 to computing device 22 (in this example "lean beef").

Computing device 22 may store a recipe (in the current example for "fall stew") and as each step of the recipe is registered, record the completion of each step of the recipe. Upon all steps of the recipe being completed, computing device 22 may display a message to the user (at Time 4) that the recipe has been completed (e.g., "end of recipe"). Alternately, had no recipe been followed by the user, then the recorded completion of steps may serve as the outline for constructing a new recipe. In the current embodiments, the recording is only an outline because it would include the amount of what was added when, but it would not include how (i.e., extended instructions like "stir", "whip", etc.). The recording of steps permits the steps of an improvised meal preparation to be saved and for a proper recipe to be created based on the recorded steps. In another embodiment, the meal accounting system would detect the transient footprint pressure variations in response to steps such as "stir", "whip", etc. The algorithm would classify the transient signatures (i.e., the transient footprint pressure variations) as substantially corresponding to actions such as "stir", "whip", etc. This may be analogous to how a fitness tracker (e.g., FitBit™) discriminates between walking, running, etc. The algorithm may then compare these classified actions, their duration, and intensity against the followed recipe (to see whether the user is following the recipe) or may embed them in the new recipe to yield a more complete record of the meal preparation.

Figure 15:
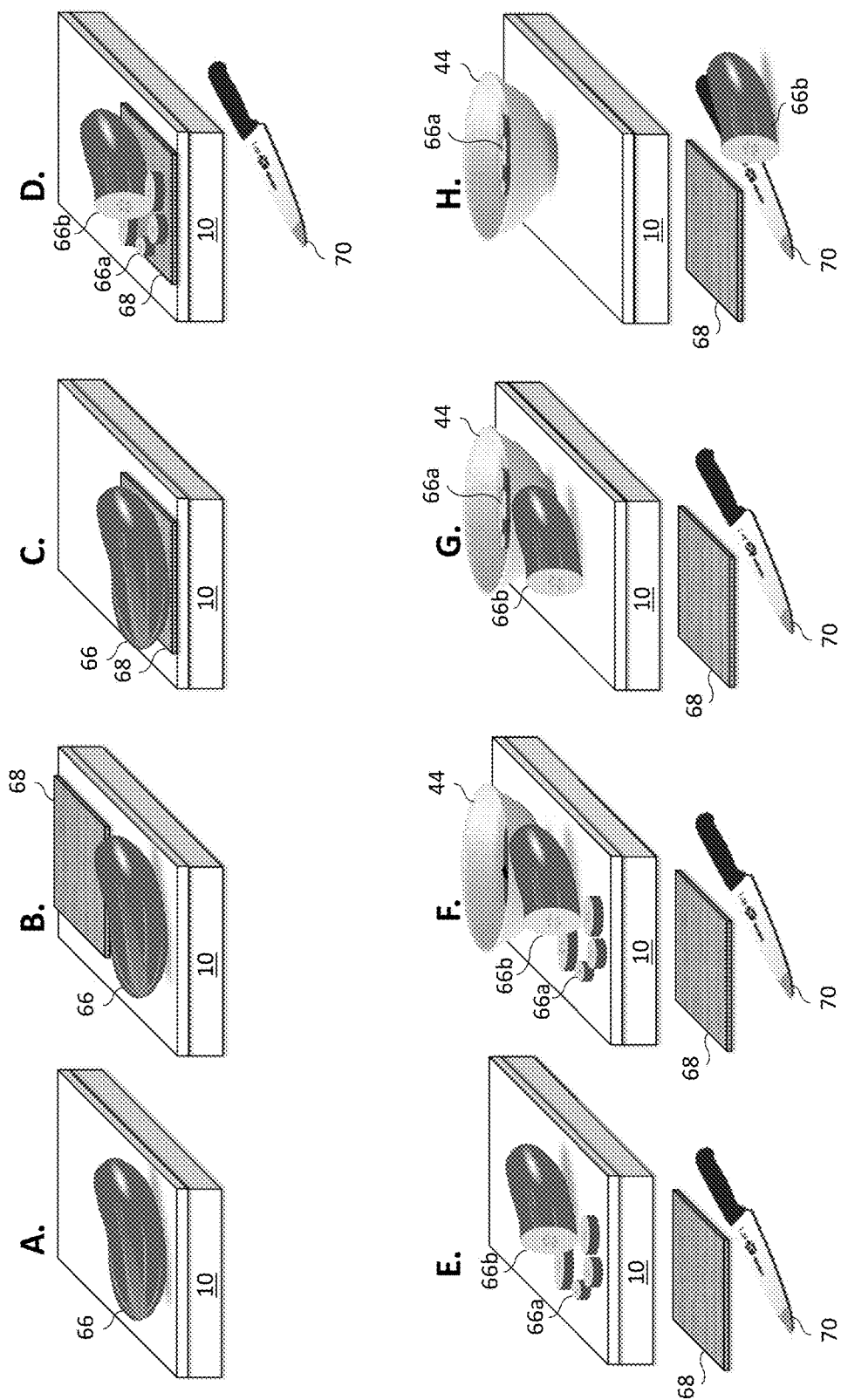
FIG. 15 depicts an unpackaged food item (e.g., a cucumber) being divided (e.g., cut) into several portions, one or more of those portions being placed into a container, and computing device determining an identity and amount of the unpackaged food item that was placed into the container, in accordance with one embodiment of the invention.

FIG. 15 depicts an unpackaged food item (e.g., a cucumber) being divided (e.g., cut) into several portions on cutting board 68, one or more of those portions being placed into container 44, and computing device 22 determining an identity and amount of the unpackaged food item that was placed into container 44. At step A, food item 66 may be placed on pressure-sensitive device 10. The identity of food item 66 (i.e., a cucumber) may be determined based on its footprint and weight as measured by pressure-sensitive device 10, or the identity of food item 66 may be provided by the user to computing device 22. Rules to recognize food objects like fruit and vegetables may leverage characteristic footprint and weight to handle shape and weight variations (e.g., larger footprint implies greater weight).

At step B, cutting board 68 may be placed on pressure-sensitive device 10. Cutting board 68 may be recognized by its pressure footprint and weight from a previous use or, if this is the first time cutting board 68 is being used with pressure-sensitive device 10, cutting board 68 may be registered by the user.

At step C, cutting board 68 may be placed under cucumber 66. The footprint of cucumber 66 may disappear, the total weight of the objects may remain unchanged, and the footprint of cutting board 68 may include a pressure distribution with higher pressure measurements. Therefore, computing device 22 may be able to infer that cucumber 66 is located on cutting board 68 (i.e., as computing device 22 would infer a food item placed in a container).

At step D, cucumber 68 may be sliced with knife 70, forming sliced portions 66a and unsliced portion 66b. Any transient pressures sensed by pressure-sensitive device 10 due to the act of slicing can be ignored by computing device 22. The total weight of the objects is unchanged, and the change in the footprint of cutting board 68 is either too small to measure or is insignificant.

At step E, cutting board 68 may be removed from pressure-sensitive device 10. The weight reduction measured by pressure-sensitive device 10 equals the cutting board's weight and the remaining weight equals the cucumber's weight. As a result, computing device 22 may deduce that the footprint measured by pressure-sensitive device 10 corresponds to a new footprint of the cucumber comprising sliced portions 66a and unsliced portions 66b. Again, it is noted that a footprint, such as the footprint corresponding to sliced portions 66a, may comprise non-contiguous contact areas. In response to this deduction, computing device 22 may store in local food library 27 an association between the identity of food item 66 (i.e., cucumber), the footprint of food item 66 from step A and the footprint of food item 66 from step E.

At step F, container 44 may be placed on pressure-sensitive device 10, and may be recognized by its footprint and weight.

At step G, cucumber slices 66a may be placed into container 44. Such step may be inferred by computing device 22, because the total weight of the objects between steps F and G is unchanged, but a portion of the footprint belonging to cucumber is no longer present. The remaining (unsliced) cucumber's footprint and weight may be automatically registered based on the deduction in step E. Alternatively, the weight of container 44 may be determined in step G, and the weight of the unsliced cucumber 66b may be determined in step G. Upon determining that the difference in weight of container 44 between steps G and F equals the difference in weight of the cucumber between steps G and F, computing device 22 may determine that a portion of the cucumber with weight equal to the difference in weight of the cucumber between steps G and F has been transferred into container 44. Computing device 22 may additionally store in local food library 27 that a portion of the cucumber with weight equal to the difference in weight of the cucumber between steps G and F (e.g., 100 grams) has been transferred into container 44.

At step H, the unsliced cucumber portion 66b may be removed, perhaps to be stored as a leftover. Because its footprint and weight had been registered, it will be identified automatically when it is used again.

Figure 16A:
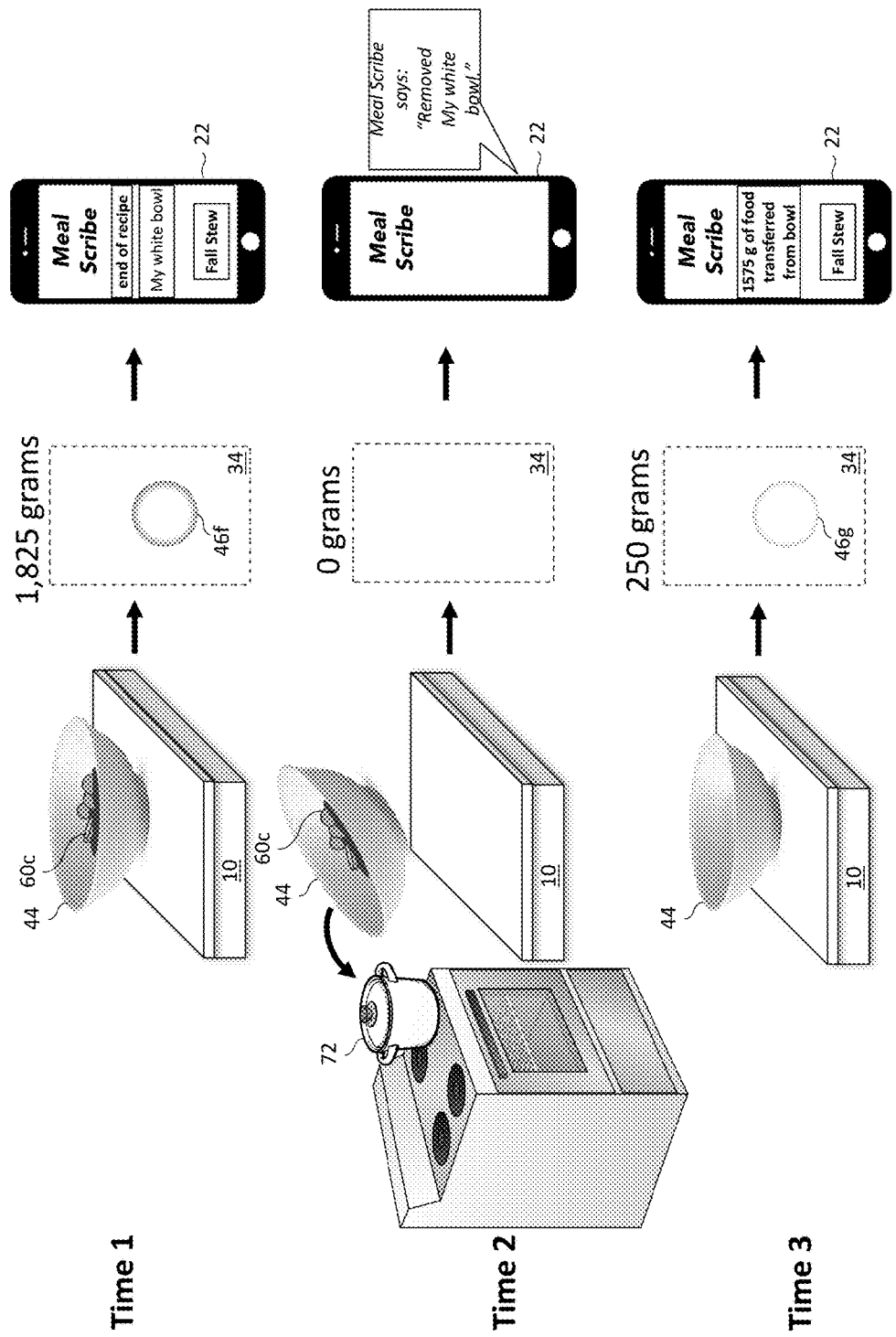
FIGS. 16A-16B depict a first container resting on the pressure-sensitive device and a second container not resting on the pressure-sensitive device (e.g., resting on a stove), a portion of the contents of the first container being transferred to the second container, a portion of the contents of the second container being transferred back to the first container, and the computing device registering each of these steps of the meal preparation process, in accordance with one embodiment of the invention.
Figure 16B:
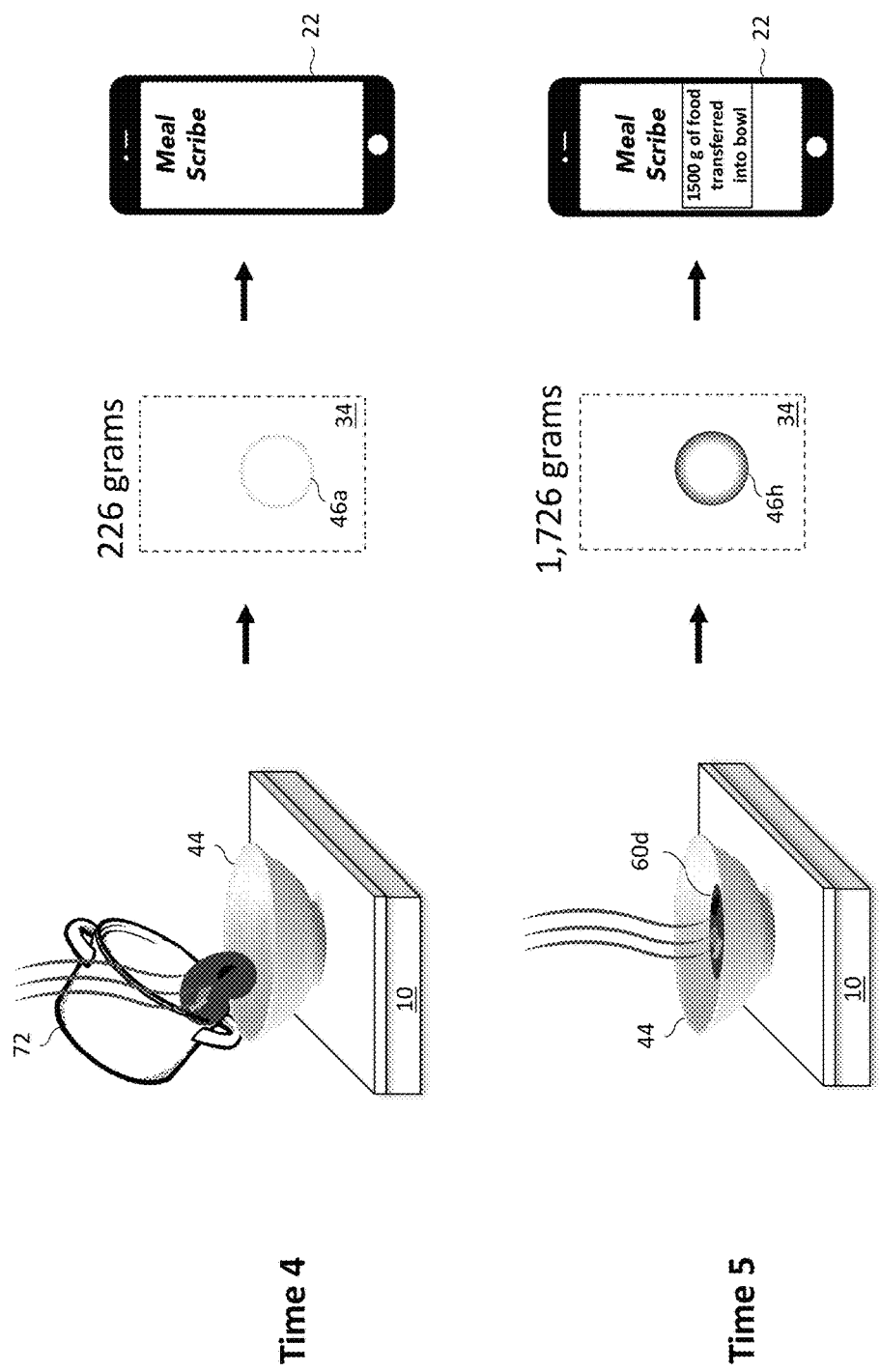

FIGS. 16A-16B depict a first container resting on the pressure-sensitive device and a second container not resting on the pressure-sensitive device (e.g., resting on a stove), a portion of the contents of the first container being transferred to the second container, a portion of the contents of the second container being transferred back to the first container, and the computing device registering each of these steps of the meal preparation process.

At a first time instance, container 44 is disposed on pressure-sensitive device 10 with ingredients 60c. Pressure-sensitive device 10 may measure the weight (=1,825 grams) and footprint 46f container 44. Time 1 of FIG. 16A may correspond to Time 3 of FIG. 14B.

At a second time instance, pressure-sensitive device 10 may measure a weight of 0 grams and no footprint. In response to such measurements, computing device 22 may determine that container 44 has been removed from pressure-sensitive device 10 (e.g., speak "Removed My white bowl").

At a third time instance, pressure-sensitive device 10 may measure the weight (=250 grams) and footprint 46g of container 44. Upon recognizing the shape of footprint 46g to be substantially equal to the shape of footprint 46f, computing device 22 may determine that container 44 has been returned to pressure-sensitive device 10, and 1575 grams of the contents of container 44 have been removed from container 44. As such, computing device 22 may inform the user that "1575 g of food transferred from bowl". In the present example, the contents were transferred into pot 72, but computing device 22 may not have knowledge of pot 72 or its contents.

At a fourth time instance, container 44 has been washed and cleaned, and pressure-sensitive device 10 measures its weight when empty of contents (=226 grams) and footprint 46a. In response to such measurements, computing device 22 may determine that the white bowl has been placed on pressure-sensitive device 10.

At a fifth time instance, pressure-sensitive device 10 measures a new weight (=1,726 grams) and footprint 46h of container 44. In response to such measurements, computing device 22 may determine that 1,500 grams of food have been transferred into container 44. Computing device 22 may not have knowledge of the identity of the food, so computing device 22 may query the user for an identity of the food within container 44. Alternatively, it may be possible for computing device 22 to infer that container 44 contains fall stew, based on 1,575 grams of the ingredients for fall stew being transferred from container 44 during Times 1-3, and a similar weight (1,500 grams) of a food item being placed into container 44 at Time 5. The inference would be based on the similarity in weight of the food item being transferred out and then back into container 44.

Figure 17A:
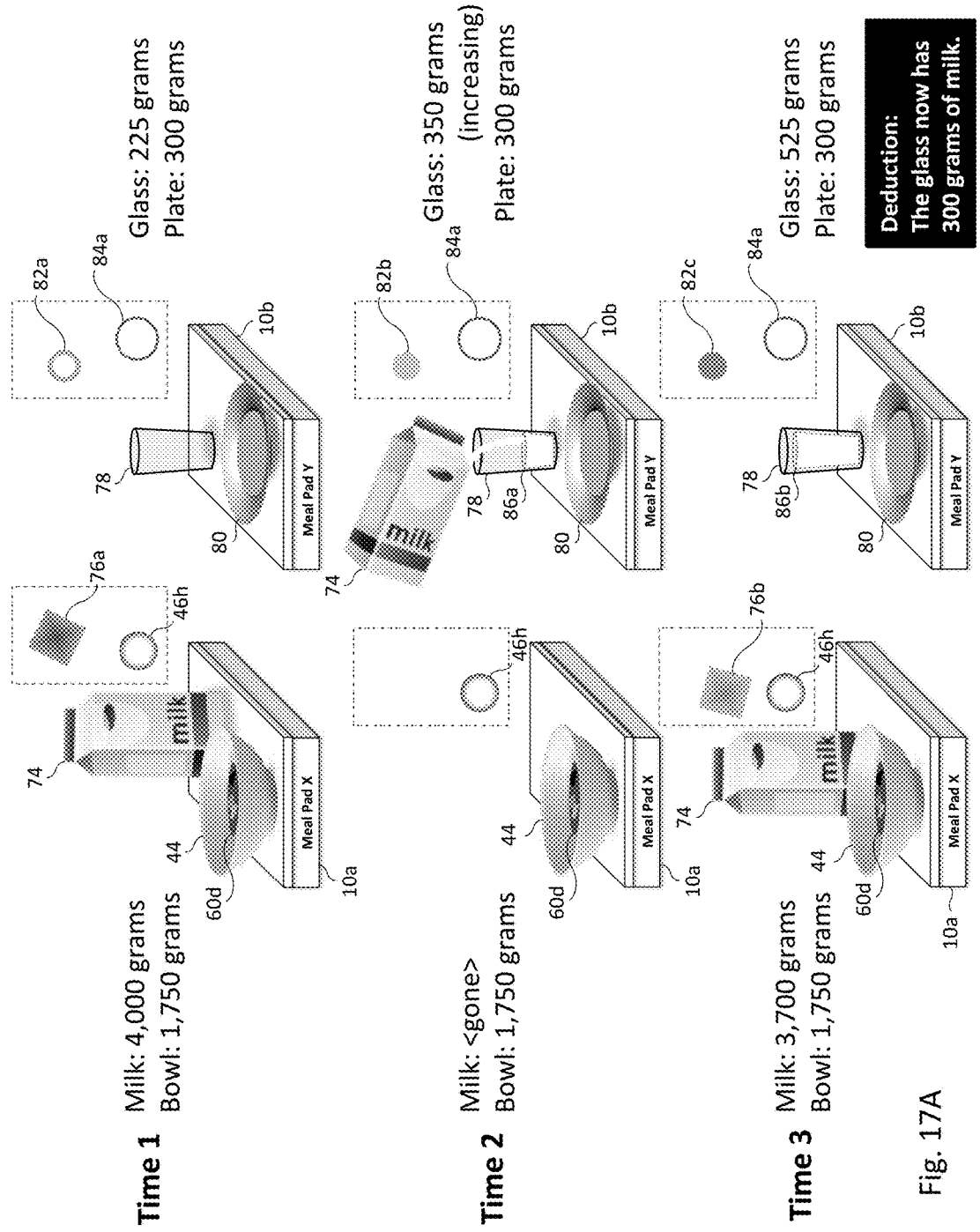
FIG. 17A depicts a first food item (e.g., milk) being transferred from a first container (e.g., milk carton) into a second container (e.g., cup), and the computing device determining an amount and identity of the first food item present in the second container, in accordance with one embodiment of the invention.
Figure 17B:
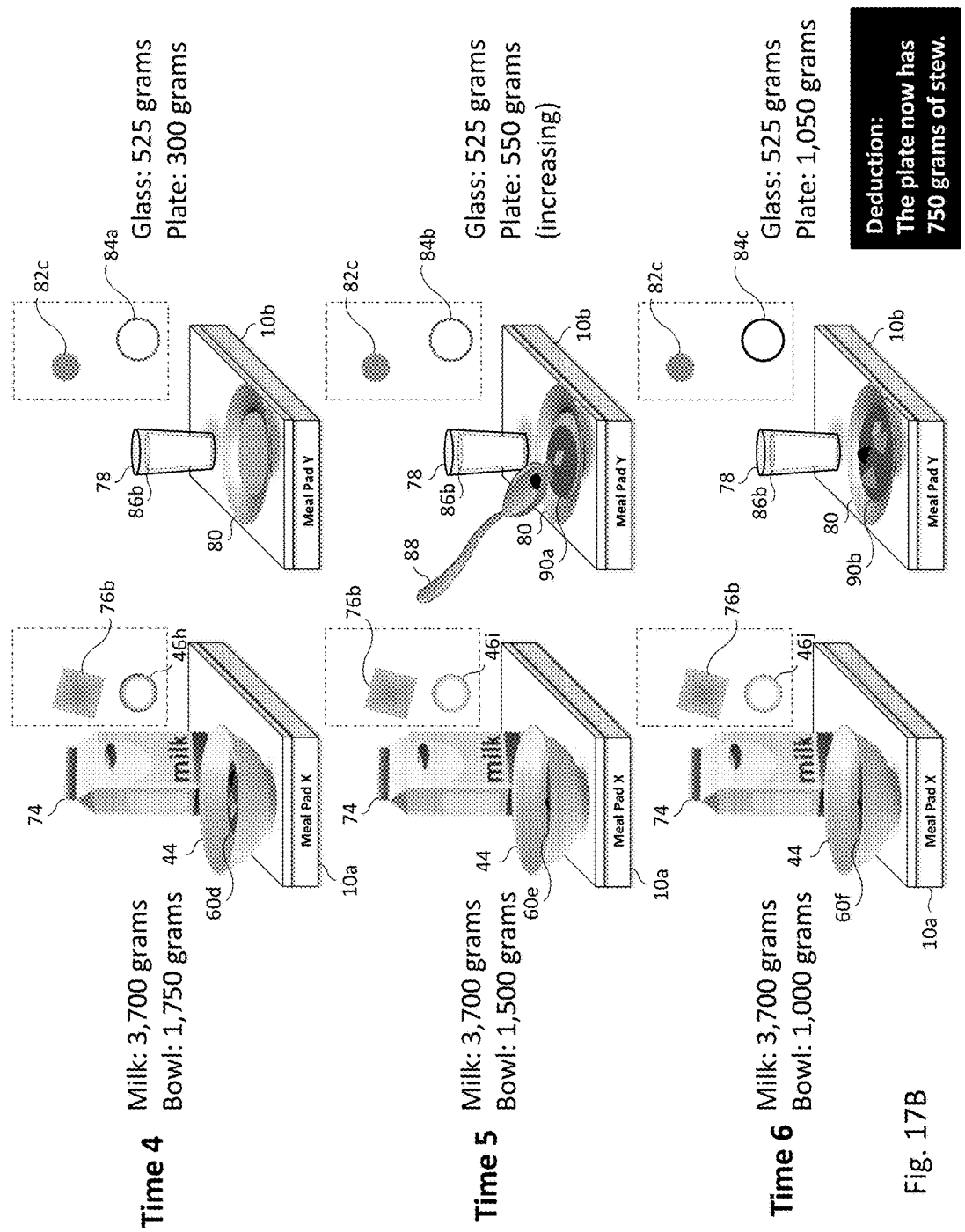
FIG. 17B depicts a second food item (e.g., stew) being transferred from a third container (e.g., bowl) into a fourth container (e.g., plate), and the computing device determining an amount and identity of the second food item present in the fourth container, in accordance with one embodiment of the invention.
Figure 18:
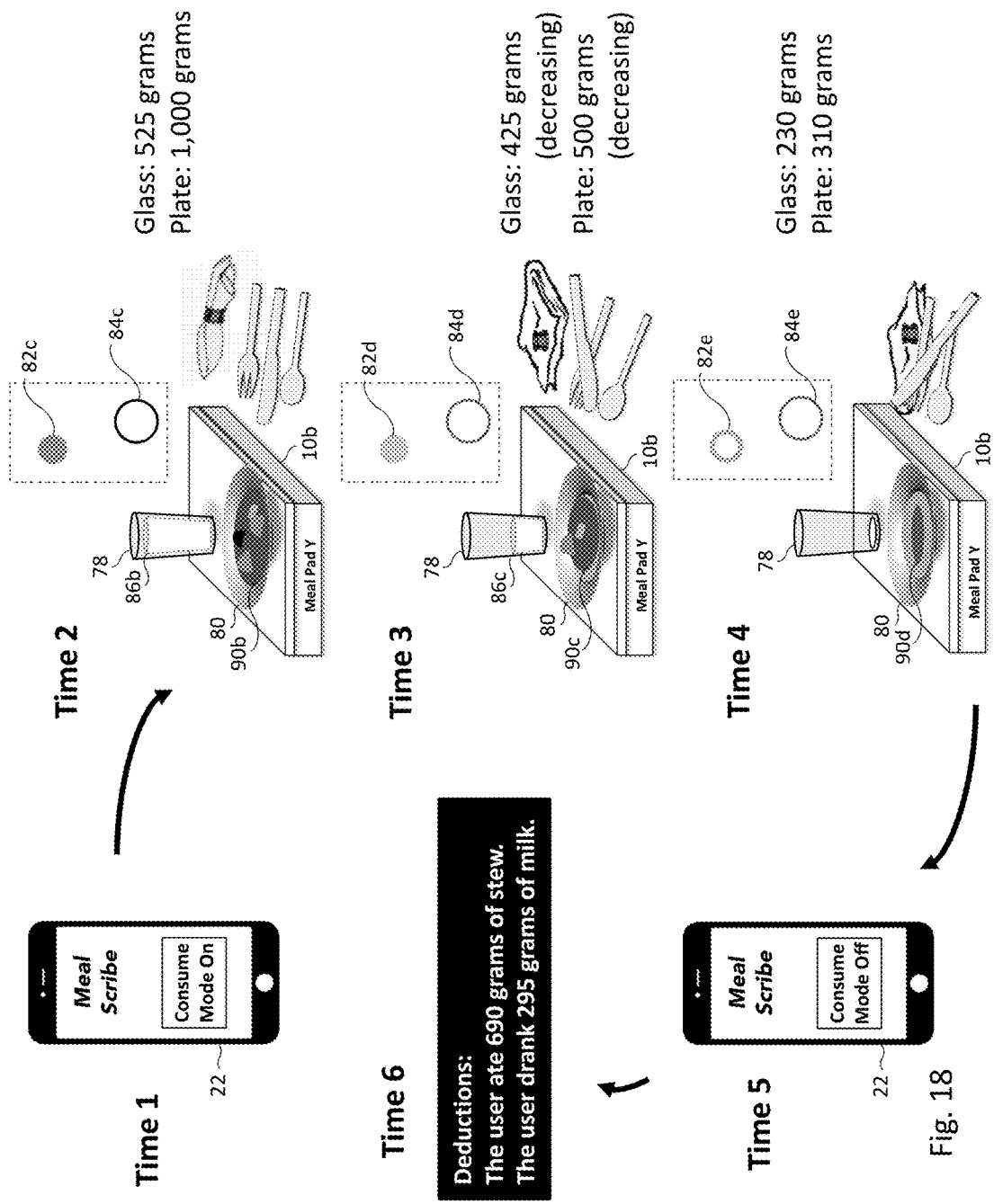
FIG. 18 depicts the activation of a "consume mode", the consumption of food, the deactivation of the consume mode, followed by a computing device determining an identity and amount of one or more food items that were consumed, in accordance with one embodiment of the invention.
Figure 19:
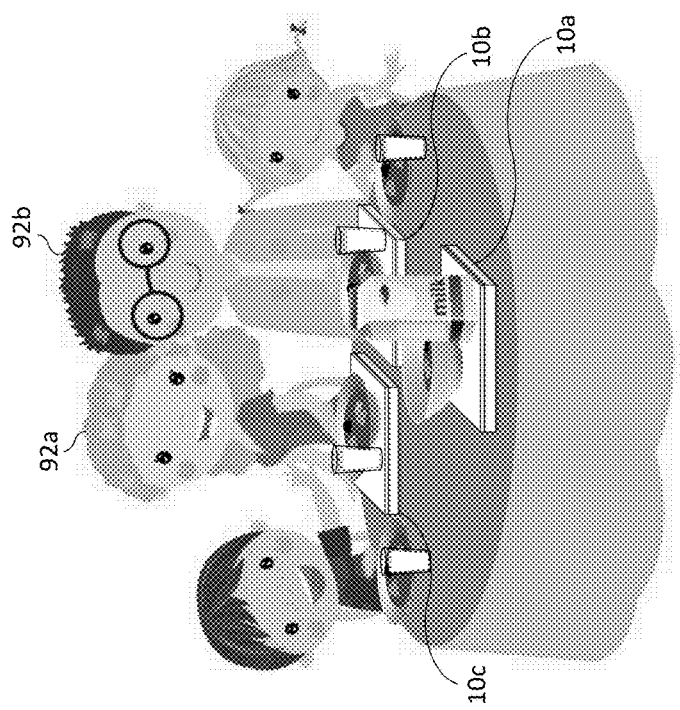
FIG. 19 depicts a plurality of pressure-sensitive devices and how the pressure-sensitive devices may be utilized by a plurality of people, in accordance with one embodiment of the invention.
Figure 20:
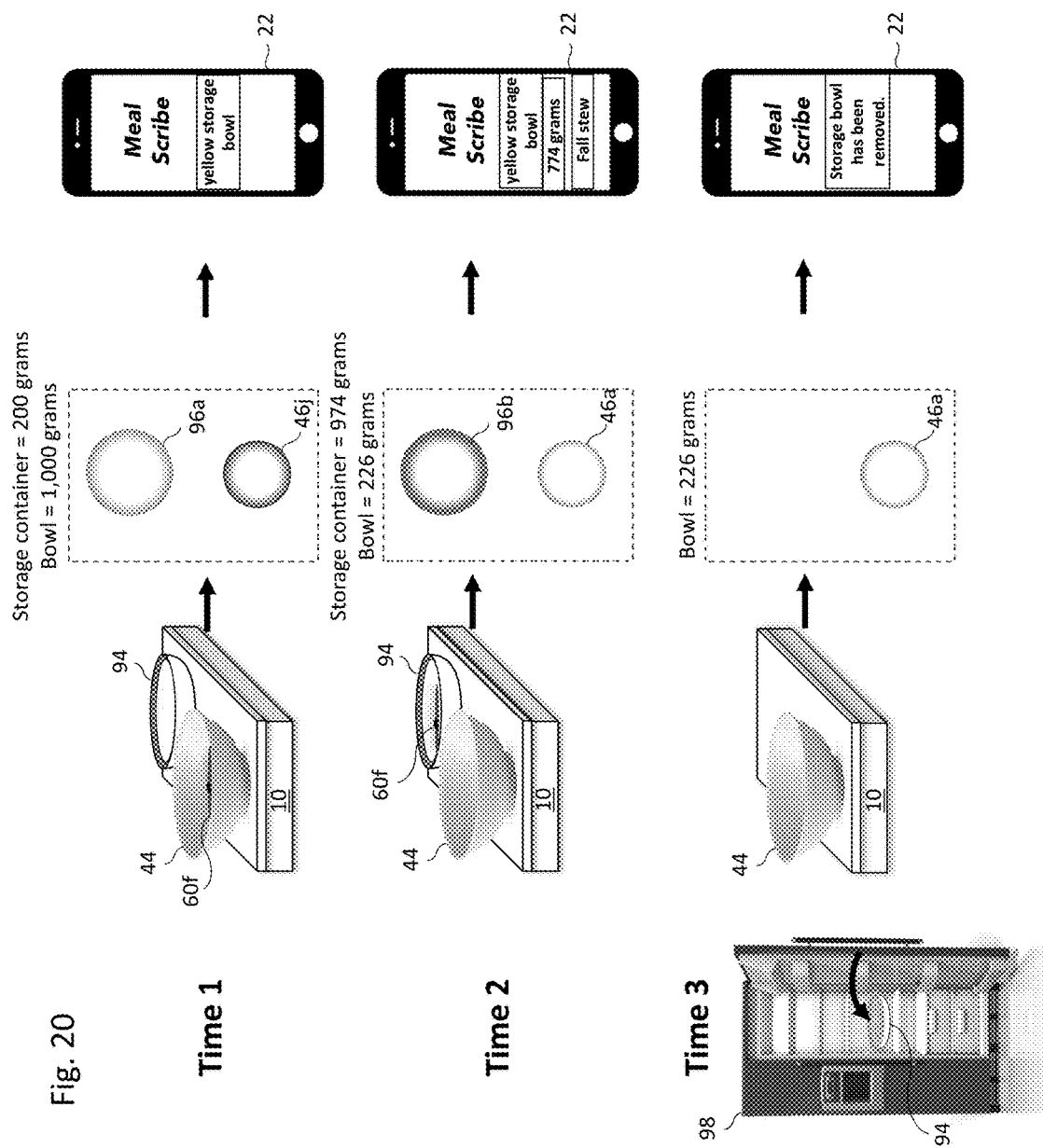
FIG. 20 depicts a food item (e.g., leftovers) being transferred from a first container (e.g., bowl) to a second container (e.g., storage container), the second container being placed into a refrigerator, and the computing device determining an amount and identity of the food item that was placed into the second container, in accordance with one embodiment of the invention.
Figure 21:
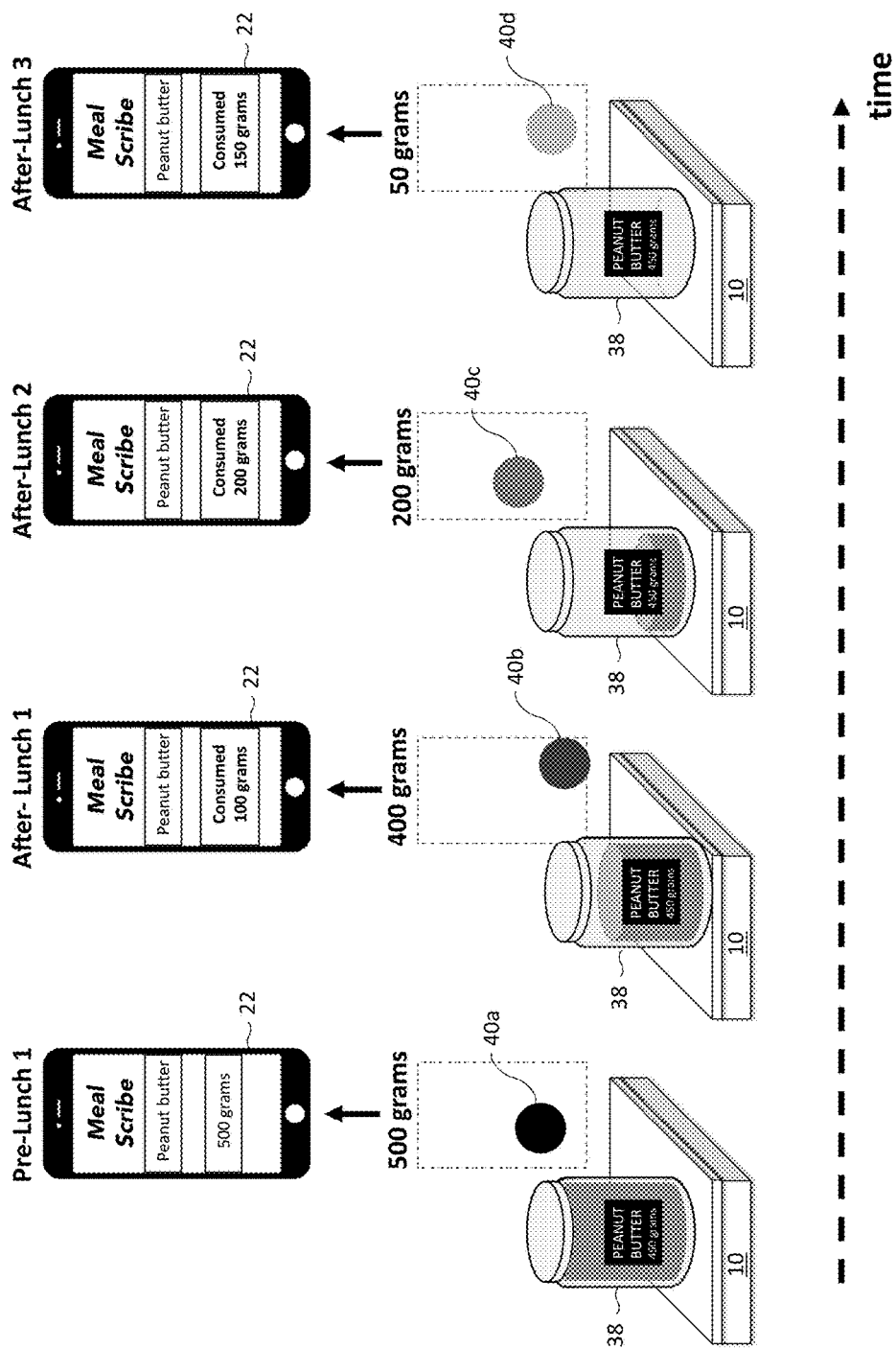
FIG. 21 depicts a computing device recording the amount and identity of a food item that is initially present and that is subsequently consumed during a plurality of meals, in accordance with one embodiment of the invention.

FIGS. 17A-21 describe how pressure-sensitive device 10 in conjunction with computing device 22 may be used during the food serving, consumption and storage stages of a meal lifecycle. In particular, FIGS. 17A-17B describe how to track the portioning or serving of food; FIGS. 18 and 21 describe how to track the consumption of food; and FIG. 20 describes how to track the storage of food FIG. 17A depicts a first food item (e.g., milk) being transferred from a first container (e.g., milk carton) into a second container (e.g., cup), and the computing device deducing an amount and identity of the first food item present in the second container.

More specifically, at a first time instance, container 44 (e.g., bowl) and container 74 (e.g., milk carton) may be disposed on pressure-sensitive device 10a. Container 44 may contain food item 60d and container 74 may contain a food item that is not visible (e.g., milk). Pressure-sensitive device 10a may measure the weight (=4,000 grams) and footprint 76a of container 74, and may measure the weight (=1,750 grams) and footprint 46h of container 60d. Such weight measurements may be obtained by integrating the respective pressure distributions of the containers. Also at the first time instance, container 78 (e.g., cup) and container 80 (e.g., plate) may be disposed on pressure-sensitive device 10b. Pressure-sensitive device 10b may measure the weight (=225 grams) and footprint 82a of container 78, and may measure the weight (=300 grams) and footprint 84a of container 80.

At a second time instance, container 74 may be removed from pressure-sensitive device 10a. Pressure-sensitive device 10a may no longer measure footprint 76a. In response to such measurement, computing device 22 may determine that container 74 has been removed from pressure-sensitive device 10a. Also at the second time instance, food item 86a may be transferred from container 74 into container 78. Pressure-sensitive device 10b may measure a changing weight (=350 grams) and footprint 82b of container 78. In response to such measurement, computing device 22 may determine that 125 grams of food have been transferred into container 78, but at this point it may not be able to determine what that type of food is.

At a third time instance, container 74 may be returned to pressure-sensitive device 10a. Pressure-sensitive device 10a may measure the weight (=3,700 grams) and footprint 76b of container 74. In response to such measurement, computing device 22 may determine that 300 grams have been removed from container 74. Also at the third time instance, container 78 may be filled with food item 86b. Pressure-sensitive device 10b may measure a weight (=525 grams) and footprint 82c of container 78. In response to such measurement, computing device 22 may determine that 300 grams of food have been transferred from container 74 into container 78.

Based on the amount of food transferred from container 74 being equal to the amount of food transferred to container 78, computing device 22 may determine that 300 grams of the food item from container 74 have been transferred into container 78. Upon further identifying that container 74 contains milk (via a process similar to FIGS. 3 and 4), computing device 22 may determine that 300 grams of milk have been transferred into container 78. Further, computing device 22 may store in local food library 27 that 300 grams of milk have been transferred into container 78.

The fourth time instance depicted in FIG. 17B is identical to the third time instance depicted in FIG. 17A.

At a fifth time instance, a portion of the food item from container 44 is transferred to container 80 using spoon 88 (or more generally any food transferring instrument). Food item 60e remains in container 44 and food item 90a is now present in container 80. Pressure-sensitive device 10a may measure the weight (=1,500 grams) and footprint 46i of container 44. In response to such measurement, computing device 22 may determine that 250 grams of food have been removed from container 44. Further, pressure-sensitive device 10*b* may measure a weight (=550 grams) and footprint 84*b* of container 80. In response to such measurement, computing device 22 may determine that 250 grams of food have been transferred into container 80.

At a sixth time instance, the portioning of food from container 44 to container 80 is finished. Pressure-sensitive device 10*a* may measure the weight (=1,000 grams) and footprint 46*j* of container 44. In response to such measurement, computing device 22 may determine that 750 grams of food have been removed from container 44. Further, pressure-sensitive device 10*b* may measure a weight (=1,050 grams) and footprint 84*c* of container 80. In response to such measurement, computing device 22 may determine that 750 grams of food have been transferred into container 80. Based on the amount of food transferred from container 44 being equal to the amount of food transferred to container 80, computing device 22 may determine that 750 grams of food have been transferred from container 44 into container 80. Upon further identifying that container 44 contains stew (perhaps due the registration step from Time 5 of FIG. 16B), computing device 22 may determine that container 80 contains 750 grams of stew. Importantly, the meal accounting system is able to track the portioning or serving of food without any overhead for the user.

While two pressure-sensitive devices 10*a*, 10*b* are utilized in the example of FIGS. 17A and 17B, it is possible for a similar procedure to be performed with a single pressure-sensitive device that is large enough to hold all of the containers 44, 74, 78 and 80. Alternatively, a smaller pressure-sensitive device could have been used, but following a process of placing object onto the pressure-sensitive device, registering its footprint and weight, removing the object, then advancing to the next object as the food is distributed.

FIG. 18 depicts the activation of a "consume mode", the consumption of food, the deactivation of the consume mode, followed by a computing device deducing an identity and amount of one or more food items that were consumed. In some instances, the process of FIG. 18 may begin (at the first time instance) with a user setting a software application running computing device 22 to a "Consume" mode. When operating in this mode, computing device 22 interprets weight reductions as food that has been consumed by the user. In addition or in the alternative, controls (e.g., button to enable "consume" mode) may be present on pressure-sensitive device 10 in addition or in the alternative to controls being present on computing device 22.

The second time instance depicts a meal prior to a user starting to consume the meal. Container 80 and 78 may be disposed on pressure-sensitive device 10*b*. Container 80 may contain food item 90*b*, and container 78 may contain food item 86*b*. Pressure-sensitive device 10*b* may measure the weight (=525 grams) and footprint 82*c* of container 78, and weight (=1,000 grams) and footprint 84*c* of container 80.

The third time instance depicts a partially consumed meal. Pressure-sensitive device 10*b* may measure the weight (=425 grams) and footprint 82*d* of container 78, and weight (=500 grams) and footprint 84*d* of container 80. Refills can be automatically tracked, as per FIG. 17A-17B.

The fourth time instance depicts a fully consumed meal. Pressure-sensitive device 10*b* may measure the weight (=230 grams) and footprint 82*e* of container 78, and weight (=310 grams) and footprint 84*e* of container 80.

At the fifth time instance, the user may turn the consume mode to off, alerting computing device 22 that the user has finished eating the meal.

At the sixth time instance, computing device 22 may determine that the user ate 690 grams of stew and drank 295 grams of milk. 295 grams may be calculated as the weight of container 78 at Time 2 (i.e., 525 grams) minus the weight of container 78 at Time 4 (i.e., 230 grams). In another embodiment, 295 grams may be calculated as the sum of incremental changes (e.g., (525 grams−425 grams)+(425 grams−230 grams)=100 grams+195 grams=295 grams). 690 grams may be calculated as the weight of container 80 at Time 2 (i.e., 1,000 grams) minus the weight of container 80 at Time 4 (i.e., 310 grams). The identity of the food contained in containers 78 and 80 was previously determined at Time 6 of FIG. 17B. In some embodiments, food consumption can be tracked against a diet tracking system, e.g., Weight Watchers™ point counting.

If not already apparent, the meal accounting system may handle multiple modes of food consumption in which (1) the entire food item is temporarily removed from a container (or the container is temporarily removed from pressure-sensitive device 10) or (2) the food item (or container) substantially remains in place. In the former mode of consumption, a user may pick up a food item or container (e.g., pick up a glass of milk or to take a bite of a sandwich). It is then replaced with a lower weight within a (short) sample window of T second (e.g., T=5 second) so the meal accounting system associates the replaced food item or container with the one that was removed. If the removed food item (or container) is not replaced within the sample window, it may be treated as fully consumed. In the latter mode of consumption, a user may leave the food item or container in place (e.g., milk drunk through a straw or stew eaten from the plate with a fork). In either case, the changed food item or container may be identified via its new footprint (removal/replacement or reduction in place). Its weight change may be computed either via 1) the double integration of the pressure distribution of the new footprint of the identified food item or container or 2) a weight change measured by food scale 14, and applied to the identified food item or container.

FIG. 19 depicts a plurality of pressure-sensitive devices and how the pressure-sensitive devices may be utilized by a plurality of people. FIG. 19 depicts pressure-sensitive device 10*a* for the meal, pressure-sensitive device 10*b* for person 92*b* and pressure-sensitive device 10*c* for person 92*a* (e.g., two people in the family would result in a total of three pressure-sensitive devices 10*a*, 10*b*, 10*c*). While children are depicted in FIG. 19, the children's consumption of food is not being tracked; otherwise, there would be a total of five pressure-sensitive devices. Consumption per person can be tracked without user interaction with computing device 22 as long as, for example, one person at a time transfers food from pressure-sensitive device 10*a* to their pressure-sensitive device.

In another embodiment (not depicted), one pressure-sensitive device could be used for the meal and a second pressure-sensitive device could be shared among multiple users. This requires user interaction with computing device 22 to indicate which user's meal (e.g., plate and milk glass) is being measured.

In another embodiment (not depicted), one pressure-sensitive device could be used for the meal and all of the users. This is most practical if all food is allocated to the users at the start of the meal. With each (one-time) allocation, user interaction with computing device 22 indicates which user's meal is being measured. While a user can have refills, that would require subsequent user interaction with computing device 22 to indicate whose meal is having additional servings added to the meal.

FIG. 20 depicts a food item (e.g., leftovers) being transferred from a first container (e.g., My white bowl) to a second container (e.g., storage container), the second container being placed into a refrigerator, and the computing device determining an amount and identity of the food item that was placed into the second container. More specifically, at a first time instance, container 44 (e.g., bowl) and container 94 (e.g., yellow storage bowl) may be disposed on pressure-sensitive device 10. Container 44 may contain food item 60f (e.g., fall stew). Pressure-sensitive device 10 may measure the weight (=200 grams) and footprint 96a of container 94 and may measure the weight (=1,000) and footprint 46j of container 44. If container 94 had been used before, it will be recognized by its footprint and weight. As such, no user interaction with computing device 22 is needed to register container 94. If container 94 is new to computing device 22, it may be registered in a similar manner as how "My white bowl" was registered in FIG. 8. The contents of container 44 was previously determined at Time 6 of FIG. 17B.

At the second time instance, food item 60f has already been transferred from container 44 into container 94. Pressure-sensitive device 10 may measure the weight (=974 grams) and footprint 96b of container 94 and may measure the weight (=226 grams) and footprint 46a of container 44. In response to the deltas in the weights, pressure-sensitive device 10 may determine that 774 grams of food item 60f have been transferred from container 44 to container 94.

At the third time instance, container 94 has already been covered and placed into refrigerator 98. Pressure-sensitive device 10 will no longer measure footprint 96b corresponding to container 94. In response to such measurement, computing device 22 may determine that container 94 has been removed from pressure-sensitive device 10. No user interaction with computing device 22 may be required in the process of FIG. 20. In one embodiment of the invention, between the second and third time instances, the user may have an opportunity to inform computing device 22 that food is being stored in the refrigerator (or some other location) in a similar manner to the user selection of the "consume mode" above in FIG. 18. For instance, there may be an icon on computing device 22 that permits the user to enter a "store leftovers mode". If such a mode were selected, the registration of the removal of storage container 94 at or before time instance three would be further registered as the storing of storage container 94. In a similar manner, there could be a "throw away mode" that the user may select before food is thrown away, permitting computing device 22 to distinguish the disposal of food from other mechanisms in which food disappears (e.g., consumption of food, storage of food, etc.). In a similar manner, there could be a "transfer to stove mode" that the user may select before food is transferred to a pot/pan on the stove. In a similar manner, there could be a "transfer to oven mode" that the user may select before food is transferred to a pot/pan in the oven. In a similar manner to the description of the "consume mode", the user may be provided a means to exit the "store leftovers mode", "throw away mode", transfer to stove mode", and "transfer to oven mode". Each removal of a food item from pressure-sensitive device 10 (whether it may be the result of consumption, storage, cooking on the stovetop, etc.) may be registered in local food library 27 along with a description of the removal (consumption, storage, cooking, etc.). Anytime a food item is removed as part of the "consume mode", that food item may be tagged in local food library 27 as being consumed and further may be tagged with additional attributes (when, by whom, . . . ). Anytime a food item is transferred as part of the "throw away mode", that food item may be removed from local food library 27 or tagged as being discarded.

To eat the leftovers, the user may take container 94 out of refrigerator 98. If it is to be microwaved in that container (or eaten cold), the process follows FIGS. 17A, 17B and 18. The cover from container 94 should be removed before placing container 94 on pressure-sensitive device 10. Otherwise, it may be tracked in a similar manner to how cover 48 was tracked in FIG. 10.

If the food is moved into container 44 to serve or heat, the process of FIG. 20 may be performed in reverse. No user interaction with computing device 22 is required because the footprint and weight of the containers are already registered.

FIG. 21 depicts the computing device recording the amount and identity of a food item that is initially present and that is subsequently consumed during a plurality of meals, in accordance with one embodiment of the invention. Before lunch 1, container 38 may be disposed on pressure-sensitive device 10. Based on the weight (=500 grams) and footprint 40a of container 38, computing device 22 may identify the container to contain peanut butter.

After lunch 1, container 38 may again be disposed on pressure-sensitive device 10. Pressure-sensitive device 10 may measure the weight (=400 grams) and footprint 40b of container 38. Based on the outline of footprint 40b equaling footprint 40a, computing device 22 may determine that container 38 is the same container that was registered prior to lunch 1. The decrease in weight may be inferred by computing device 22 to be the result of the consumption of 100 grams of the food item from container 38 during lunch 1.

After lunch 2, container 38 may again be disposed on pressure-sensitive device 10. Pressure-sensitive device 10 may measure the weight (=200 grams) and footprint 40c of container 38. Based on the outline of footprint 40c equaling footprint 40a and/or 40b, computing device 22 may determine that container 38 is the same container that was registered prior to or after lunch 1. The decrease in weight may be inferred by computing device 22 to be the result of the consumption of 200 grams of the food item from container 38 during lunch 2.

After lunch 3, container 38 may again be disposed on pressure-sensitive device 10. Pressure-sensitive device 10 may measure the weight (=50 grams) and footprint 40d of container 38. Based on the outline of footprint 40d equaling footprint 40a, 40b and/or 40c, computing device 22 may determine that container 38 is the same container that was registered prior to or after lunch 1, or after lunch 2. The decrease in weight may be inferred by computing device 22 to be the result of the consumption of 150 grams of the food item from container 38 during lunch 3. Computing device 22 may additionally determine the weight of container 38 to be substantially equal to the empty weight of the container based on information determined in association with FIG. 6.

Figure 22:
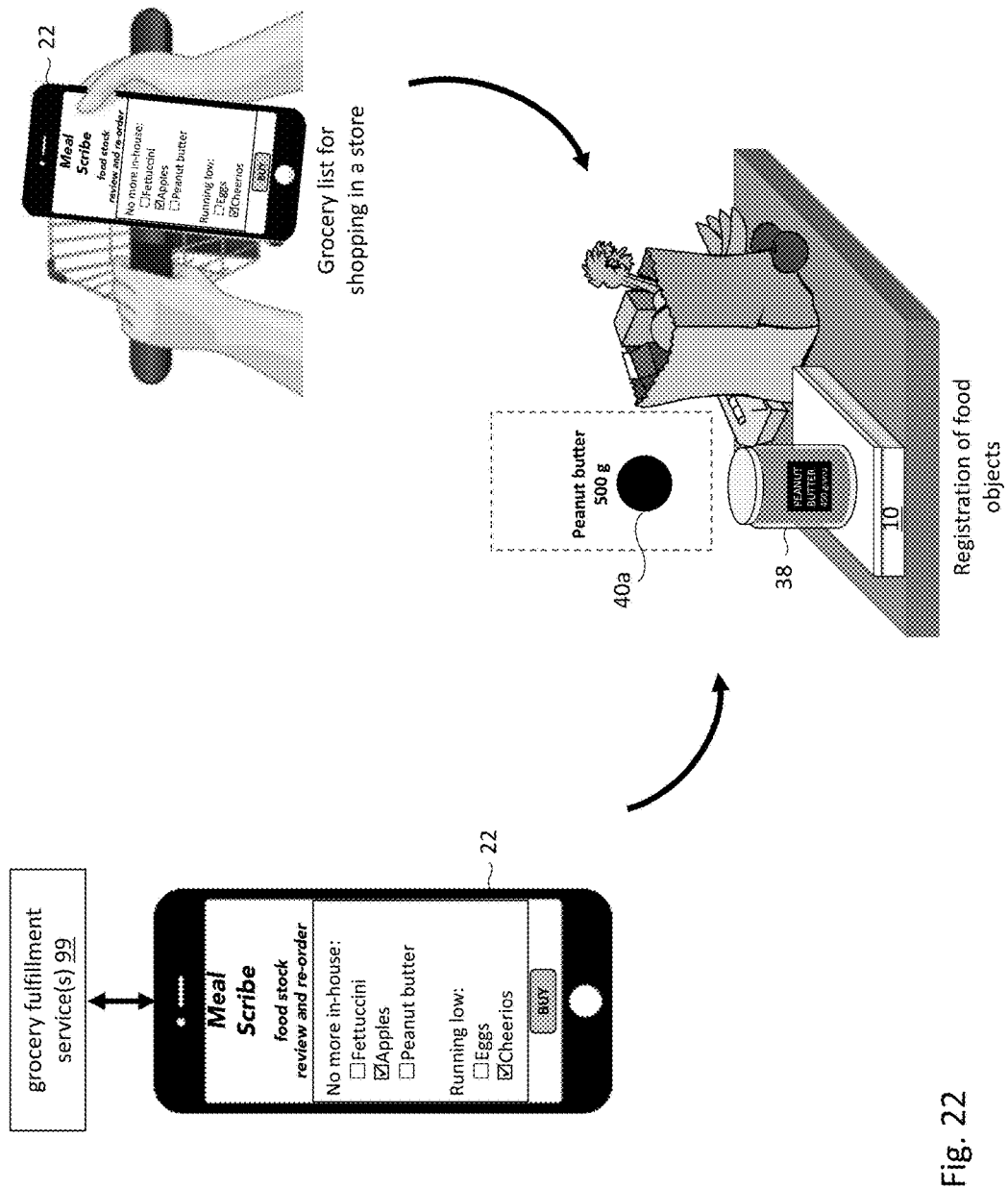
FIG. 22 depicts the computing device being used to order food items (or being used to provide a shopping list to assist a user with his/her purchasing of food items in a store) and the registration of the food items that were ordered or purchased, in accordance with one embodiment of the invention.

FIG. 22 depicts the computing device being used to order food items (or being used to provide a shopping list to assist a user with his/her purchasing of food items in a store) and the registration of the food objects that were ordered or purchased. Because the meal accounting system tracks the consumption of any registered food item, replenishment can be triggered by computing device 22 communicating a request for a food item from grocery fulfillment service(s) 99. Amazon Dash™ is an example of an automatic replenishment grocery fulfillment service, while Amazon Fresh™, Peapod™ and Safeway—Fresh to Your Door™ are examples of services which allow a user to manually order groceries online. Computing device 22 may present a list of food items that are running low or which have run out. Such list may be used as a grocery list when a user is shopping in a grocery store or when shopping online. Whether food items are acquired via automatic replenishment, ordered online, purchased from a grocery store or another process (e.g., grown in a garden), the food items may be registered when the food items are used in a meal preparation process, when the food items are acquired, or when they are unpacked at home after being delivered or purchased from a grocery store. The registration process may be performed automatically, in which the pressure sensitive device 10 and computing device 22 may automatically determine and store the identity of the food item, or may performed manually, in which a user determines the identity of the food item and provides such identity to computing device 22 and/or pressure sensitive device 10.

Figure 23:
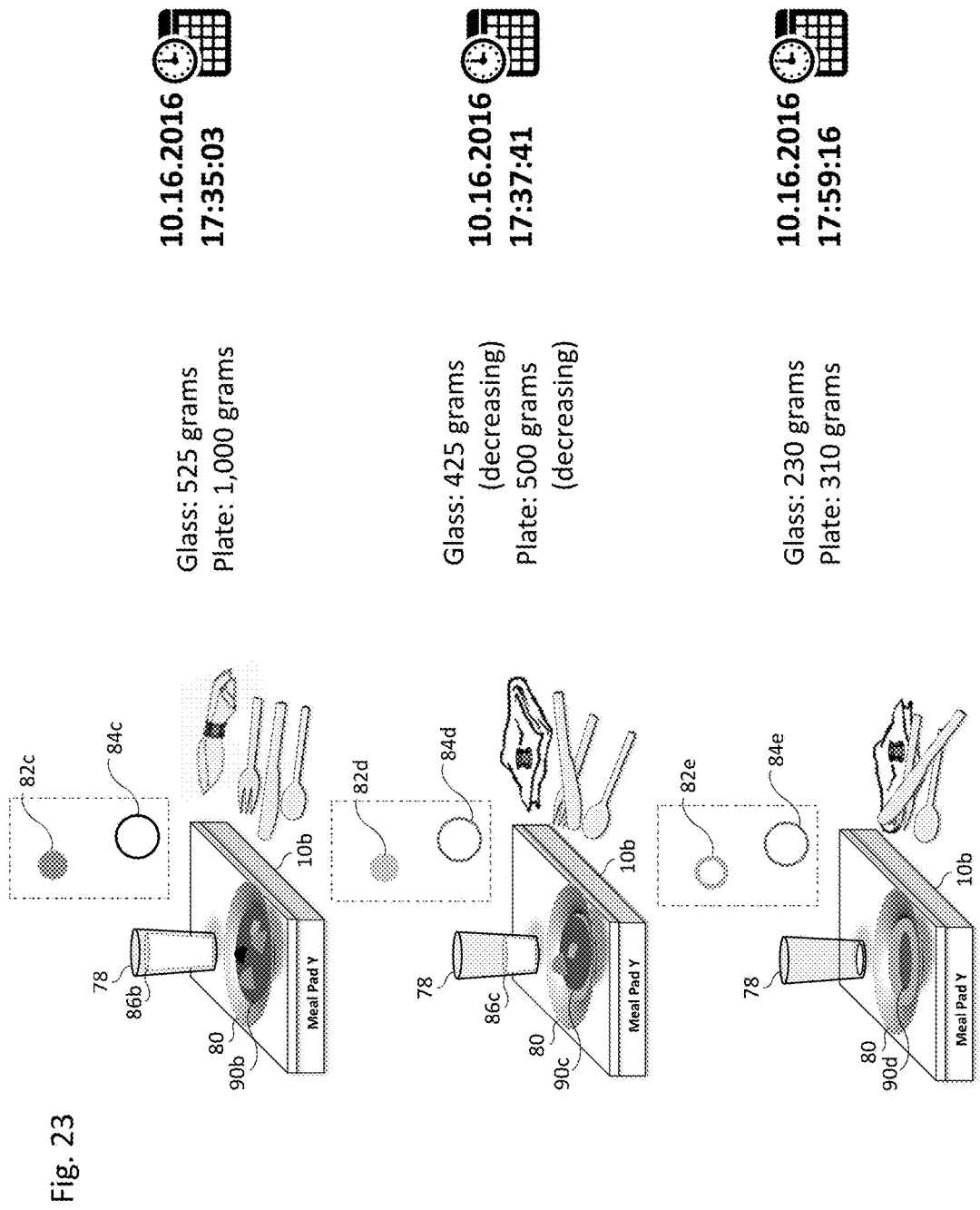
FIG. 23 depicts a computing device recording the amount of each of a plurality of food items that are remaining (or are consumed) at various time points during the consumption of a meal, in accordance with one embodiment of the invention.

FIG. 23 depicts the computing device recording the amount of each of a plurality of food items that are remaining (or are consumed) at various time points during a meal, in accordance with one embodiment of the invention. More generally, the meal accounting system may record the timestamp of each measurable event. For example, when "Consume" mode is on (FIG. 18), the time of each food consumption event may be recorded. It can be very valuable to know the nutritional content of exactly what was consumed when, especially when correlated with daily weight changes and physical activity as may be recorded by, for example, fitness trackers (e.g., FitBit™). These correlations may expose nuanced correlations, i.e., far beyond "avoid midnight snacks" between a person's food consumption and his or her weight. The correlations may provide important diet and exercise feedback to individuals who wish to achieve a target weight or other food-based goal. The correlations may also provide important nutrient and micronutrient information and may, in some instances, provide suggestions as to the types of food the individual may want to consume to overcome a possible deficiency. Feasibility of this feature may require data mining of meal accounting+fitness+weight records.

Figure 24:
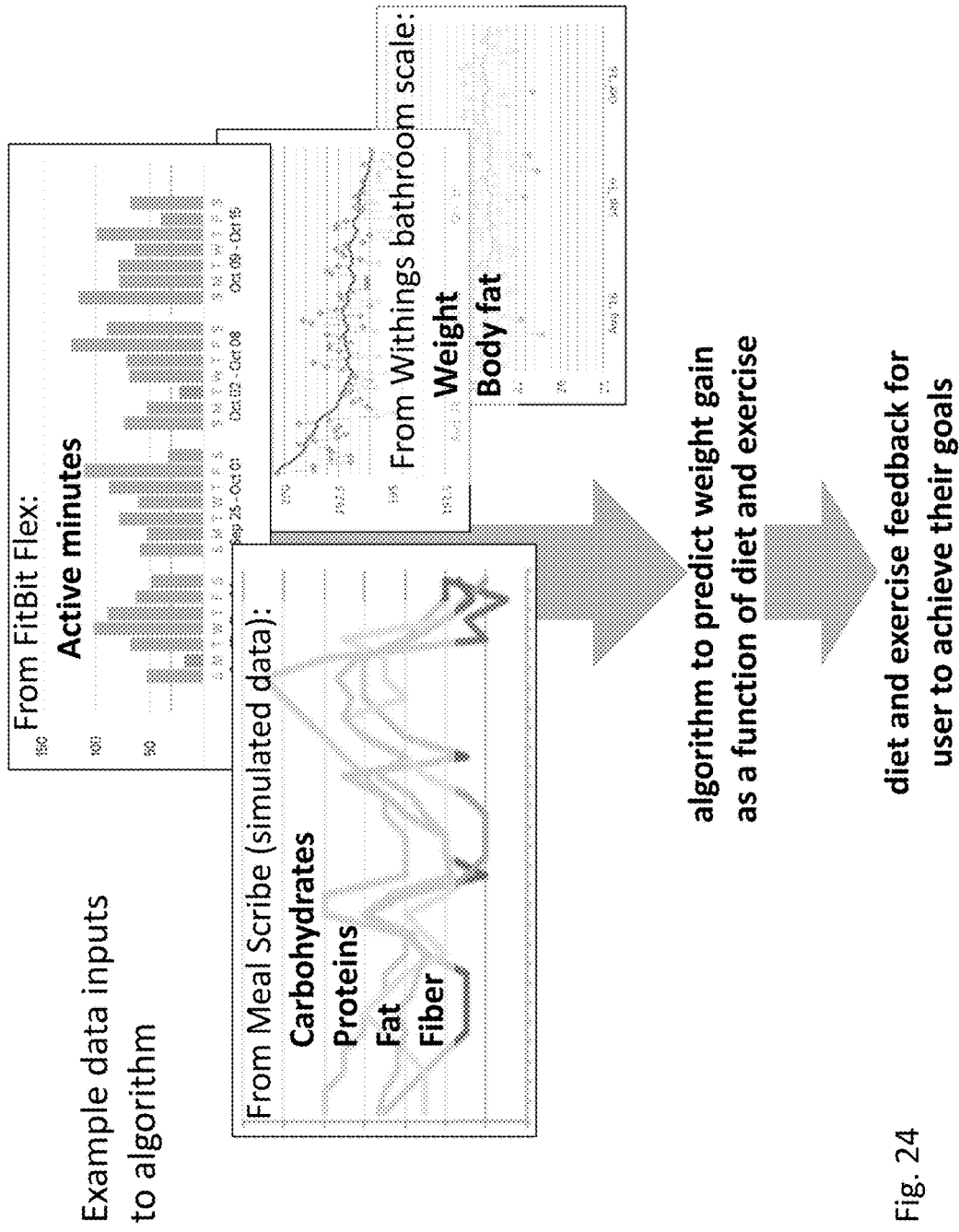
FIG. 24 depicts example data inputs for an algorithm that predicts weight gain as a function of diet and exercise, in accordance with one embodiment of the invention.

FIG. 24 depicts example data inputs for an algorithm that predicts weight gain as a function of diet and exercise, in accordance with one embodiment of the invention. Example data inputs to the algorithm may include measurements tracked by the meal accounting system (e.g., the amount of carbohydrates, protein, fat and fiber over time). Example data inputs may also include a degree of physical activity, as monitored by a Fitbit Flex™. Example data inputs may also include measurements of an individual's weight and body fat, as monitored by a Nokia Body+™ bathroom scale. Based on these inputs, an algorithm may predict an individual's weight over the next month, next year, etc. Diet and exercise feedback may be provided to the user to assist the user in achieving his/her goals.

Figure 25:
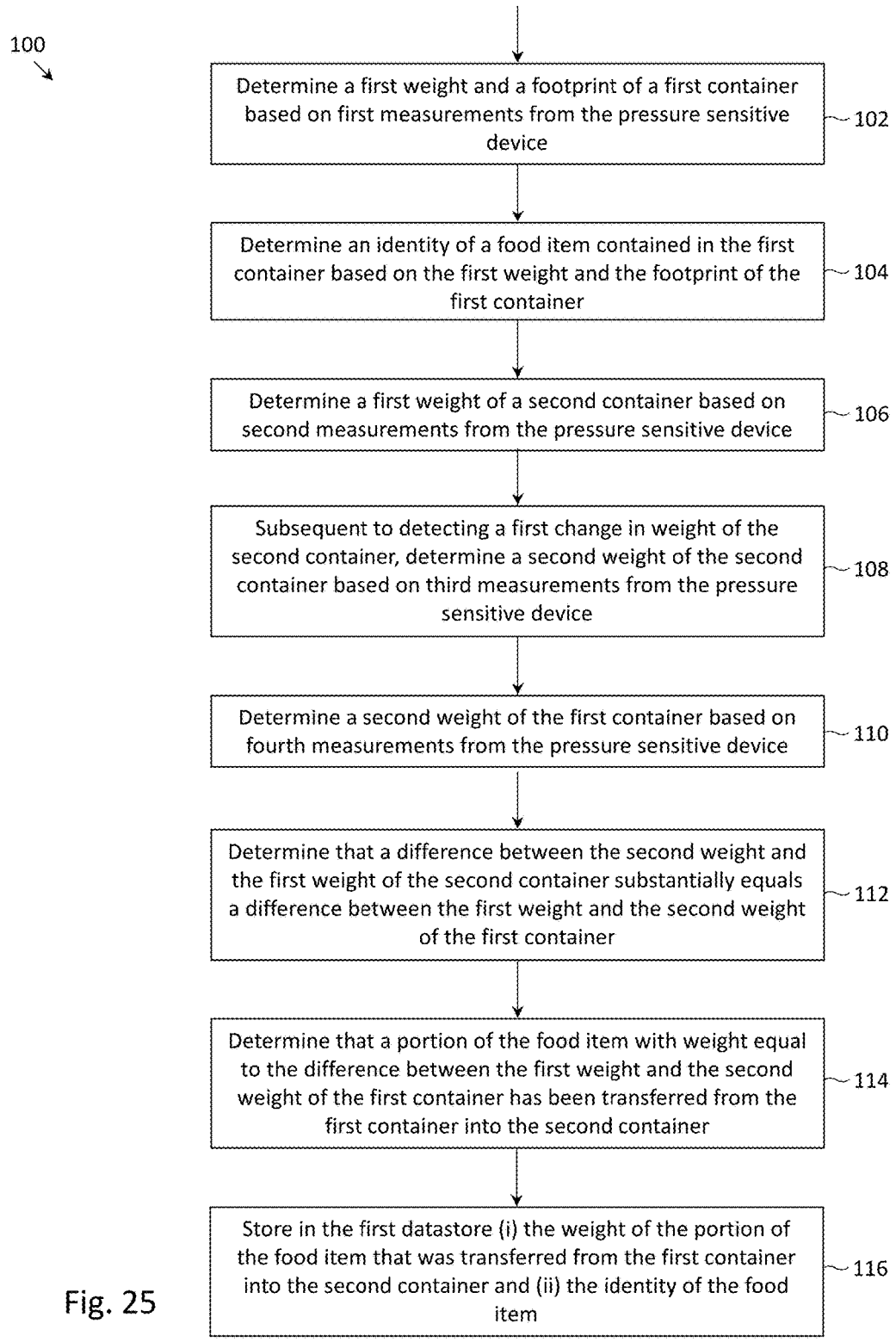
FIG. 25 depicts a flowchart of a process for determining an identity and a weight of a portion of a food item that is transferred from a first container into a second container, in accordance with one embodiment of the invention.

FIG. 25 depicts flowchart 100 of a process for determining an identity and a weight of a portion of a food item that is transferred from a first container into a second container, in accordance with one embodiment of the invention. At step 102, computing device 22 may determine a first weight and a footprint of a first container based on first measurements from the pressure-sensitive device. An example of such step was provided above in FIG. 17A with computing device 22 determining the first weight (=4,000 grams) and the footprint 76a of container 74.

At step 104, computing device 22 may determine an identity of a food item contained in the first container based on the first weight and the footprint of the first container. An example of such step was provided above in FIG. 17A with computing device 22 determining container 74 to contain milk.

At step 106, computing device 22 may determine a first weight of a second container based on second measurements from the pressure-sensitive device. An example of such step was provided above in FIG. 17A with computing device 22 determining a first weight (=225 grams) of container 78.

At step 108, subsequent to detecting a first change in weight of the second container, computing device 22 may determine a second weight of the second container based on third measurements from the pressure-sensitive device. An example of such step was provided above in FIG. 17A with computing device 22 determining a second weight (=525 grams) of container 78.

At step 110, computing device 22 may determine a second weight of the first container based on fourth measurements from the pressure-sensitive device. An example of such step was provided above in FIG. 17A with computing device 22 determining a second weight (=3,700 grams) of container 74.

At step 112, computing device 22 may determine that a difference between the second weight and the first weight of the second container (525−225=300 grams) substantially equals a difference between the first weight and the second weight of the first container (4,000−3,700=300 grams).

At step 114, computing device 22 may determine that a portion of the food item with weight equal to the difference between the first weight and the second weight of the first container has been transferred from the first container into the second container. An example of such step was provided above in FIG. 17A with computing device 22 determining that 300 grams of milk was transferred from container 74 to container 78.

At step 116, computing device 22 may store in the first datastore an association between (i) an amount of the portion of the food item that was transferred from the first container into the second container and (ii) the identity of the food item. An example of such step was provided above in FIG. 17A with computing device 22 storing in local food library 27 that 300 grams of milk have been transferred into container 78. In some instances, the amount of the portion of the food item that was transferred from the first container into the second container may be equal to the weight of the portion of the food item that was transferred from the first container into the second container. In other instances, there may be a conversion from the weight of the food item into an amount of the food item (e.g., 300 grams of milk=1.27 cups of milk).

Figure 26:
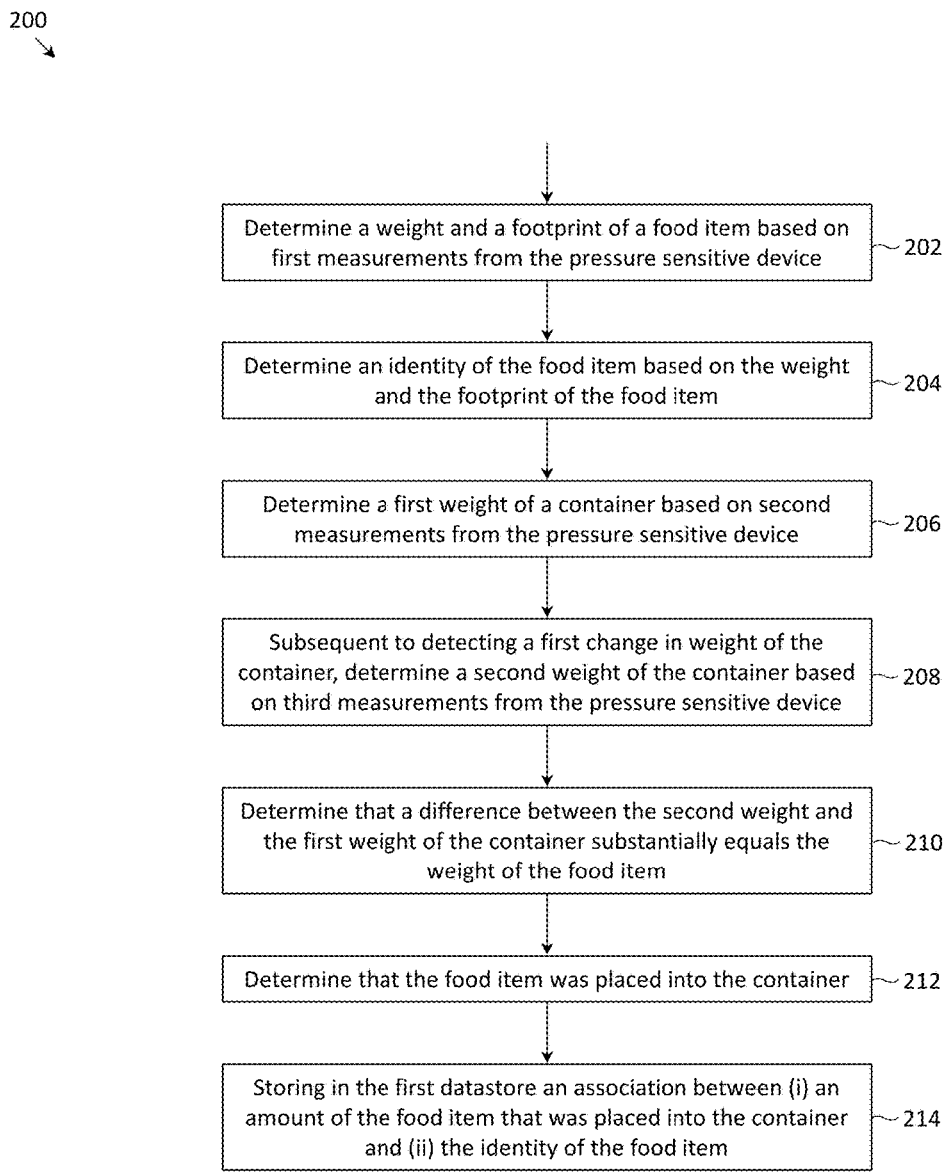
FIG. 26 depicts a flowchart of a process for determining an identity and a weight of a food item that is placed into a container, in accordance with one embodiment of the invention.

FIG. 26 depicts flowchart 200 of a process for determining an identity and a weight of a food item that is placed into a container, in accordance with one embodiment of the invention. At step 202, computing device 22 may determine a weight and a footprint of a food item based on first measurements from the pressure-sensitive device. An example of such step was provided above in FIG. 13A with computing device 22 determining the weight (=90 grams) and a footprint of food item 58 based on measurements from pressure-sensitive device 10.

At step 204, computing device 22 may determine an identity of the food item based on the weight and the footprint of the food item. An example of such step was provided above in FIG. 13A with computing device 22 determining the food item to be two eggs based on the weight and the footprint of the food item.

At step 206, computing device 22 may determine a first weight of a container based on second measurements from the pressure-sensitive device. An example of such step was provided above in FIG. 13A with computing device 22 determining the weight of container 44 to be 1,725 grams.

At step 208, computing device 22 may, subsequent to detecting a first change in weight of the container, determine a second weight of the container based on third measurements from the pressure-sensitive device. An example of such step was provided above in FIG. 13B with computing device 22 determining the weight of container 44 to be 1,805 grams.

At step 210, computing device 22 may determine that a difference between the second weight and the first weight of the container substantially equals the weight of the food item. An example of such step was provided above in FIG. 13B with computing device 22 determining the difference between the second weight and the first weight of the container (1,805−1,725=80 grams) substantially equals the weight of the food item (90 grams).

At step 212, computing device 22 may determine that the food item was placed into the container. An example of such step was provided above in FIG. 13B with computing device 22 determining that two eggs were placed into container 44.

At step 214, computing device 22 may store in the first datastore an association between (i) an amount of the food item that was placed into the container and (ii) the identity of the food item. An example of such step was provided above in FIG. 13B with computing device 22 storing in local food library that two eggs were placed into container 44.

Figure 27:
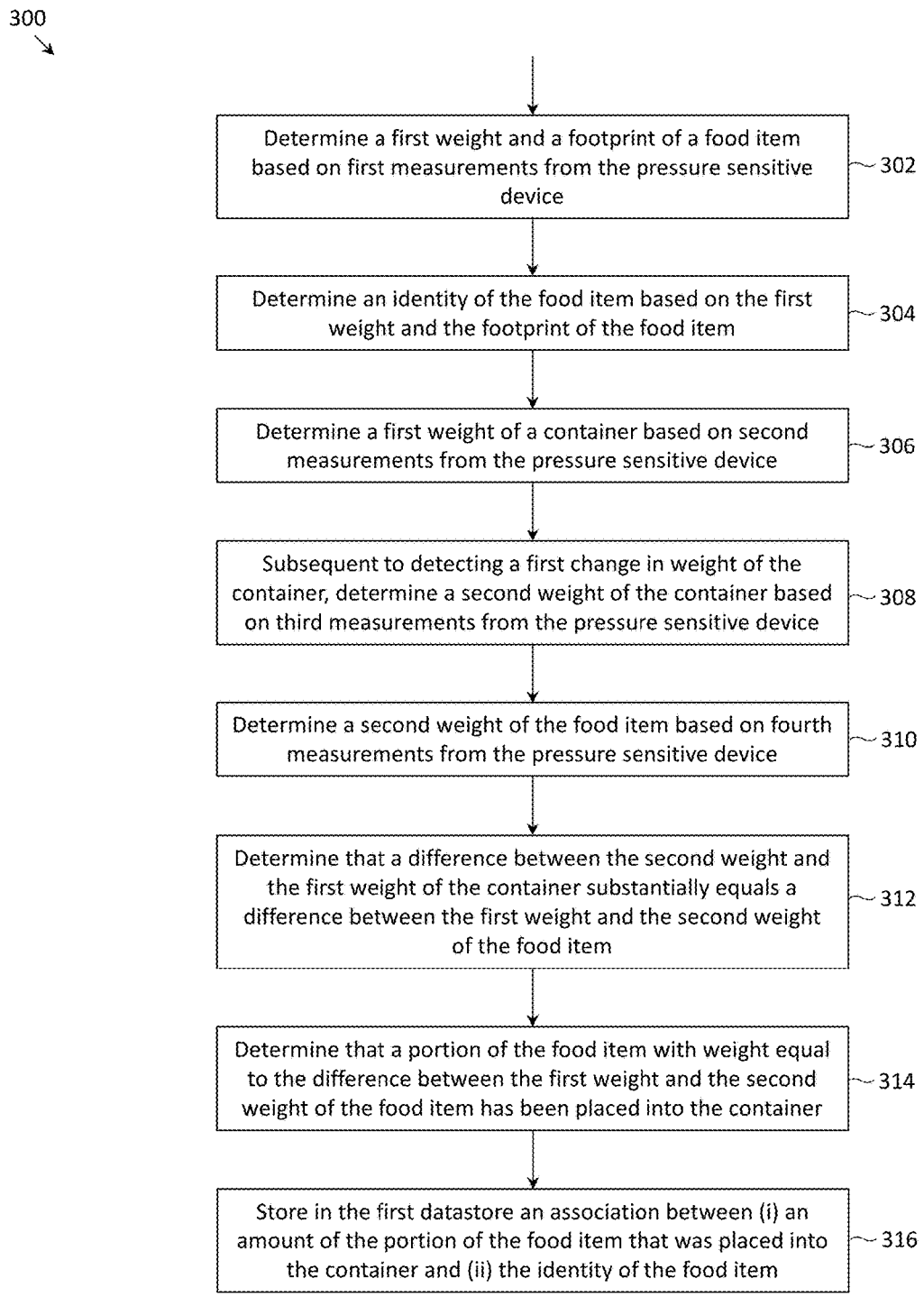
FIG. 27 depicts a flowchart of a process for determining an identity and a weight of a portion of a food item that is placed into a container, in accordance with one embodiment of the invention.

FIG. 27 depicts flowchart 300 of a process for determining an identity and a weight of a portion of a food item that is placed into a container, in accordance with one embodiment of the invention. At step 302, computing device 22 may determine a first weight and a footprint of a food item based on first measurements from the pressure-sensitive device. An example of such step was provided above in step A of FIG. 15 in which the weight and footprint of food item 66 was determined based on measurements from pressure-sensitive device 10.

At step 304, computing device 22 may determine an identity of the food item based on the first weight and the footprint of the food item. An example of such step was provided above in step A of FIG. 15 in which the identity of food item 66 was determined to be a cucumber based on the weight and footprint of food item 66.

At step 306, computing device 22 may determine a first weight of a container based on second measurements from the pressure-sensitive device. An example of such step was provided above in step F of FIG. 15 in which the weight of container 44 was determined based on measurements from pressure-sensitive device 10.

At step 308, computing device 22 may subsequent to detecting a first change in weight of the container, determine a second weight of the container based on third measurements from the pressure-sensitive device. An example of such step was provided above in step G of FIG. 15 in which the second weight of container 44 was determined based on measurements from pressure-sensitive device 10.

At step 310, computing device 22 may determine a second weight of the food item based on fourth measurements from the pressure-sensitive device. An example of such step was provided above in step G of FIG. 15 in which the second weight of the cucumber was determined based on measurements from pressure-sensitive device 10.

At step 312, computing device 22 may determine that a difference between the second weight and the first weight of the container substantially equals a difference between the first weight and the second weight of the food item. An example of such step was provided above in step G of FIG. 15 in which computing device 22 determined that the difference between the second weight and the first weight of the container 44 is substantially equal to a difference between the first weight and the second weight of the cucumber.

At step 314, computing device 22 may determine that a portion of the food item with weight equal to the difference between the first weight and the second weight of the food item has been placed into the container. An example of such step was provided above in step G of FIG. 15 in which computing device 22 determined that a portion of the cucumber with weight equal to the difference between the first weight and the second weight of the cucumber had been placed into container 44.

At step 316, computing device 22 may store in the first datastore an association between (i) an amount of the portion of the food item that was placed into the container and (ii) the identity of the food item. An example of such step was provided above in step G of FIG. 15 in which computing device 22 stored in local food library 27 that, for example, 100 grams of the cucumber had been transferred into container 44.

Figure 28:
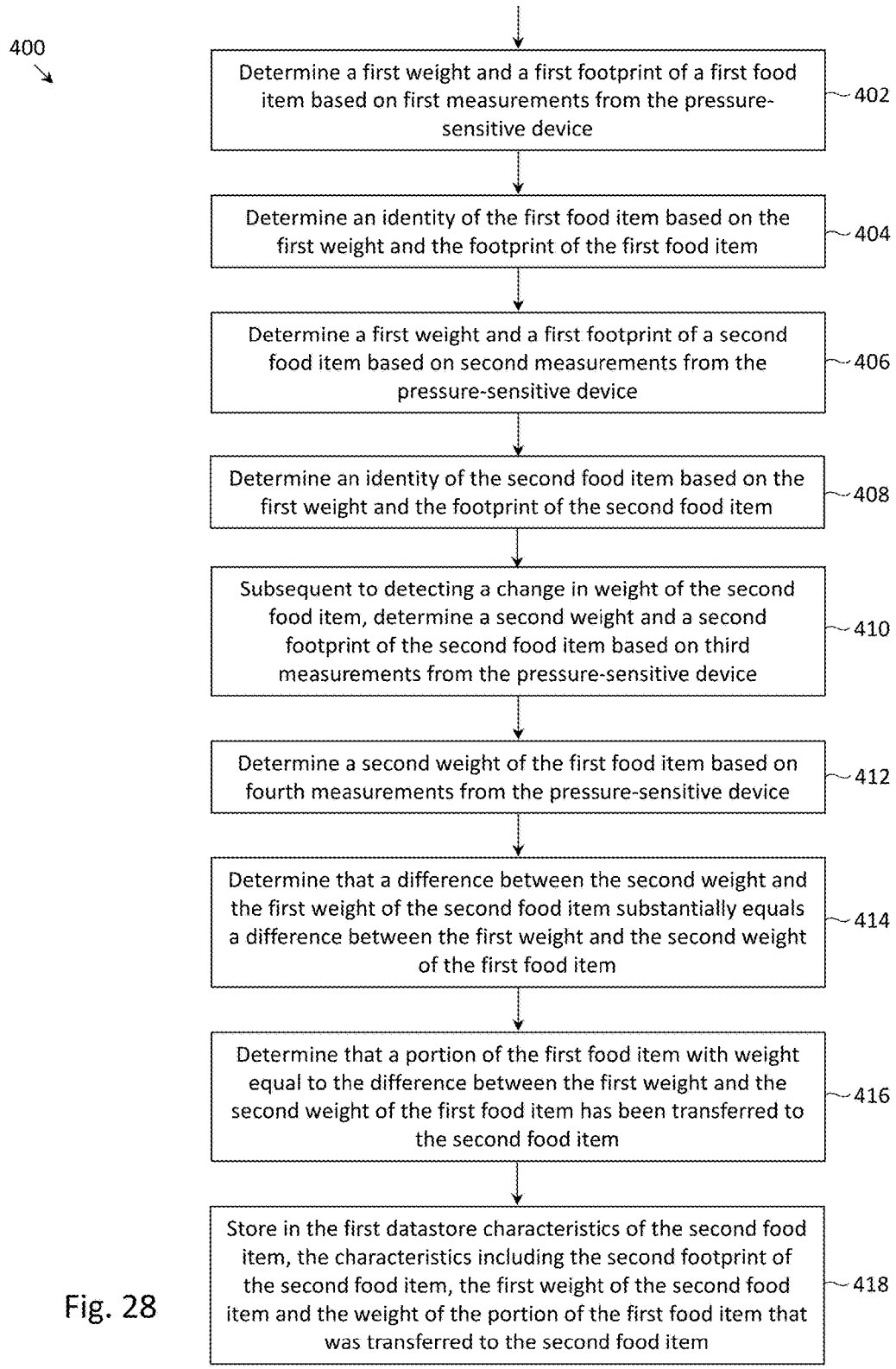
FIG. 28 depicts a flowchart of a process for determining an identity and a weight of a portion of a food item that is transferred from one food item to another food item, in accordance with one embodiment of the invention.

FIG. 28 depicts flowchart 400 of a process for determining an identity and a weight of a portion of a food item that is transferred from one food item to another food item, in accordance with one embodiment of the invention. At step 402, computing device 22 may determine a first weight and a first footprint of a first food item based on first measurements from the pressure-sensitive device. An example of such step was provided above in FIG. 11 with computing device 22 determining the first weight (=74 grams) and footprint 152a of food item 150 based on first measurements from pressure-sensitive device 10.

At step 404, computing device 22 may determine an identity of the first food item based on the first weight and the first footprint of the first food item. An example of such step was provided above in FIG. 11 in which computing device 22 determined food item 150 to be Brie cheese based on the first weight and footprint 152a of food item 150.

At step 406, computing device 22 may determine a first weight and a first footprint of a second food item based on second measurements from the pressure-sensitive device. An example of such step was provided above in FIG. 11 with computing device 22 determining the first weight (=3 grams) and footprint 156a of food item 154 based on the second measurements from pressure-sensitive device 10.

At step 408, computing device 22 may determine an identity of the second food item based on the first weight and the first footprint of the second food item. An example of such step was provided above in FIG. 11 in which computing device 22 determined food item 154 to be a cracker based on the first weight and footprint 156a of food item 154.

At step 410, subsequent to detecting a change in weight of the second food item, computing device 22 may determine a second weight and a second footprint of the second food item based on third measurements from the pressure-sensitive device. An example of such step was provided above in FIG. 11 with computing device 22 determining the second weight (=13 grams) and footprint 156b of food item 154 (in combination with food item 150b) based on third measurements from the pressure-sensitive device.

At step 412, computing device 22 may determine a second weight of the first food item based on fourth measurements from the pressure-sensitive device. An example of such step was provided above in FIG. 11 with computing device 22 determining the second weight (=64 grams) and footprint 152*b* of food item 150*a* based on fourth measurements from pressure-sensitive device 10.

At step 414, computing device 22 may determine that a difference between the second weight and the first weight of the second food item (13 grams−3 grams=10 grams) substantially equals a difference between the first weight and the second weight of the first food item (74 grams−64 grams=10 grams).

At step 416, computing device 22 may determine that a portion of the first food item with weight equal to the difference between the first weight and the second weight of the first food item has been transferred to the second food item. An example of such step was provided above in FIG. 11 with computing device 22 determining that 10 grams of food item 150 was transferred to food item 154.

At step 418, computing device 22 may store in the first datastore characteristics of the second food item, the characteristics including the second footprint of the second food item, the first weight of the second food item and the weight of the portion of the first food item that was transferred to the second food item. In the example of FIG. 11, local food library 27 may store footprint 156*b* of food item 154 (in combination with food item 150*b*), the first weight of the food item 154 (=3 grams), and the weight of the portion 150*b* of the food item (=10 grams) that was transferred to food item 154. More generally, the constituents of a meal (weight and/or type of each of the constituents) may be stored, along with the footprint of the meal. If not already apparent, the composition of "a food item" may change over time. At the second time instance, the second food item included cracker 154, while at the third time instance, the second food item included cracker 154 and Brie cheese 150*b*.

Figure 29:
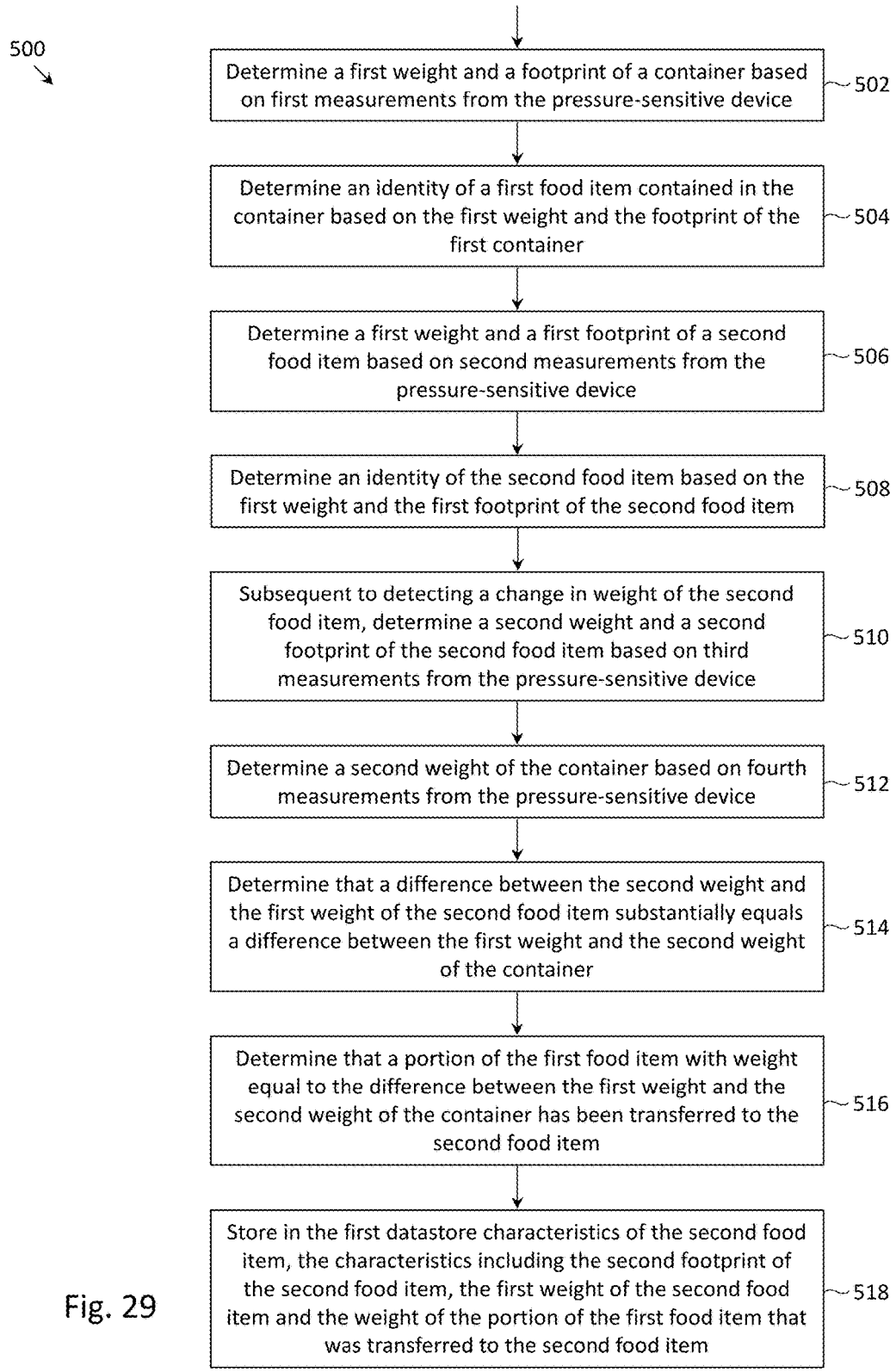
FIG. 29 depicts a flowchart of a process for determining an identity and a weight of a portion of a food item that is transferred from a container to a food item, in accordance with one embodiment of the invention.

FIG. 29 depicts flowchart 500 of a process for determining an identity and a weight of a portion of a food item that is transferred from a container to a food item, in accordance with one embodiment of the invention. At step 502, computing device 22 may determine a first weight and a footprint of a container based on first measurements from the pressure-sensitive device. An example of such step was provided above in FIG. 12 in which computing device 22 determined the first weight (=400 grams) and footprint 174*a* of container 170 based on first measurements from pressure-sensitive device 10.

At step 504, computing device 22 may determine an identity of a first food item contained within the container based on the first weight and the footprint of the first container. An example of such step was provided above in FIG. 12 with computing device 22 determining peanut butter to be contained within container 170 based on the first weight and the footprint of container 170.

At step 506, computing device 22 may determine a first weight and a first footprint of a second food item based on second measurements from the pressure-sensitive device. An example of such step was provided above in FIG. 12 in which computing device 22 determined the first weight (=29 grams) and footprint 180*a* of food item 178 based on second measurements from pressure-sensitive device 10.

At step 508, computing device 22 may determine an identity of the second food item based on the first weight and the first footprint of the second food item. An example of such step was provided above in FIG. 12 in which computing device 22 determined food item 178 to be a piece of bread based on the first weight and footprint 180*a* of food item 178.

At step 510, subsequent to detecting a change in weight of the second food item, computing device 22 may determine a second weight and a second footprint of the second food item based on third measurements from the pressure-sensitive device. An example of such step was provided above in FIG. 12 in which computing device 22 determined the second weight (=40 grams) and footprint 180*b* of food item 178 (in combination with food item 182) based on third measurements from pressure-sensitive device 10.

At step 512, computing device 22 may determine a second weight of the container based on fourth measurements from the pressure-sensitive device. An example of such step was provided above in FIG. 12 in which computing device 22 determined the second weight (=360 grams) and footprint 174*b* of food item 170 based on fourth measurements from pressure-sensitive device 10.

At step 514, computing device 22 may determine that a difference between the second weight and the first weight of the second food item (69 grams−29 grams=40 grams) substantially equals a difference between the first weight and the second weight of the container (400 grams−360 grams=40 grams).

At step 516, computing device 22 may determine that a portion of the first food item with weight equal to the difference between the first weight and the second weight of the container has been transferred to the second food item. An example of such step was provided above in FIG. 12 with computing device 22 determining that 40 grams of the food item contained within container 170 was transferred to food item 178.

At step 518, computing device 22 may store in the first datastore characteristics of the second food item, the characteristics including the second footprint of the second food item, the first weight of the second food item, and the weight of the portion of the first food item that was transferred to the second food item. In the example of FIG. 12, local food library 27 may store footprint 180*b* of food item 178 (in combination with food item 182), the first weight of food item 178 (=29 grams) and the weight of the portion of the food item contained within container 170 (=40 grams) that was transferred to the food item 178. More generally, the constituents of a meal (weight and/or type of each of the constituents) may be stored, along with the footprint of the meal. If not already apparent, the composition of "a food item" may change over time. At the second time instance, the second food item included bread 178, while at the third time instance, the second food item included bread 178 and peanut butter 182.

Figure 30:
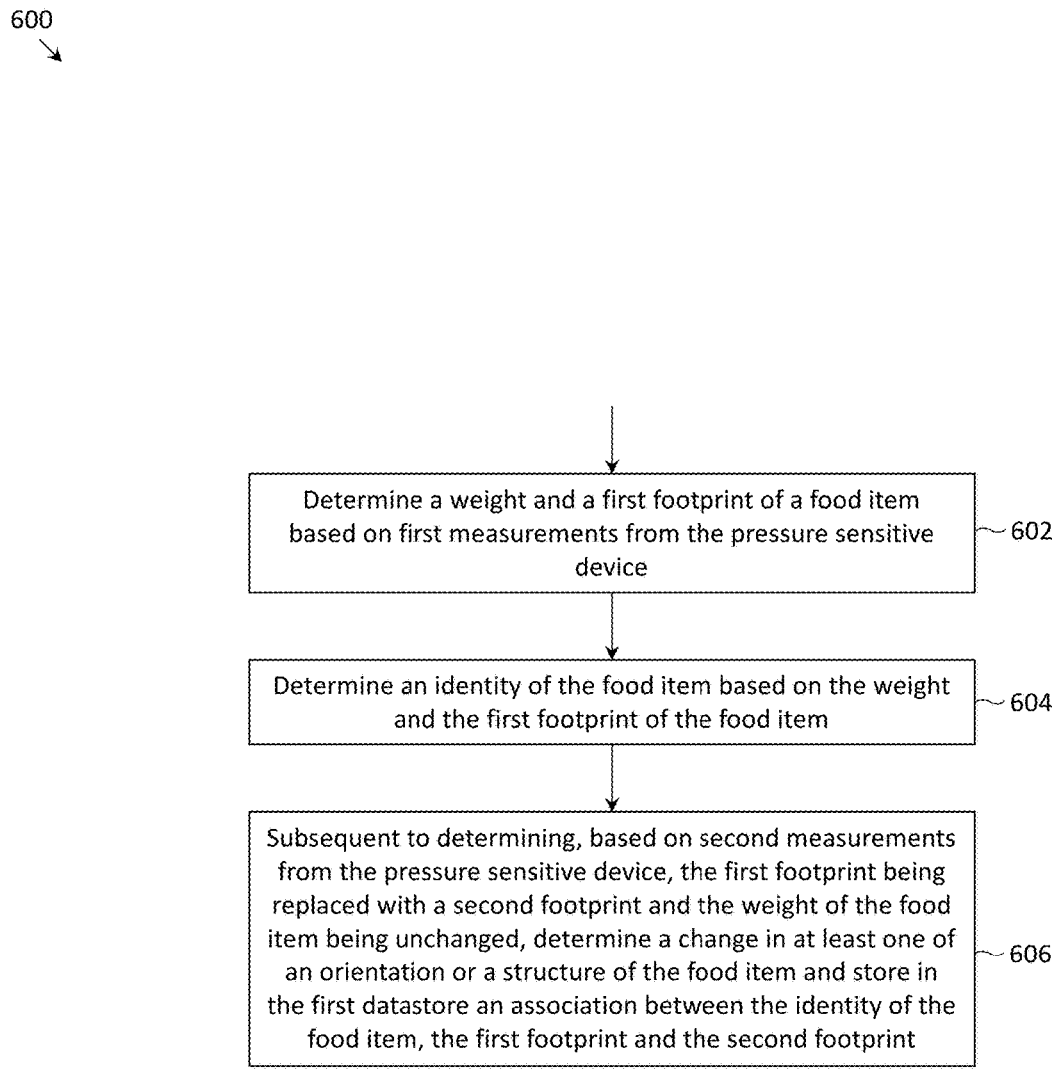
FIG. 30 depicts a flowchart of a process for associating a plurality of footprints with a single food item, in accordance with one embodiment of the invention.

FIG. 30 depicts a flowchart of process 600 for associating a plurality of footprints with a single food item, in accordance with one embodiment of the invention. At step 602, computing device 22 may determine a weight and a first footprint of a food item based on first measurements from the pressure-sensitive device. An example of such step was provided above in step A of FIG. 15 in which a weight and a first footprint of food item 66 was determined based on measurements from pressure-sensitive device 10.

At step 604, computing device 22 may determine an identity of the food item based on the weight and the first footprint of the food item. An example of such step was provided above in step A of FIG. 15 in which the identity of food item 66 was determined to be a cucumber based on the weight and footprint of food item 66.

At step 606 computing device 22 may subsequent to determining, based on second measurements from the pressure-sensitive device, the first footprint being replaced with a second footprint and the weight of the food item being unchanged, determine a change in at least one of an orientation or a structure of the food item and store in the first datastore an association between the identity of the food item, the first footprint and the second footprint. An example of such step was provided above in step E of FIG. 15 in which computing device 22 determined that the weight of food item was unchanged between steps A and E, but the footprint of food item 66 in step A had been replaced with the footprint of food item 66 in step E. Subsequent to these determinations, computing device 22 determined that a portion of food item 66 had been sliced, and stored in local food library 27 an association between the identity of the food item (i.e., cucumber), the footprint of food item 66 from step A and the footprint of the food item 66 from step E. The steps of FIG. 28 are also illustrated by the process of FIG. 5 in which various orientations of a food item were registered with an identity of the food item.

Figure 31:
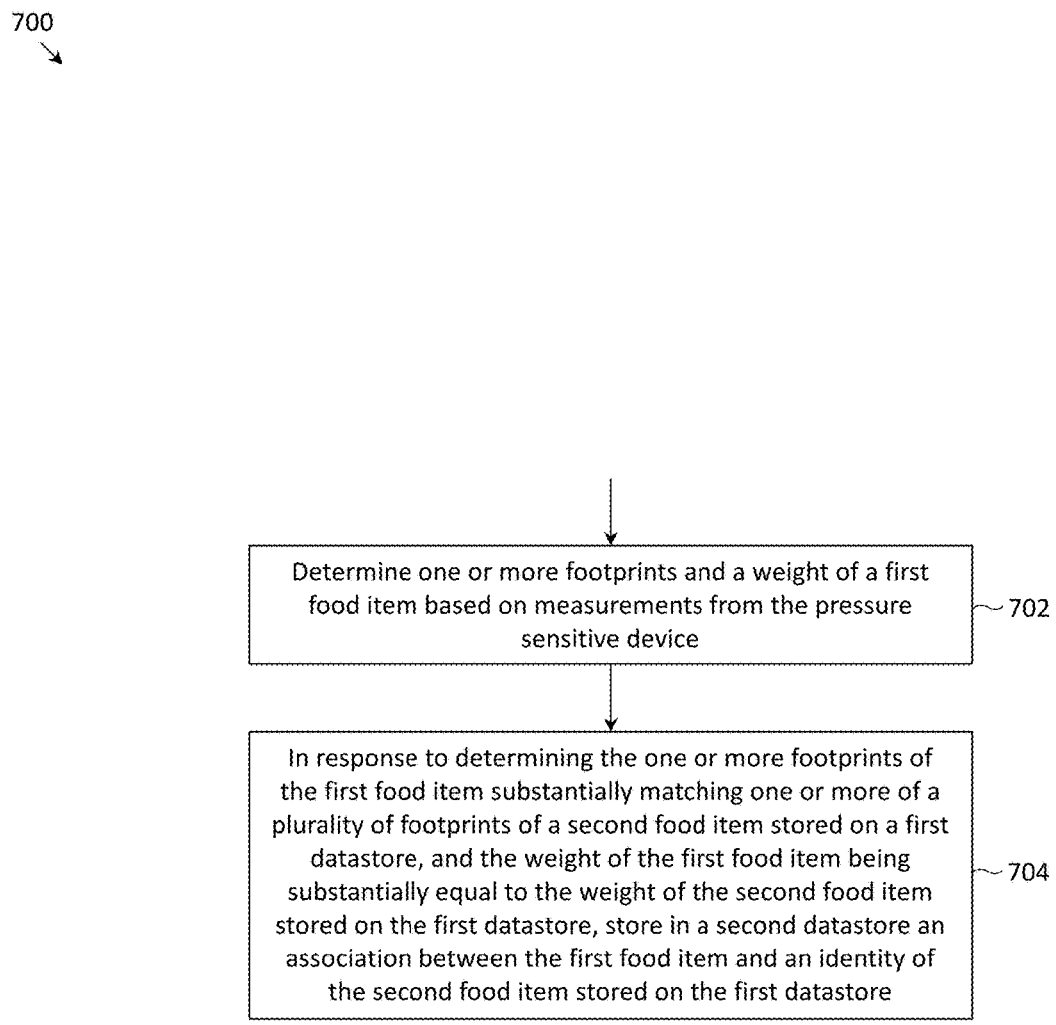
FIG. 31 depicts a flowchart of a process for determining an identity of a food item, in which the one or more footprints of the food item matches one or more of a plurality of footprints on record for the food item, in accordance with one embodiment of the invention.

FIG. 31 depicts a flowchart of process 700 for determining an identity of a food item, in which the one or more footprints of the food item matches one or more of a plurality of footprints on record for the food item, in accordance with one embodiment of the invention. At step 702, computing device 22 may determine one or more footprints and a weight of a first food item based on measurements from the pressure-sensitive device. In the example of FIG. 5, suppose the three footprints 36a, 36b and 36c and weight of 397 grams were already associated with food item 32 in global food library 28. At a later point in time, suppose an unknown food item were placed on pressure-sensitive device 10. Pressure-sensitive device 10 would determine one or more footprints and weight of the unknown food item.

At step 704, computing device 22 may in response to determining the one or more footprints of the first food item substantially matching one or more of a plurality of footprints of a second item stored on a first datastore, and the weight of the first food item being substantially equal to the weight of the second food item stored on the first datastore, store in a second datastore an association between the first food item and an identity of the second food item stored on the first datastore. In the example of FIG. 5, suppose computing device 22 determines the footprint of the unknown food item to substantially match footprint 36c, and the weight of unknown food item to substantially equal to the weight of food item 32. In response to such determinations, computing device 22 may store in local food library 27 an association between the unknown food item and the identity of food item 32.

As one example of how multiple footprints of a food item may be used to identify the food item, the user might first place a food item in the configuration of "Footprint 1" in FIG. 5. Computing system 22 may reply with a ranked list of possible matching food items. The user could then speak the food item name, scan a bar code, or place the food item in the configuration of "Footprint 2" in FIG. 5. Such action may narrow the search result down to one likely match (no user feedback needed) or, if there are still multiple possible matches, the user may place the food item in the configuration of "Footprint 3", etc. The advantage of an identification process involving more than one footprint is that the user is allowed to perform one kind of action (i.e., placing the item on the pressure-sensitive device 10) and is not required to speak, scan a barcode, etc.

Figure 32:
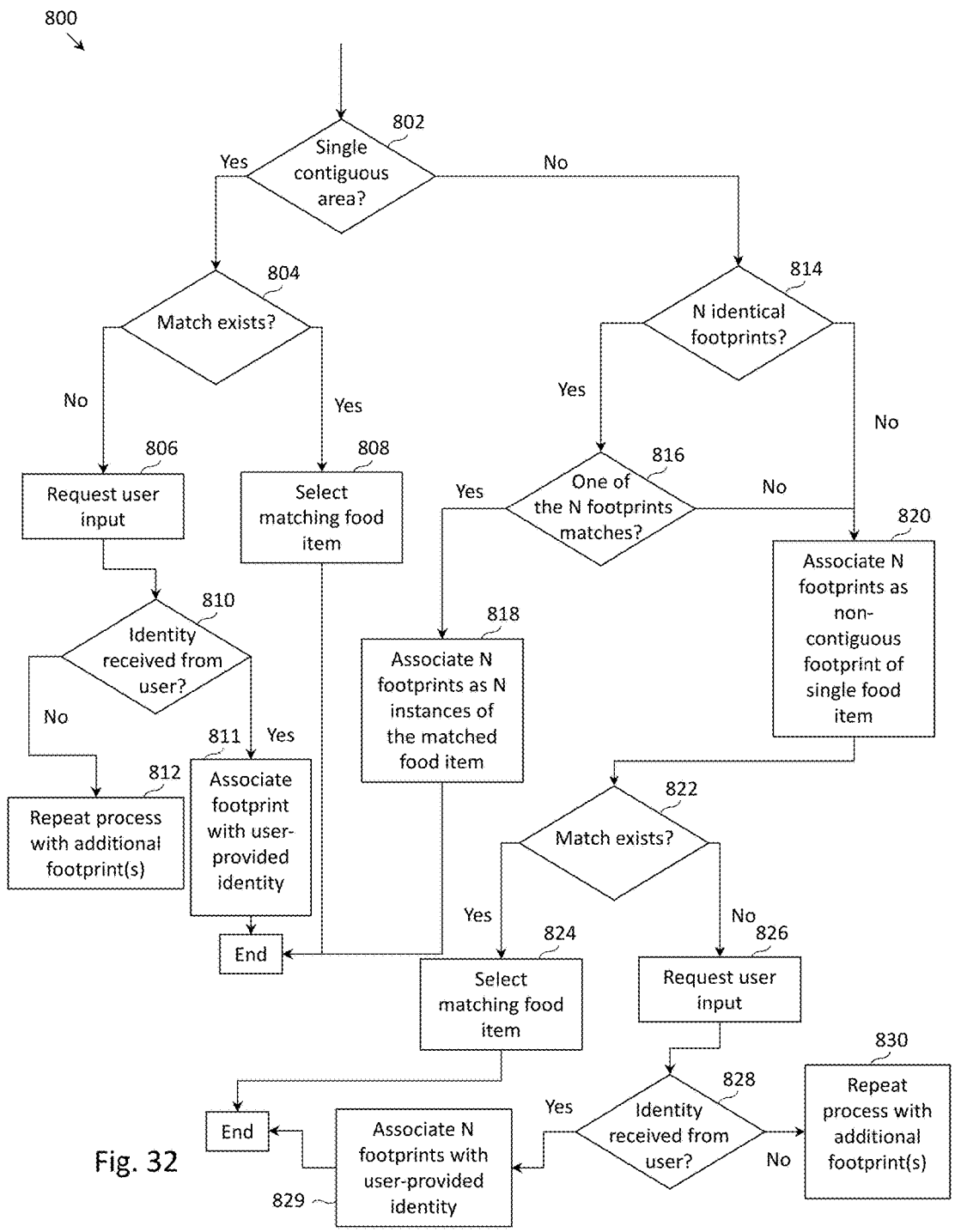
FIG. 32 depicts a flowchart of a process for matching one or more footprints to one or more food items, in accordance with one embodiment of the invention.

FIG. 32 depicts flowchart 800 of a process for matching one or more footprints to one or more food items, in accordance with one embodiment of the invention. Before the process begins, it is assumed that one or more footprints are detected by pressure-sensitive device 10 within a (short) sample window of T second (e.g., T=5 second). The handling of one or more footprints detected by pressure-sensitive device 10 over a longer period of time that exceeds T seconds is discussed below. At step 802, computing device 22 may determine whether the one or more footprints form a single contiguous area. If so, computing device 22 may determine whether the footprint matches any footprints stored in local (or global) food library 27. If so, the matching food item is selected (step 808). Otherwise, computing device 22 may request the user for additional input (step 806).

In response to step 806, the user may provide the identity of the one or more food items to computing device 22 (e.g., by speaking the identity, selecting the identity from a list), scan a bar code on the one or more food items, change an orientation of the one or more food items on pressure-sensitive device 10 (thereby providing additional one or more footprints of the one or more food items), and/or provide other user input. In the instance that the identity of the one or more food items is received from by the user (Yes branch of 810), computing device 22 may associate the footprint with the user-provided identity of the one or more food items (step 811). Otherwise, in the instance that additional one or more footprints is provided (with the weight of the one or more food items unchanged), computing device 22 may infer that one or more additional footprints of the one or more food items has been provided, and repeat the process of FIG. 32 for the additional one or more footprints (step 812), optionally cross-indexing by the originally provided one or more footprints to narrow the search for the identity of the one or more food items.

If computing device 22 determines that there are non-contiguous areas (No branch of 802), computing device 22 may further determine whether there are N substantially identical footprints, where N>1 (step 814). If so, computing device 22 may further determine whether any one of the N footprints matches a footprint stored in local (or global) food library 27 (step 816). If so, computing device 22 may associate the N footprints as N instances of the matched food item (step 818). Otherwise, if none of the N footprints matches a known footprint (No branch of 816) or if none of the N footprints are substantially identical, (No branch of 814), computing device 22 may associate the N footprints as a non-contiguous footprint of a single food item (step 820). At step 822, computing device 22 may determine whether the non-contiguous footprint matches any footprints stored in local (or global) food library 27. If so, the matching food item is selected (step 824). Otherwise, computing device 22 may request the user for additional input (step 826).

In response to step 826, the user may provide the identity of the one or more food items to computing device 22 (e.g., by speaking the identity, selecting the identity from a list), scan a bar code on the one or more food items, change an orientation of the one or more food items on pressure-sensitive device 10 (thereby providing additional one or more footprints of the one or more food items), and/or provide other user input. In the instance that the identity of the one or more food items is received from by the user (Yes branch of 828), computing device 22 may associate the N footprints with the user-provided identity of the one or more food items (step 829). Otherwise, in the instance that additional one or more footprints is provided (with the weight of the one or more food items unchanged), computing device 22 may infer that one or more additional footprints of the one or more food items has been provided, and repeat the process of FIG. 32 for the additional one or more footprints (step 830), optionally cross-indexing by the originally provided one or more footprints to narrow the search for the identity of the one or more food items.

While flowchart 800 addresses the scenarios of N substantially identical footprints (Yes branch of 816) or no substantially identical footprints (No branch of 816), flowchart 800 may be adapted to address the scenario in which there are N footprints that are substantially identical to one another (e.g., N circular footprints) and M additional footprints that are substantially identical to one another (e.g., M square footprints), for a total of N+M footprints. In this scenario, the M footprints would be processed per the same algorithm (No branch of 802), independent of the N footprints.

Returning to the discussion if N footprints are detected over a time period greater than T seconds, the process of flowchart 800 would still be followed, but using multiple invocations. For example, if three goldfish crackers were placed on pressure-sensitive device 10 at the same time, they would be processed in accordance with the process of flowchart 800 (resolved to 3 instances of one goldfish cracker). If ten minutes later, seven more goldfish crackers were placed on pressure-sensitive device 10, then they would also be processed in accordance with the process of flowchart 800 (resolved to 7 additional instances of the goldfish cracker).

One example traversal through flowchart 800 of FIG. 32 is now provided. Suppose a user places ten goldfish crackers on pressure-sensitive device 10, and goldfish crackers had never been registered by the meal accounting system. The footprints of the ten goldfish crackers will not form a single contiguous area, so the process will follow the No branch of decision element 802 (single contiguous area?). Next, since goldfish crackers are relatively uniform in shape and will have identical footprints, it is expected that the process will follow the Yes branch of decision element 814 (N identical footprints?). Since no footprints for goldfish crackers are yet on record, the process will follow the No branch of decision element 816 (One of the N footprints matches?). Next, as the ten footprints of the goldfish crackers will not match a single food item, the process will follow the No branch of decision element 822 (Match exists?). At step 826, computing device 22 may ask the user for the identity of the ten footprints. In one scenario, the user may provide the input of "10 goldfish crackers". In this case, the process may perform step 829 and associate the then footprints with the user-provided identity of "10 goldfish crackers". While not depicted in FIG. 32, computing device 22 may further associate one instance of the footprints with the user-provided identity (e.g., associate one of the footprints with the identity of "goldfish cracker"), such that in any subsequent traversal through FIG. 32, one or more goldfish crackers will be automatically identified by computing device 22.

In the example above, the user explicitly identified the ten goldfish crackers, allowing computing device 22 to infer the footprint of a single one of the ten goldfish crackers. In another embodiment (not depicted), the user could, following computing device 22 being unable to identify the 10 goldfish cracker, explicitly register the footprint of a single goldfish cracker. That is, in response to step 826 in which computing device 22 requests user input, the user may remove all but one of the goldfish crackers from pressure-sensitive device 10, and provide the identity of the single food item (i.e., in this example, "goldfish cracker"). More specifically, in a variant of FIG. 32 (not depicted), there may be a line connecting step 826 to decision element 802 (e.g., evaluating whether the footprint of the single goldfish cracker is formed by a single contiguous area). In this example, decision element 802 would evaluate to true (since the footprint of the single goldfish cracker is formed by a single contiguous area). The process would proceed to step 806 (receive user input); the user's input of "goldfish cracker" would be provided; decision element 810 would evaluate to true (since the identity would be received); and the footprint of a single goldfish cracker would be associated with the identity of "goldfish cracker" (step 811).

Following the registration of a single goldfish cracker (or all ten goldfish crackers), computing device 22 should be able to recognize any number of goldfish crackers. Indeed, the user could then put all ten goldfish crackers back onto pressure-sensitive device 10, and computing device 22 would then be able to determine that there are ten goldfish crackers on pressure-sensitive device 10 (traversing steps 802, 814, 816, 818).

Figure 33:
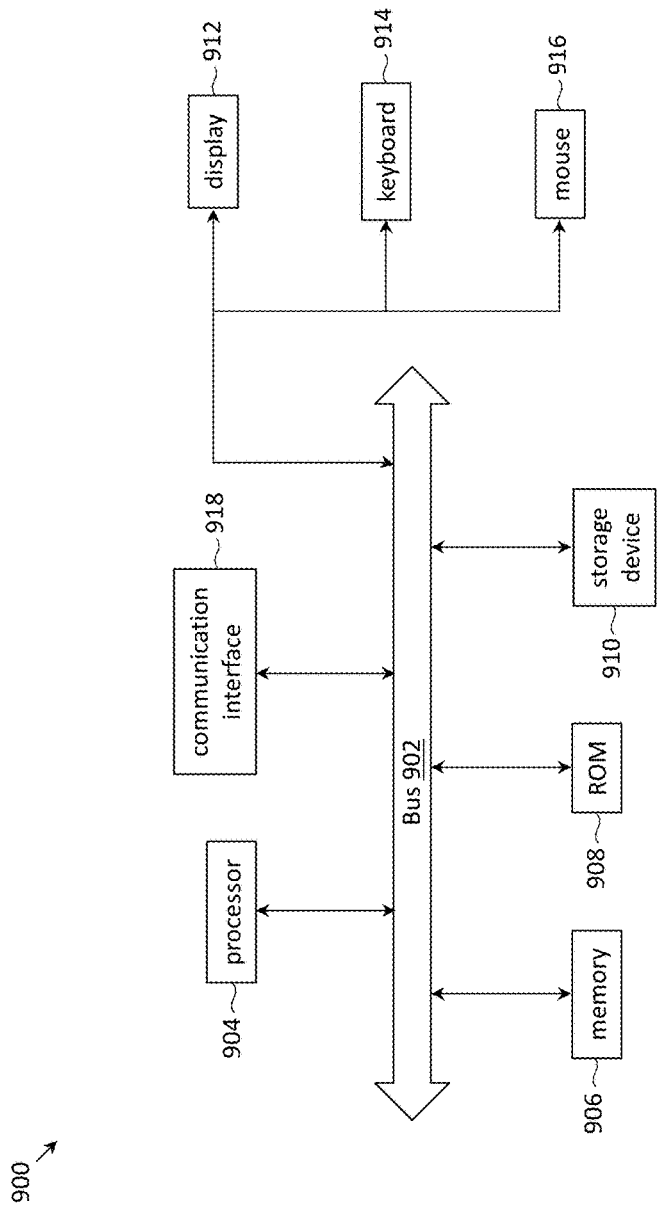
FIG. 33 depicts components of a computer system in which computer readable instructions instantiating the methods of the present invention may be stored and executed.

As is apparent from the foregoing discussion, aspects of the present invention involve the use of various computer systems and computer readable storage media having computer-readable instructions stored thereon. FIG. 33 provides an example of a system 900 that may be representative of any of the computing systems (e.g., computing device 22, server 18) discussed herein. Examples of system 900 may include a smartphone, a desktop, a laptop, a mainframe computer, an embedded system, etc. Note, not all of the various computer systems have all of the features of system 900. For example, certain ones of the computer systems discussed above may not include a display inasmuch as the display function may be provided by a client computer communicatively coupled to the computer system or a display function may be unnecessary. Such details are not critical to the present invention.

System 900 includes a bus 902 or other communication mechanism for communicating information, and a processor 904 coupled with the bus 902 for processing information. Computer system 900 also includes a main memory 906, such as a random access memory (RAM) or other dynamic storage device, coupled to the bus 902 for storing information and instructions to be executed by processor 904. Main memory 906 also may be used for storing temporary variables or other intermediate information during execution of instructions to be executed by processor 904. Computer system 900 further includes a read only memory (ROM) 908 or other static storage device coupled to the bus 902 for storing static information and instructions for the processor 904. A storage device 910, for example a hard disk, flash memory-based storage medium, or other storage medium from which processor 904 can read, is provided and coupled to the bus 902 for storing information and instructions (e.g., operating systems, applications programs and the like).

Computer system 900 may be coupled via the bus 902 to a display 912, such as a flat panel display, for displaying information to a computer user. An input device 914, such as a keyboard including alphanumeric and other keys, may be coupled to the bus 902 for communicating information and command selections to the processor 904. Another type of user input device is cursor control device 916, such as a mouse, a trackpad, or similar input device for communicating direction information and command selections to processor 904 and for controlling cursor movement on the display 912. Other user interface devices, such as microphones, speakers, etc. are not shown in detail but may be involved with the receipt of user input and/or presentation of output.

The processes referred to herein may be implemented by processor 904 executing appropriate sequences of computer-readable instructions contained in main memory 906. Such instructions may be read into main memory 906 from another computer-readable medium, such as storage device 910, and execution of the sequences of instructions contained in the main memory 906 causes the processor 904 to perform the associated actions. In alternative embodiments, hard-wired circuitry or firmware-controlled processing units may be used in place of or in combination with processor 904 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 900 or similar electronic computing device, that manipulates and transforms data represented as physical (electronic) quantities within its registers and memories into other data similarly represented as physical quantities within its memories or registers or other such information storage, transmission or display devices.

Computer system 900 also includes a communication interface 918 coupled to the bus 902. Communication interface 918 may provide a two-way data communication channel with a computer network, which provides connectivity to and among the various computer systems discussed above. For example, communication interface 918 may be a local area network (LAN) card to provide a data communication connection to a compatible LAN, which itself is communicatively coupled to the Internet through one or more Internet service provider networks. The precise details of such communication paths are not critical to the present invention. What is important is that computer system 900 can send and receive messages and data through the communication interface 918 and in that way communicate with hosts accessible via the Internet. It is noted that the components of system 900 may be located in a single device or located in a plurality of physically and/or geographically distributed devices.

Thus, a meal lifecycle management system has been described. It is to be understood that the above-description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A non-transitory machine-readable medium for a food preparation system comprising a pressure-sensitive device, a controller and a first datastore, the non-transitory machine-readable medium comprising instructions that, when executed by a processor of the controller, cause the processor to:

determine a first weight and a footprint of a first container based on first measurements from the pressure-sensitive device;

determine an identity of a food item contained in the first container based on the first weight and the footprint of the first container;

determine a first weight of a second container based on second measurements from the pressure-sensitive device;

subsequent to detecting a first change in weight of the second container, determine a second weight of the second container based on third measurements from the pressure-sensitive device;

determine a second weight of the first container based on fourth measurements from the pressure-sensitive device;

determine that a difference between the second weight and the first weight of the second container substantially equals a difference between the first weight and the second weight of the first container;

determine that a portion of the food item with weight equal to the difference between the first weight and the second weight of the first container has been transferred from the first container into the second container based on the determination that the difference between the second weight and the first weight of the second container substantially equals the difference between the first weight and the second weight of the first container; and store in the first datastore an association between (i) an amount of the food item that was transferred from the first container into the second container and (ii) the identity of the food item, wherein the amount of the food item that was transferred from the first container into the second container is based on the weight of the food item that was transferred from the first container into the second container.

2. The non-transitory machine-readable medium of claim 1, wherein the footprint of the first container includes a first footprint shape and a first pressure distribution, and wherein the first weight of the first container is determined by integrating the first pressure distribution over the first footprint shape.

3. The non-transitory machine-readable medium of claim 1, wherein the first weight and the footprint of the first container are received by the controller from the pressure-sensitive device.

4. The non-transitory machine-readable medium of claim 1, wherein the identity of the food item is determined by searching a second datastore for a food item identifier that is associated with the first weight and the footprint of the first container.

5. The non-transitory machine-readable medium of claim 1, further comprising instructions that cause the processor to display on a monitor communicatively coupled to the food preparation system, the footprint of the first container and a footprint of the second container within a representation of a surface of the pressure-sensitive device, wherein respective locations of the footprint of the first container and the footprint of the second container reflect respective locations of the first and second containers on the surface of the pressure-sensitive device.

6. The non-transitory machine-readable medium of claim 1, further comprising instructions that cause the processor to:

receive an indication that food is about to be consumed by a person;

subsequent to detecting a second change in weight of the second container, determine a third weight of the second container based on fifth measurements from the pressure-sensitive device;

determine a weight of the food item that is consumed by the person being equal to a difference between the second weight and the third weight of the second container; and store in the first datastore (i) the weight of the portion of the food item that was consumed by the person and (ii) the identity of the food item.

7. A non-transitory machine-readable medium for a food preparation system comprising a pressure-sensitive device, a controller and a first datastore, the non-transitory machine-readable medium comprising instructions that, when executed by a processor of the controller, cause the processor to:

determine a weight and a footprint of a food item based on first measurements from the pressure-sensitive device;

determine an identity of the food item based on the weight and the footprint of the food item;

determine a first weight of a container based on second measurements from the pressure-sensitive device;

subsequent to detecting a first change in weight of the container, determine a second weight of the container based on third measurements from the pressure-sensitive device;

determine that a difference between the second weight and the first weight of the container substantially equals the weight of the food item;

determine that the food item was placed into the container based on the determination that the difference between the second weight and the first weight of the container substantially equals the weight of the food item; and store in the first datastore an association between (i) an amount of the food item that was placed into the container and (ii) the identity of the food item, wherein the amount of the food item that was placed into the container is based on the weight of the food item that was placed into the container.

8. The non-transitory machine-readable medium of claim 7, wherein the footprint of the food item includes a first footprint shape and a first pressure distribution, and wherein the weight of the food item is determined by integrating the first pressure distribution over the first footprint shape.

9. The non-transitory machine-readable medium of claim 7, wherein the weight and the footprint of the food item are received by the controller from the pressure-sensitive device.

10. The non-transitory machine-readable medium of claim 7, wherein the identity of the food item is determined by searching a second datastore for a food item identifier that is associated with the weight and the footprint of the food item.

11. The non-transitory machine-readable medium of claim 7, further comprising instructions that cause the processor to display on a monitor communicatively coupled to the food preparation system, the footprint of the food item and a footprint of the container within a representation of a surface of the pressure-sensitive device, wherein respective locations of the footprint of the food item and the footprint of the container reflect respective locations of the food item and the container on the surface of the pressure-sensitive device.

12. The non-transitory machine-readable medium of claim 7, further comprising instructions that cause the processor to:

receive an indication that food is about to be consumed by a person;

subsequent to detecting a second change in weight of the container, determine a third weight of the container based on fourth measurements from the pressure-sensitive device;

determine a weight of the food item that is consumed by the person being equal to a difference between the second weight and the third weight of the container; and store in the first datastore at least one of (i) the weight of the portion of the food item that was consumed by the person, (ii) the identity of the food item or (iii) a time at which the portion of the food item was consumed by the person.

13. A non-transitory machine-readable medium for a food preparation system comprising a pressure-sensitive device, a controller and a first datastore, the non-transitory machine-readable medium comprising instructions that, when executed by a processor of the controller, cause the processor to:

determine a first weight and a first footprint of a food item based on first measurements from the pressure-sensitive device;

determine an identity of the food item based on the first weight and the footprint of the food item;

determine a first weight of a container based on second measurements from the pressure-sensitive device;

subsequent to detecting a first change in weight of the container, determine a second weight of the container based on third measurements from the pressure-sensitive device;

determine a second weight of the food item based on fourth measurements from the pressure-sensitive device;

determine that a difference between the second weight and the first weight of the container substantially equals a difference between the first weight and the second weight of the food item;

determine that a portion of the food item with weight equal to the difference between the first weight and the second weight of the food item has been placed into the container based on the determination that the difference between the second weight and the first weight of the container substantially equals the difference between the first weight and the second weight of the food item; and store in the first datastore an association between (i) an amount of the portion of the food item that was placed into the container and (ii) the identity of the food item, wherein the amount of the portion of the food item that was placed into the container is based on the weight of the portion of the food item that was placed into the container.

14. The non-transitory machine-readable medium of claim 13, wherein the first footprint of the food item includes a first footprint shape and a first pressure distribution, and wherein the first weight of the food item is determined by integrating the first pressure distribution over the first footprint shape.

15. The non-transitory machine-readable medium of claim 13, further comprising instructions that cause the processor to display, on a monitor communicatively coupled to the food preparation system, the first footprint of the food item and a footprint of the container within a representation of a surface of the pressure-sensitive device, wherein respective locations of the first footprint of the food item and the footprint of the container reflect respective locations of the food item and the container on the surface of the pressure-sensitive device.

16. The non-transitory machine-readable medium of claim 13, further comprising instructions that cause the processor to:
  prior to detecting the first change in weight of the container, further determine the first footprint of the food item being replaced with a second footprint of the food item; and
  store in the first datastore an association between (i) the identity of the food item, (ii) the first weight of the food item and (iii) the second footprint of the food item.

17. The non-transitory machine-readable medium of claim 16, further comprising instructions that cause the processor to:
  subsequent to detecting the first change in weight of the container, further determine the second footprint of the food item being replaced with a third footprint of the food item; and
  store in the first datastore an association between (i) the identity of the food item, (ii) the second weight of the food item and (iii) the third footprint of the food item.

18. The non-transitory machine-readable medium of claim 17, further comprising instructions that cause the processor to:
  determine the food item being removed from the pressure-sensitive device based on fifth measurements from the pressure-sensitive device;
  determine a weight and a footprint of an object based on sixth measurements from the pressure-sensitive device; and
  in response to determining the weight of the object being equal to the second weight of the food item and the footprint of the object being equal to the third footprint of the food item, determine the food item being placed on the pressure-sensitive device.

19. The non-transitory machine-readable medium of claim 13, further comprising instructions that cause the processor to:
  receive an indication that food is about to be consumed by a person;
  subsequent to detecting a second change in weight of the container, determine a third weight of the container based on fifth measurements from the pressure-sensitive device;
  determine a weight of the food item that is consumed by the person being equal to a difference between the second weight and the third weight of the container; and
  store in the first datastore an association between (i) the weight of the portion of the food item that was consumed by the person and (ii) the identity of the food item.

20. A non-transitory machine-readable medium for a food preparation system comprising a pressure-sensitive device, a controller and a first datastore, the non-transitory machine-readable medium comprising instructions that, when executed by a processor of the controller, cause the processor to:
  determine a first weight and a footprint of a container based on first measurements from the pressure-sensitive device;
  determine an identity of a first food item contained in the container based on the first weight and the footprint of the first container;
  determine a first weight and a first footprint of a second food item based on second measurements from the pressure-sensitive device;
  determine an identity of the second food item based on the first weight and the first footprint of the second food item;
  subsequent to detecting a change in weight of the second food item, determine a second weight and a second footprint of the second food item based on third measurements from the pressure-sensitive device;
  determine a second weight of the container based on fourth measurements from the pressure-sensitive device;
  determine that a difference between the second weight and the first weight of the second food item substantially equals a difference between the first weight and the second weight of the container;
  determine that a portion of the first food item with weight equal to the difference between the first weight and the second weight of the container has been transferred to the second food item based on the determination that the difference between the second weight and the first weight of the second food item substantially equals the difference between the first weight and the second weight of the container; and
  store in the first datastore characteristics of the second food item, the characteristics including the second footprint of the second food item, the first weight of the second food item and the weight of the portion of the first food item that was transferred to the second food item.

* * * * *